United States Patent
Chang et al.

(10) Patent No.: US 12,077,557 B2
(45) Date of Patent: Sep. 3, 2024

(54) PUROMYCIN-BASED PROBES AND METHODS OF USE THEREOF

(71) Applicant: The Regents of the University of California, Oakland, CA (US)

(72) Inventors: Christopher J. Chang, Berkeley, CA (US); Yik Sham Clive Chung, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 953 days.

(21) Appl. No.: 16/981,511

(22) PCT Filed: Mar. 20, 2019

(86) PCT No.: PCT/US2019/023242
§ 371 (c)(1),
(2) Date: Sep. 16, 2020

(87) PCT Pub. No.: WO2019/183270
PCT Pub. Date: Sep. 26, 2019

(65) Prior Publication Data
US 2021/0061842 A1  Mar. 4, 2021

Related U.S. Application Data

(60) Provisional application No. 62/647,481, filed on Mar. 23, 2018.

(51) Int. Cl.
*C07H 19/16* (2006.01)
*C12Q 1/26* (2006.01)
*G01N 33/58* (2006.01)

(52) U.S. Cl.
CPC ............... *C07H 19/16* (2013.01); *C12Q 1/26* (2013.01); *G01N 33/582* (2013.01)

(58) Field of Classification Search
None
See application file for complete search history.

(56) References Cited

U.S. PATENT DOCUMENTS

| | | |
|---|---|---|
| 2006/0057069 A1 | 3/2006 | Starck-Green et al. |
| 2008/0312103 A1 | 12/2008 | Nemoto et al. |
| 2016/0015830 A1 | 1/2016 | Lin et al. |
| 2016/0168205 A1 | 6/2016 | Salic et al. |
| 2016/0176919 A1 * | 6/2016 | Cohen ................ A01K 67/0275 536/27.22 |

FOREIGN PATENT DOCUMENTS

WO  WO 2017/089890  6/2017

OTHER PUBLICATIONS

Starck, et al.; "A General Approach to Detect Protein Expression In Vivo Using Fluorescent Puromycin Conjugates"; Chemistry & Biology; vol. 11, pp. 999-1008 (Jul. 2004).

* cited by examiner

*Primary Examiner* — Traviss C McIntosh, III
(74) *Attorney, Agent, or Firm* — Rudy J. Ng; Paula Borden; Bozicevic, Field & Francis LLP

(57) ABSTRACT

The present disclosure provides puromycin-based probes, as well as compositions and kits comprising the probes. The present disclosure provides methods of detecting an analyte, and imaging methods, using the probes.

18 Claims, 31 Drawing Sheets

PUROMYCIN-BASED PROBES AND METHODS OF USE THEREOF

CROSS-REFERENCE

This application is a national stage filing under 35 U.S.C. § 371 of PCT/US2019/023242, filed Mar. 20, 2019, which claims the benefit of U.S. Provisional Patent Application No. 62/647,481, filed Mar. 23, 2018, which applications are incorporated herein by reference in their entirety.

STATEMENT REGARDING FEDERALLY SPONSORED RESEARCH

This invention was made with government support under Grant No. GM079465 awarded by the National Institutes of Health. The government has certain rights in the invention.

INTRODUCTION

Fluorescence imaging is a powerful approach for studying small molecules and metal ions in biological specimens owing to its high sensitivity, good spatial and temporal resolution, and non-invasive nature. Moreover, fluorescent probes that operate through activity-based sensing (ABS) by specific reactions between probes and analytes offer excellent selectivity toward target analytes over other biological substrates. An example is ABS for $H_2O_2$, which is a redox-active small molecule participating in not only immune responses but also cellular signaling and communications. Through $H_2O_2$-mediated specific boronate cleavage, ABS of $H_2O_2$ have been used to decipher principles of $H_2O_2$ signaling, including identification of particular aquaporin subtypes as $H_2O_2$ channels, $H_2O_2$ sources and targets in stem cell maintenance and neurogenesis, and respiring mitochondria as primary source of $H_2O_2$ for brain cell signaling. Despite their utility, these probes are mostly limited to transient analysis of dissociated cells in culture and are not compatible with fixed samples that would open new possibilities to assess a broader range of cell to in vivo tissue specimens.

There is a need in the art for fluorescent probes for histochemical analysis of analytes in cells, both in vitro and in vivo.

SUMMARY

The present disclosure provides puromycin-based probes, as well as compositions and kits comprising the probes. The present disclosure provides methods of detecting an analyte, and imaging methods, using the probes.

BRIEF DESCRIPTION OF THE DRAWINGS

FIG. 4A shows LC chromatograms of Peroxymycin-1 (0.3 mM) in the solution mixture at different time intervals. FIGS. 4B and 4C show MS of the peak with retention time of 6.46 min and 8.06 min respectively.

FIG. 5a shows LC chromatograms of $H_2S$-Puro-1 (0.3 mM) in the solution mixture at different time intervals. FIG. 5B shows MS of the peak with retention time of 7.57 min.

FIG. 6a shows LC chromatograms of GSH-Puro-1 (0.3 mM) in the solution mixture at different time intervals. FIGS. 6b and 6c shows MS of the peak with retention time of 7.21 and 6.57 min, respectively.

FIGS. 21a and 21b shows imaging in PBS without or with fixation by 4% paraformaldehyde solution respectively. FIG. 21c shows cellular fluorescence intensities of the HeLa cells as determined by ImageJ. All the data are shown as mean±SEM. (n=5).

Figure 1:
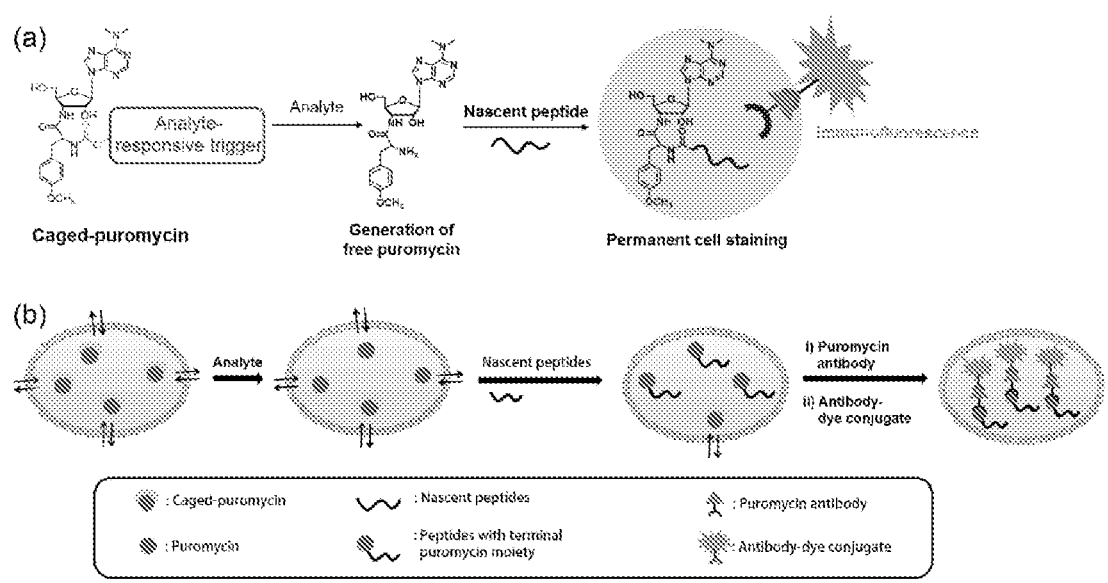
FIGS. 1A and 1B show the design and schematic cartoon illustrating working principle of puromycin-based probes for imaging target analytes respectively.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a probe" includes a plurality of such probes and reference to "the probe" includes reference to one or more probes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides puromycin-based probes, as well as compositions and kits comprising the probes. The present disclosure provides methods of detecting an analyte, and imaging methods, using the probes.

Probes

The present disclosure provides probe compounds that provide for the selective detection of an analyte of interest that is a redox-active small molecule. Target analytes of interest that are redox-active small molecules include, but are not limited to, ROS, RSS, RCS, ROS scavengers and redox-active metal ions. The subject probe can react with a target analyte, leading to the release of a detectable free puromycin moiety. The subject probe compounds exploit the mechanism of action of the antibiotic puromycin. Naturally occurring puromycin contains an N,N-dimethyl adenosine fused to an O-methyl-L-tyrosine amino acid, thereby mimicking an amino acid charged tRNA. During active translation, puromycin binds to the translating ribosome where its α-amino group covalently attacks the carbonyl of the aminoacyl-tRNA ester, causing premature termination of translation. Puromycin can selectively incorporate into the C-terminus of full-length proteins during translation without inhibiting translation or inducing a stress response. Thus, the use of puromycin or puromycin variants provides a method of labeling a newly synthesized protein which can be subsequently detected, e.g., via immunostaining. The peptide-incorporated puromycin can be immunostained and detected by a measureable change which correlates to the level of target analytes in the samples. Immunostaining can involve colorimetric, fluorogenic, bioluminescent or chemiluminescent responses.

The term "ROS" refers to a reactive oxygen species which are transient species that due to their high chemical reactivity can lead to lipid peroxidation and oxidation of some enzymes, and a massive protein oxidation and degradation. Reactive oxygen species (ROS), include but are not limited to, hydroxyl radical (HO.), superoxide anion (.$O_2^-$), singlet oxygen ($^1O_2^-$), hydrogen peroxide ($H_2O_2$), lipid peroxides (ROOH), ozone ($O_3$), nitric oxide (NO), hypochlorous acid (HOCl), peroxyl radical (ROO.) and peroxynitrite anion (ONOO—).

The term "RSS" refers to a reactive sulfur species and refers to a family of sulfur-based compounds that can oxidize and inhibit thiol-proteins and enzymes. RSS can often be formed by the oxidation of thiols and disulfides into higher oxidation states. RSS of interest include, but are not limited to, $H_2S$ and related molecules, persulfides, polysulfides and thiosulfate, see e.g., Mishanina et al. (Biogenesis of reactive sulfur species for signaling by hydrogen sulfide oxidation pathways, Nature Chemical Biology volume 11, pages 457-464 (2015)) and Giles and Jacob ("Reactive sulfur species: an emerging concept in oxidative stress", Biol Chem. 383: 375-88).

The term "RCS" refers to a reactive carbonyl species. A RCS can be a naturally occurring molecule that includes a ketone or aldehyde functional group which is capable of reaction with a subject probe. RCS of interest include, but are not limited to, formaldehyde, 4-hydroxynonenal, dehydroascorbate, glucosone, oxaloacetate, methylglyoxal, acetaldehyde, pyruvate, and glucose. In certain embodiments, the reactive carbonyl species is formaldehyde and the subject probe is selective for formaldehyde over other reactive carbonyl species that may be present in a sample of interest. Formaldehyde (FA), the simplest aldehyde, is a reactive carbonyl species (RCS) that has long been known as a human toxin and carcinogen that is released into the environment from natural (e.g., biomass combustion, solar degradation of humic substances, vegetation and microbe emissions) as well as anthropogenic (e.g., FA production and fumigation, vehicle exhaust, etc.) sources. At the same time, FA is also produced endogenously in the body by demethylase and oxidase enzymes that regulate epigenetics and metabolism, such as lysine-specific demethylase 1 (LSD1), JmjC domain-containing proteins and semicarbazide-sensitive amine oxidase. Active degradation by formaldehyde dehydrogenase/S-nitrosoglutathione reductase and aldehyde dehydrogenase 2 enzymes gives physiological FA levels ranging from 100 μM in blood to 400 μM intracellularly. Elevations of FA and related RCS are implicated in a variety of disease pathologies, including various cancers, neurodegenerative diseases, diabetes, and chronic liver and heart disorders.

The term "ROS scavengers" refers to compounds or groups with can selectively react with a ROS, e.g., as described by Mates et al. (Chemical and biological activity of free radical 'scavengers' in allergic diseases, Clinica Chimica Acta 296 (2000) 1-15). Any convenient ROS and ROS scavengers can be targeted and/or adapted for use in the subject probes and methods. ROS scavengers of interest include but are not limited to, glutathione and thioredoxin reductase.

In addition, redox-active metal ions can be detected using the subject probes. Any convenient redox-active metal ions of interest can be targeted as analytes in the subject methods. Redox-active metal ions of interest include, but are not limited to, manganese, iron, cobalt, nickel, copper and zinc ions.

In some case, the probe compounds provide for the selective detection of a target analyte (e.g., a reactive oxygen species such as $H_2O_2$) in a living cell (in vivo, ex vivo, or in vitro), in a multicellular organism, in extracellular fluid, or in a cell-free sample.

The subject probe compounds are self-immolative, e.g., compounds that respond to an external stimulus (e.g., a redox-active small molecule) to undergo a fragmentation or cleavage to release a detectable moiety. In the subject probes, the detectable moiety can be a puromycin detectable moiety For example, in some embodiments, the subject compounds include an ROS— (e.g., a $H_2O_2$—) sensitive aryl or heteroaryl boronate group that is connected to a puromycin detectable moiety via a cleavable linker. The aryl or heteroaryl boronate group is conjugated to a cleavable bond of the cleavable linker, such that upon an oxidation reaction of the aryl or heteroaryl boronate (e.g., after reaction with an ROS such as $H_2O_2$), electrons can be donated or resonate through the conjugated system to spontaneously cleave the cleavable bond of the linker and release an amino group of the puromycin detectable moiety.

Aspects of the present disclosure include a probe compound of formula (I):

P-L-T    (I)

wherein:
P is a puromycin detectable moiety;
L is a self-immolative linker; and
T is an analyte-responsive trigger group configured to initiate cleavage of L upon contact with a target analyte. P and L are linked via the alpha-amino group of the puromycin detectable moiety, such that the biological activity of the puromycin is blocked. Free puromycin binds to the translating ribosome during active translation via its α-amino group which covalently attacks the carbonyl of the aminoacyl-tRNA ester, causing premature termination of translation. In general terms, the analyte-responsive trigger group chemoselectively reacts with the analyte to produce a triggered group (T*) which in configured to destabilize the self-immolative linker to which it is attached, thereby providing for spontaneous cleavage of the linker and ultimately release of free puromycin.

Puromycin Detectable Moiety

Puromycin is an aminonucleoside antibiotic, derived from the *Streptomyces alboniger* bacterium, that causes premature chain termination during translation taking place in the ribosome. The subject probe compounds exploit the mechanism of action of the antibiotic puromycin. Naturally occurring puromycin contains an N,N-dimethyl adenosine fused to an O-methyl-L-tyrosine amino acid, thereby mimicking an amino acid charged tRNA. During active translation, puromycin binds to the translating ribosome where its α-amino group covalently attacks the carbonyl of the aminoacyl-tRNA ester, causing premature termination of translation. Puromycin can selectively incorporate into the C-terminus of full-length proteins during translation without inhibiting translation or inducing a stress response. Thus, the use of puromycin or puromycin variants provides a method of labeling a newly synthesized protein which can be subsequently detected, e.g., via immunostaining.

Because the α-amino group of puromycin is important for puromycin function, installation of a self immolative linker on the α-amino group can act as a blocking group, thereby rendering the resulting puromycin inactive, until the linker is cleaved, e.g., via application of a stimulus.

Any convenient puromycin compounds or moieties can be adapted for use in the subject probes. As used herein, the terms "puromycin detectable moiety", "puromycin moiety" "puromycin variant", "puro" and "puromycin compound" are used interchangeably and refer to naturally occurring puromycin, puromycin analogs and puromycin derivatives which are capable of covalently linking to a nascent peptide chain. Puromycin analogs of interest which can be adapted for use in the subject probes include those described by Salic et al. in US 2016/0168205, and Hecht et al. in US 2018/0002709, the disclosures of which are herein incorporated by reference. In some cases, the puromycin moiety can be further derivatized via conjugation of a molecule of interest to a chemoselective tag. In some cases, the puromycin moiety is a dipeptidyl-puromcon amino nucleoside (see e.g., US 2018/0002709). In some cases, the puromycin moiety can be used in conjunction with non-naturally occurring protein synthesis machinery to provide a detectable moiety.

In some embodiments, a puromycin detectable moiety is described by formula (II):

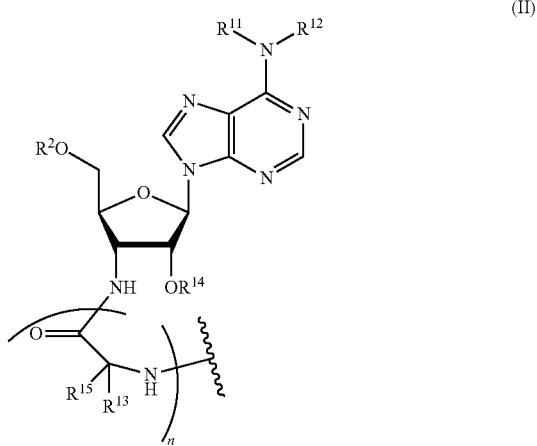

wherein:
n is 1 or 2;
$R^{11}$ and $R^{12}$ are each independently hydrogen, alkyl or substituted alkyl;
each $R^{13}$ and $R^{14}$ are each independently hydrogen, $C_{1-6}$ alkyl or $C_{1-6}$ substituted alkyl;
$R^2$ and each $R^{15}$ is independently selected from hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, phosphoryl, phosphonyl group, substituted or unsubstituted aryl, substituted or unsubstituted heteroaryl.

In certain instances of formula (II), n is 1. In certain instances of formula (II), n is 2. In certain instances of formula (II), $R^{11}$ and $R^{12}$ are each hydrogen. In certain instances of formula (II), $R^{11}$ and $R^{12}$ are each $C_{1-6}$ alkyl. In certain instances of formula (II), $R^{11}$ and $R^{12}$ are each methyl. In certain instances of formula (II), $R^2$, each $R^{13}$ and $R^{14}$ are each hydrogen. In certain instances of formula (II), $R^2$ is hydrogen. In certain instances of formula (II), $R^{13}$ is hydrogen. In certain instances of formula (II), $R^{14}$ is hydrogen.

In some case of formula (II), $R^2$ is independently selected from hydrogen, substituted or unsubstituted alkyl, substituted or unsubstituted cycloalkyl, substituted or unsubstituted heteroalkyl, substituted or unsubstituted heterocycloalkyl, propargyl, phosphate, alkanoyl, substituted alkanoyl, sulfonyl, isocyanate-yl, alkenyl, alkynyl, phosphoryl, phosphonyl group, substituted or unsubstituted aryl, substituted or unsubstituted heteroaryl. In certain instances of formula (I), $R^2$ is hydrogen, $C_{1-6}$ alkyl or $C_{1-6}$ substituted alkyl.

In some embodiments of formula (II), $R^{15}$ is selected from alkyl, substituted alkyl, aryl, substituted aryl, heteroaryl and substituted heteroaryl. $R^{15}$ can be an aryl-alkyl, such as a phenyl-alkyl. In certain instances of formula (II), $R^{15}$ is benzyl or substituted benzyl. In certain instances of formula (II), $R^{15}$ is alkoxy-phenyl-methyl or substituted alkoxy-phenyl-methyl, where the alkoxy substituent can be at the para-position. It is understood that the alpha-carbon of the amino acid residue(s) of the puromycin moiety described herein can have a chirality that corresponds to the (L)-stereochemistry of a naturally occurring amino acid, e.g., when $R^{15}$ is an analog or derivative of the natural puromycin sidechain group and $R^{13}$ is H.

In certain instances of formula (II), n=1 such that the puromycin detectable moiety is described by formula (III):

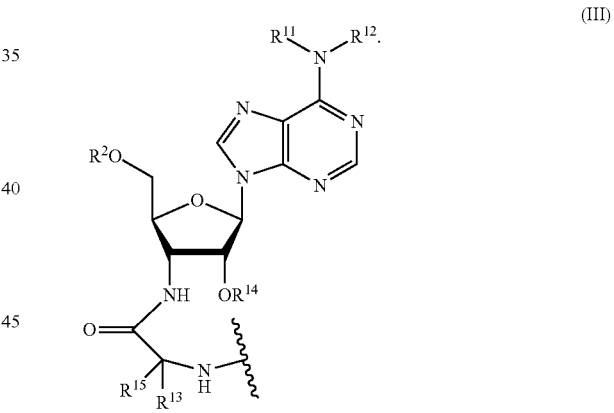

wherein:
$R^{11}$ and $R^{12}$ are each independently hydrogen, alkyl or substituted alkyl;
$R^2$, each $R^{13}$ and $R^{14}$ are each independently hydrogen, $C_{1-6}$ alkyl or $C_{1-6}$ substituted alkyl;
each $R^{15}$ is independently selected from alkyl, substituted alkyl, aryl, substituted aryl, heteroaryl and substituted heteroaryl. In formula (III), $R^{15}$ can be an aryl-alkyl, such as a phenyl-alkyl. In certain instances of formula (III), $R^{15}$ is benzyl or substituted benzyl. In certain instances of formula (III), $R^{15}$ is alkoxy-phenyl-methyl or substituted alkoxy-phenyl-methyl, where the alkoxy substituent can be at the para-position.

In certain instances of formula (III), the puromycin detectable moiety is described by formula (IV):

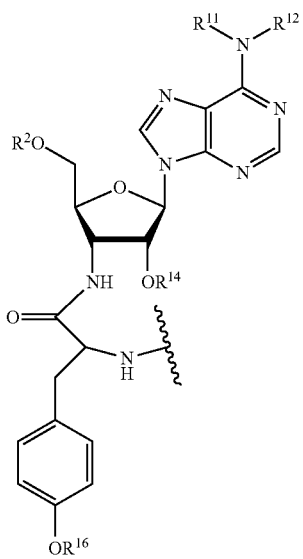

(IV)

wherein:

$R^{11}$ and $R^{12}$ are each independently hydrogen, alkyl or substituted alkyl;

$R^2$, each $R^{13}$ and $R^{14}$ are each independently hydrogen, $C_{1-6}$ alkyl or $C_{1-6}$ substituted alkyl; and $R^{16}$ is selected from hydrogen, alkyl, substituted alkyl, substituted or unsubstituted cycloalkyl, substituted or unsubstituted heteroalkyl, alkenyl, substituted alkenyl, alkynyl, substituted alkynyl, alkanoyl, substituted alkanoyl, aroyl, substituted aroyl, heteroaroyl, substituted heteroaroyl, phosphoryl, phosphonyl group, phosphate and sulfonyl.

In certain instances of formula (III) or (IV), $R^{11}$ and $R^{12}$ are each hydrogen. In certain instances of formula (III) or (IV), $R^{11}$ and $R^{12}$ are each $C_{1-6}$ alkyl. In certain instances of formula (II) or (III), $R^{11}$ and $R^{12}$ are each methyl. In certain instances of formula (III) or (IV), $R^2$ and $R^{14}$ are each hydrogen. In certain instances of formula (III) or (IV), $R^2$ is hydrogen. In certain instances of formula (III) or (IV), $R^{14}$ is hydrogen.

In some case of formula (III) or (IV), $R^2$ is independently selected from hydrogen, substituted or unsubstituted alkyl, substituted or unsubstituted cycloalkyl, substituted or unsubstituted heteroalkyl, substituted or unsubstituted heterocycloalkyl, propargyl, phosphate, alkanoyl, substituted alkanoyl, sulfonyl, isocyanate-yl, alkenyl, alkynyl, phosphoryl, phosphonyl group, substituted or unsubstituted aryl, substituted or unsubstituted heteroaryl. In certain instances of formula (III) or (IV), $R^2$ is hydrogen, $C_{1-6}$ alkyl or $C_{1-6}$ substituted alkyl.

In some cases of formula (IV), the puromycin detectable moiety is puromycin:

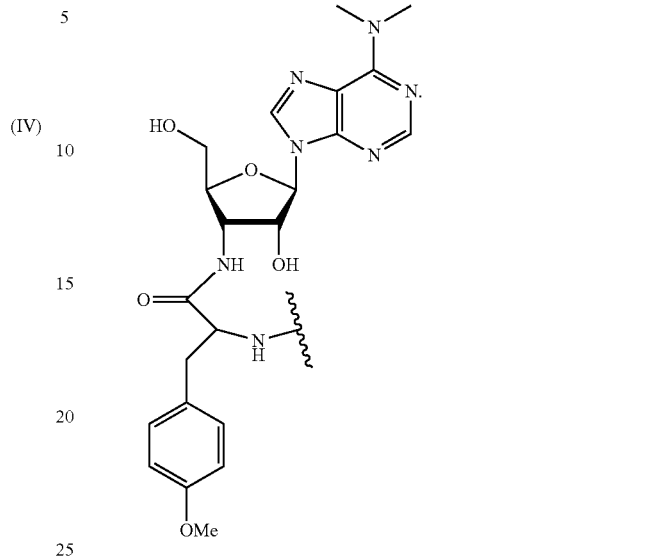

Also provide are subject probes that incorporate a puromycin analog such as those described by Salic et al. in US 2016/0168205. In some embodiments, a puromycin detectable moiety has the following formula:

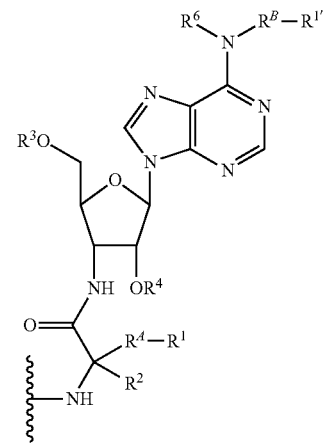

wherein:

$R^A$ is a bond, or an optionally substituted aliphatic group, heteroaliphatic group, aryl group, and heteroaryl group, or a combination thereof;

$R^B$ is a bond or a $C_{1-6}$ aliphatic moiety;

$R^1$ is hydrogen or a reactive group capable of undergoing a bioorthogonal reaction;

$R^{1'}$ is hydrogen or a reactive group capable of undergoing a bioorthogonal reaction; wherein R1 and R1' are not simultaneously hydrogen;

$R^2$ is hydrogen or $C_{1-6}$ aliphatic group;

$R^3$ and $R^4$ are each independently hydrogen or a protecting group; and $R^6$ is hydrogen or $C_{1-6}$ aliphatic group.

Puromycin analogs of interest which find use as a puromycin detectable moiety in the subject probes include, but are not limited to, e.g., O-demethylpuromycin, O-propargylpuromycin, 9-{3'-deoxy-3'-[(4-methyl-L-phenylalanyl)amino]-β-D-ribofuranosyl}-6-(N,N'-dimethylamino)purine [L-(4-Me)-Phe-PANS], and 6-dimethylamino-9-[3-(p-azido-L-beta-phenylalanylamino)-3-deoxy-beta-ribofuranosyl]purine.

Self Immolative Linker

A self-immolative linker is a linker that is cleavable upon activation. The subject probes of formula (I) include a cleavable linker group (L) that masks the biological activity and provides for release of the puromycin moiety (P). The cleavable linker is stable until activation, e.g., via reaction of a linked trigger group (T) with a target analyte, whereby the linker becomes labile. As such, release of P includes cleavage of a cleavable bond to release a leaving group (e.g., the amino group of the puromycin moiety).

The linker can include one or more groups such as, but not limited to, alkyl, ether, carbamate, carbonate, carbamide (urea), ester, thioester, aryl, amide, imines, phosphate esters, hydrazones, acetals, orthoesters, and combinations thereof. In some instances, the alpha-amino group of the puromycin moiety is connected to the self-immolative linker via a cleavable functional linking group such as a carbamate, a urea or an amide. In some embodiments, the L linker is described the following structure:

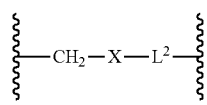

where X is a leaving group and $L^2$ is a linking group, wherein the bond that connects X to the adjacent —$CH_2$— group (e.g., $CH_2$—X) is a cleavable bond. In some embodiments X is oxygen or sulfur. In some embodiments, the leaving group is a carbamate, a carbonate, a thiol, an alcohol, an amino (e.g., an aryl amino) or a phenol group.

In certain embodiments, the linking group $L^2$ is a covalent bond or a chain of between 1 and 12 atoms in length (e.g., between 1 and 10, 1 and 8, 1 and 6 or 1 and 4 atoms in length). In some cases, $L^2$ is a chain of between 1 and 12 atoms in length that is linked to the amino leaving group of the puromycin detectable moiety Y (e.g., $L^2$ has a structure $L^3$-$X^2$ where $L^3$ is a linking group and $X^2$ is the amino leaving group, e.g., —NH—, such that upon cleavage of the cleavable bond ($CH_2$—X), a moiety is released (e.g., HX-$L^3$-NH—Y) that includes both the first leaving group (X), $L^3$ and —NH—Y. In such cases, the released moiety (e.g., HX-$L^3$-NH—Y) may undergo further cleavage or fragmentation (e.g., via an intramolecular cyclization-release) to release the puromycin moiety $H_2N$—Y, a moiety that may be directly or indirectly detected. In some embodiments, $L^2$ is a covalent bond, such that upon cleavage of the cleavable bond ($CH_2$—X), a puromycin moiety is released. When referring to the puromycin detectable moiety that is released it is understood that the leaving group (X and/or $X^2$) and segments of the linker may be attached to the puromycin detectable moiety being described. It is understood that in any of the embodiments described herein that upon cleavage of the cleavable bond of the linker, a moiety is released that may be directly or indirectly detected, or that may undergo further cleavage/fragmentation (e.g., via an intramolecular cyclization-release) prior to being detected.

Any convenient self-immolative linkers may be adapted for use in the subject probes. In certain instances, the self immolative linker L comprises a group selected from the following, or a derivative or functional analog thereof:

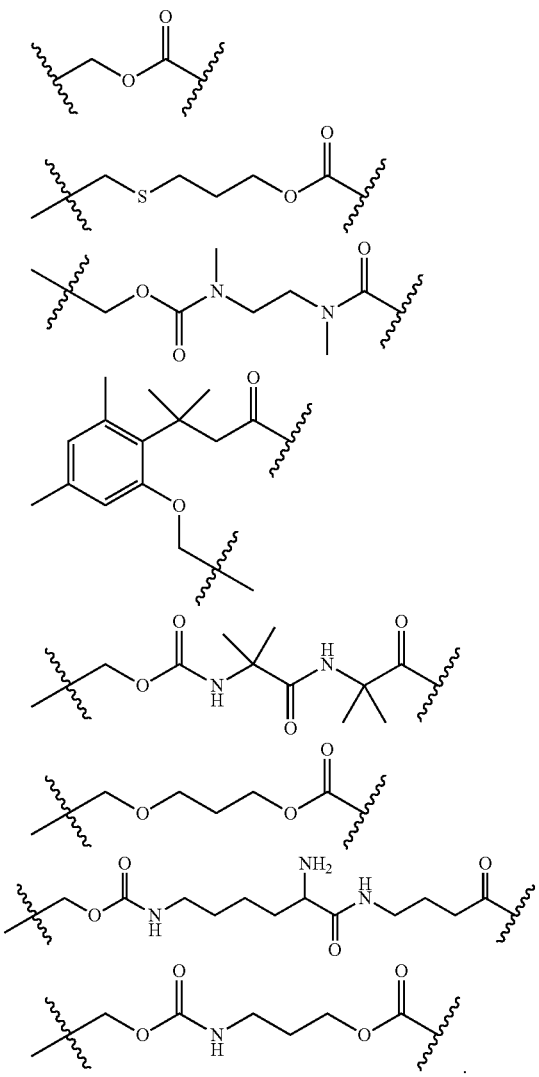

Analyte-Responsive Triggers

An analyte-responsive trigger (T) of the probe of formula (I) includes a chemical functional group which is configured for selective reaction with a target analyte. The analyte-responsive trigger group is attached to, and configured to trigger cleavage of, a self-immolative linker that connects the trigger group to the amino group of the probe. This analyte-responsive reaction can lead to generation of an intermediate moiety including a labile bond(s) which can undergo spontaneous self-immolation to release a free puromycin molecule. A variety of functional groups and moieties can be adapted for use in the subject probes to connect to a self-immolative linker and provide for spontaneous cleavage of the linker upon contact with, and reaction with, a target analyte. Target analytes of interest for which analyte-responsive triggers can be utilized include, but are not limited to, ROS, RSS, RCS, ROS scavengers and redox-active metal ions.

ROS-Responsive Trigger Group

In some instances, the analyte-responsive trigger is ROS-responsive. The ROS-responsive trigger group can include a boronic acid or boronate group which is capable of a hydroboration-oxidation reaction with a ROS. This disclosure provides a compound of formula (XII):

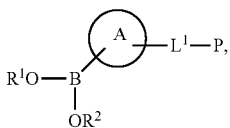

(XII)

wherein

R[1] and R[2] are independently selected from hydrogen, alkyl and substituted alkyl; or R[1] and R[2] together form a boronic ester ring or substituted boronic ester ring;

A ring is selected from aryl, substituted aryl, heteroaryl, and substituted heteroaryl;

L[1] is cleavable linker group that provides for release of Y upon reaction of the —B(OR[1])(OR[2]) group with a reactive oxygen species; and P is a puromycin detectable moiety that is released upon reaction of the probe with a reactive oxygen species; wherein, after release, the puromycin detectable moiety can be detected, either directly or indirectly (e.g., by immunostaining as described herein).

In formula (XI), R[1] and R[2] can be independently selected from hydrogen, alkyl and substituted alkyl. In certain instances, both R[1] and R[2] are hydrogen. In certain instances, both R[1] and R[2] are alkyl, such as, for example, methyl, ethyl, propyl, isopropyl, and butyl. In certain instances, R[1] and R[2] together form a boronic ester ring or substituted boronic ester ring. In certain instances, R[1] and R[2] together form a boronic ester ring. In certain instances, R[1] and R[2] together form a substituted boronic ester ring. In certain instances, the —B(OR[1])(OR[2]) group is selected from the following:

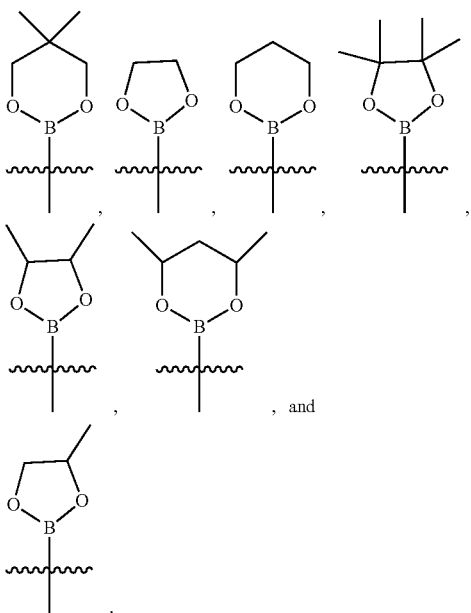

In formula (XI), the A ring can be selected from aryl, substituted aryl, heteroaryl, and substituted heteroaryl. In certain instances, the A ring is aryl. In certain instances, the A ring is substituted aryl. In certain instances, the A ring is phenyl. In certain instances, the A ring is substituted phenyl. In certain instances, the A ring is heteroaryl. In certain instances, the A ring is substituted heteroaryl. In certain instances, the A ring is pyridinyl. In certain instances, the A ring is substituted pyridinyl. The A ring connects the —B(OR[1])(OR[2]) group and L. The arrangement of these groups on the A ring is at any suitable ring positions that provides for electronic communication between the two groups (e.g., delocalization of a lone pair of electrons from one group to the other). For example, when A is a phenyl ring, arrangement of the —B(OR[1])(OR[2]) group and L[1] group either ortho- or para- to each other provides for delocalization of a lone pair of electrons from the site of —B(OR[1])(OR[2]) group oxidation to the cleavable bond of the cleavable linker.

In formula (XI), L[1] is cleavable linker group that provides for release of P upon reaction of the —B(OR[1])(OR[2]) group with a reactive oxygen species, where release of P includes cleavage of a cleavable bond to release a leaving group. For example, upon reaction (e.g., a hydroboration-oxidation reaction) of the aryl or heteroaryl —B(OR[1])(OR[2]) group with a reactive oxygen species (e.g., $H_2O_2$), the cleavable bond of the cleavable linking group L[1] is spontaneously cleaved to release the leaving group and the puromycin detectable moiety P. The cleavable bond connects the leaving group to an adjacent carbon atom that is conjugated to the aryl boronate group that is oxidized. A cascade occurs in which an electron pair is donated from the site of oxidation through the aryl or heteroaryl group to the carbon atom adjacent to the leaving group of the linker, thereby cleaving the cleavable bond. The L[1] linker group provides for release of P by fragmentation or cleavage of the linker with the donation of the electron pair. The L[1] linker group comprises segments of atoms, in which the segments can be displaced into two byproducts after a cleavage-inducing stimulus (e.g., reaction of the —B(OR[1])(OR[2]) group with a reactive oxygen species).

The L[1] linker group can include one or more groups such as, but not limited to, alkyl, ether, carbamate, carbonate, carbamide (urea), ester, thioester, aryl, amide, imines, phosphate esters, hydrazones, acetals, orthoesters, and combinations thereof. In some embodiments, the L[1] linker group is described the following structure:

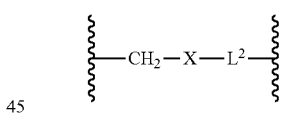

where X is a leaving group and L[2] is a linking group, wherein the bond that connects X to the adjacent —CH[2]— group (e.g., CH[2]—X) is a cleavable bond. In some embodiments X is oxygen or sulfur. In some embodiments, the leaving group is a carbamate, a carbonate, a thiol, an alcohol, an amino (e.g., an aryl amino) or a phenol group.

In certain embodiments, the linking group L[2] is a covalent bond or a chain of between 1 and 12 atoms in length (e.g., between 1 and 10, 1 and 8, 1 and 6 or 1 and 4 atoms in length). In some cases, L[2] is a chain of between 1 and 12 atoms in length that is linked to an amino leaving group of the puromycin detectable moiety Y (e.g., L[2] has a structure L[3]-X[2] where L[3] is a linking group and X[2] is the amino leaving group, e.g., —NH—, such that upon cleavage of the cleavable bond (CH[2]—X), a moiety is released (e.g., HX-L[3]-NH—Y) that includes both the first leaving group (X), L[3] and —NH—Y. In such cases, the released moiety (e.g., HX-L[3]-NH—Y) may undergo further cleavage or fragmentation (e.g., via an intramolecular cyclization-release) to release the puromycin moiety $H_2N$—Y, a moiety that may be directly or indirectly detected. In some embodiments, L² is a covalent bond, such that upon cleavage of the cleavable bond (CH₂—X), a puromycin moiety is released. When referring to the puromycin detectable moiety that is released it is understood that the leaving group (X and/or X²) and segments of the linker may be attached to the puromycin detectable moiety being described. It is understood that in any of the embodiments described herein that upon cleavage of the cleavable bond of the linker, a cyclization moiety is released that may be directly or indirectly detected, or that may undergo further cleavage/fragmentation (e.g., via an intramolecular cyclization-release) prior to being detected.

In certain instances, the L¹ linker group is selected from one of the following structures:

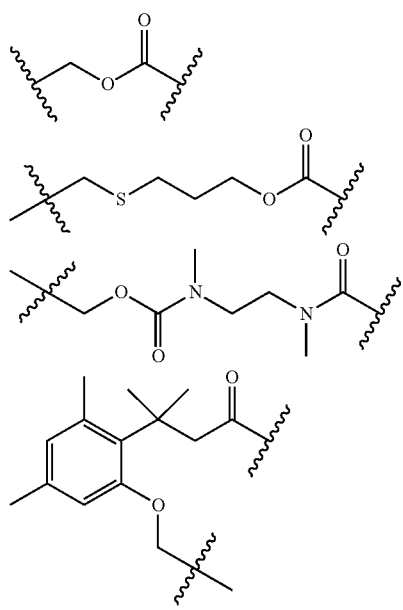

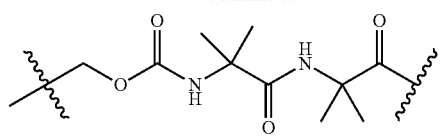

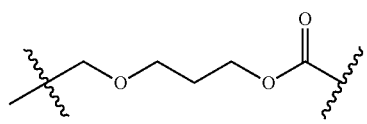

In certain instances of (XI), the probe has one of the following groups including a ROS-sensitive trigger and self immolative linking group, either directly linked to the amino group of the puromycin moiety as shown or linked via a further optional linking group;

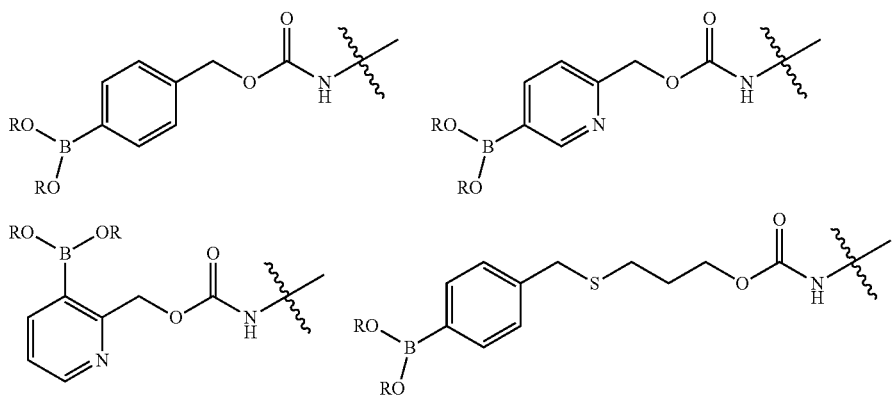

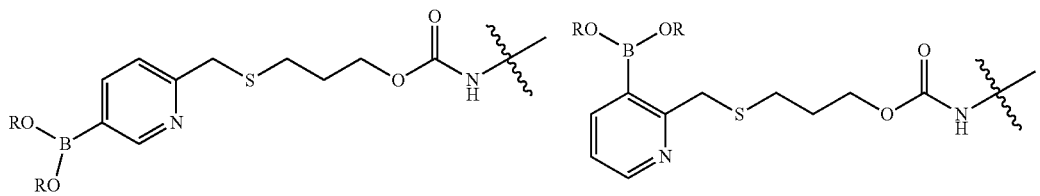

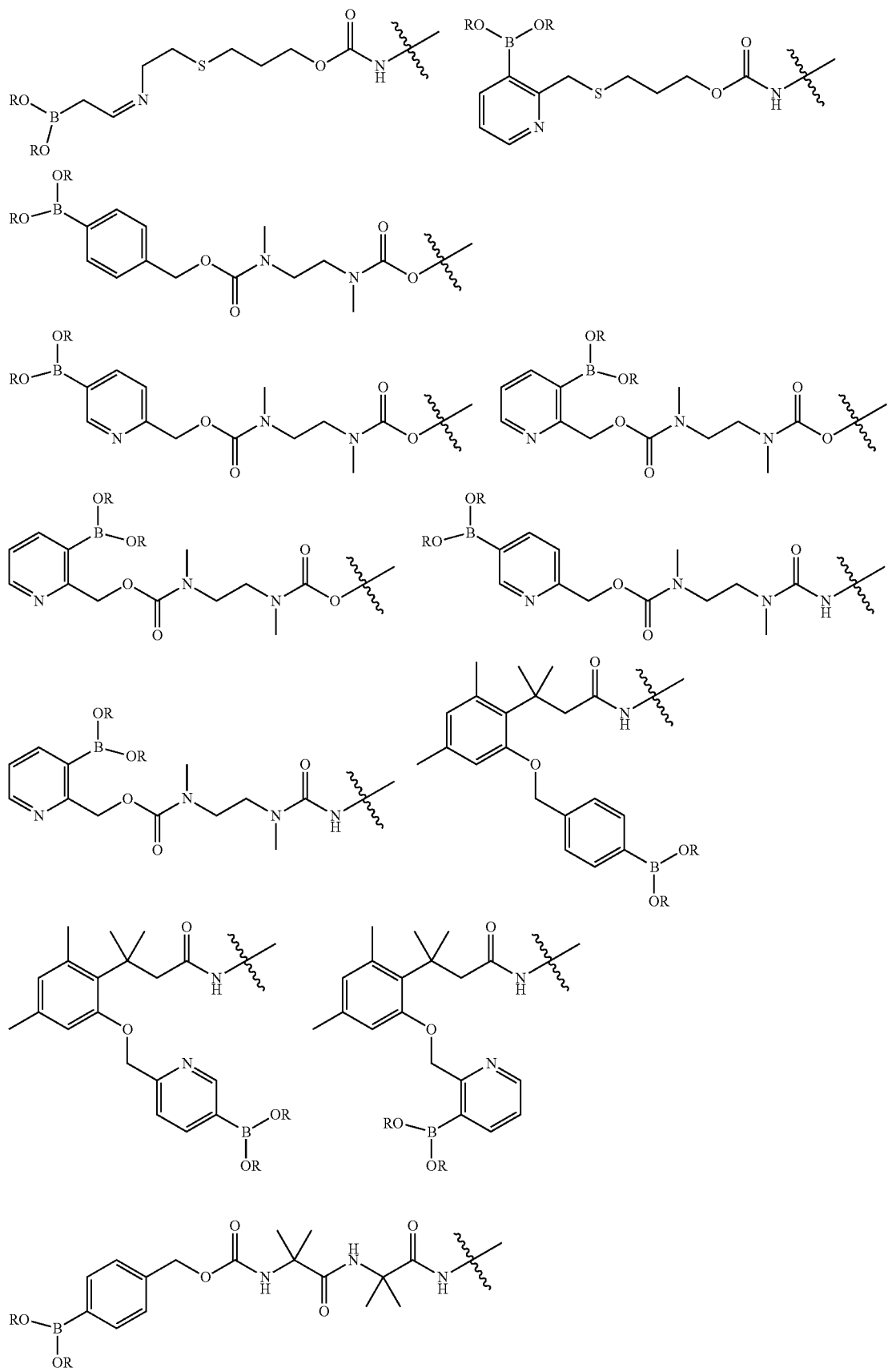

-continued
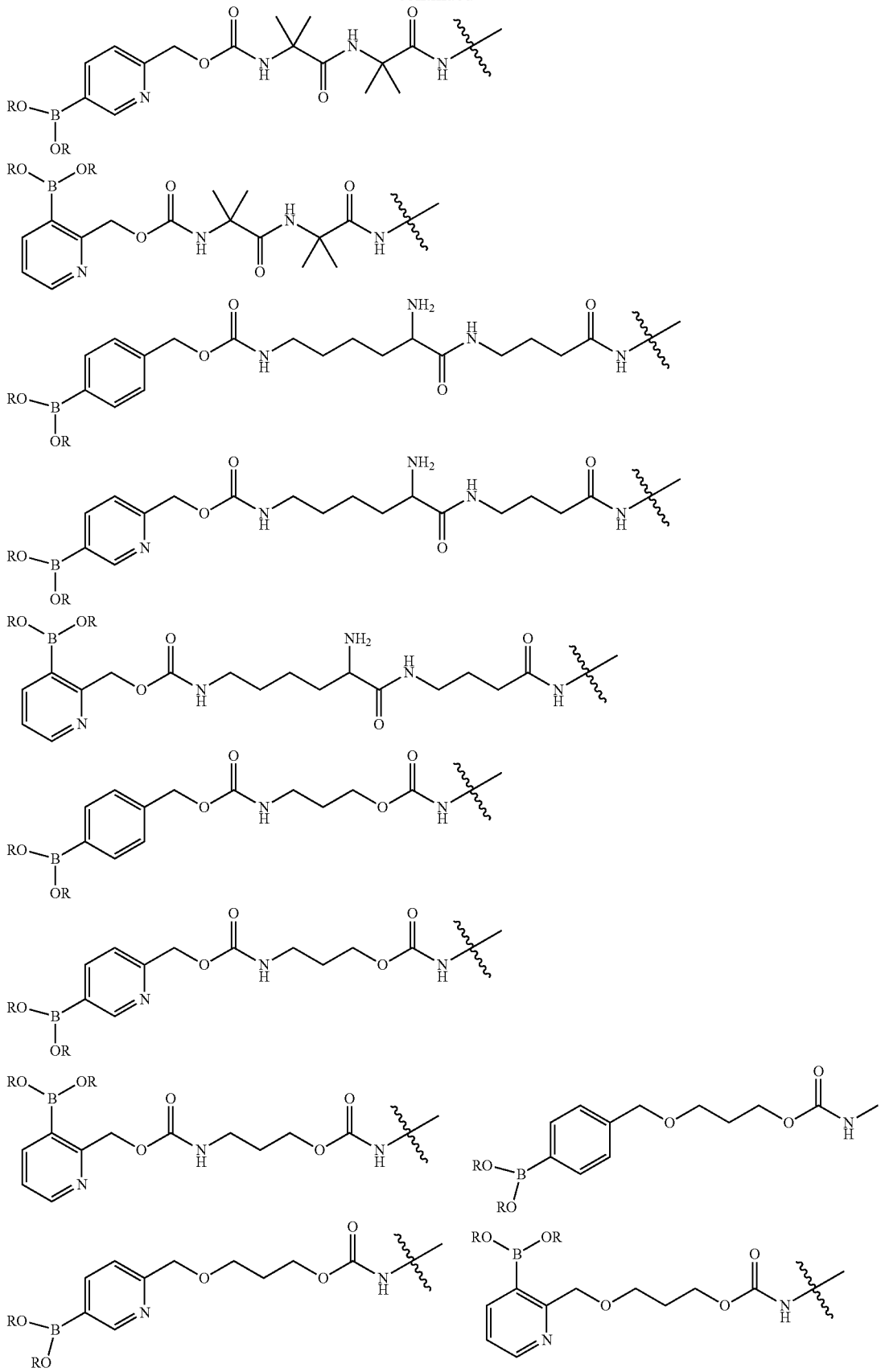

wherein each R is independently selected from hydrogen, alkyl and substituted alkyl; or the two R together form a boronic ester ring or substituted boronic ester ring. In certain embodiments, the two R groups are cyclically linked and selected from the following structures, where both the alkyl fragment and resulting boronic ester are shown below:

nic acid, phosphoryl, phosphonyl group, substituted or unsubstituted aryl, substituted or unsubstituted heteroaryl;

$R^4$, $R^5$, $R^6$ and $R^7$ are independently hydrogen, substituted or unsubstituted alkyl, and substituted or unsubstituted heteroalkyl;

m is integer selected from 1, 2 and 3.

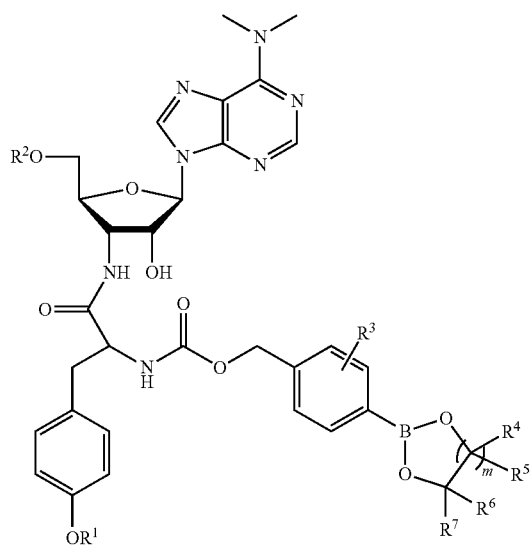

In some instances, the puromycin-based probe for molecular imaging of ROS (e.g., $H_2O_2$) has the formula (V):

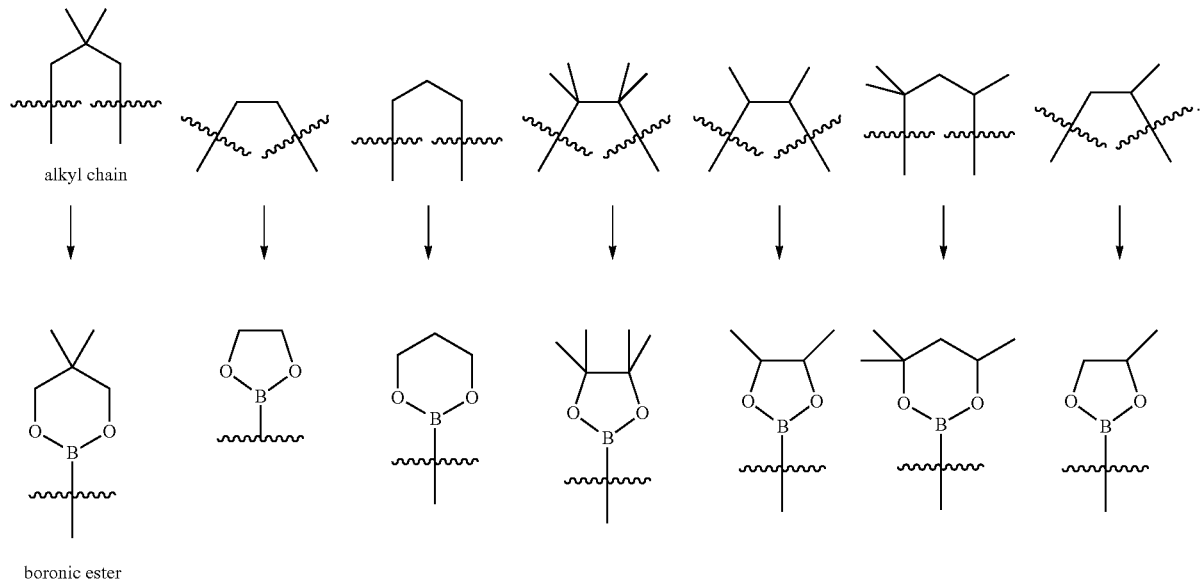

wherein:

$R^1$, $R^2$ and $R^3$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfo- In some embodiments of formula (V), $R^1$ is selected from hydrogen, alkyl, substituted alkyl, substituted or unsubstituted cycloalkyl, substituted or unsubstituted heteroalkyl, alkenyl, substituted alkenyl, alkynyl, substituted alkynyl, alkanoyl, substituted alkanoyl, aroyl, substituted aroyl, heteroaroyl, substituted heteroaroyl, phosphoryl, phosphonyl group, phosphate and sulfonyl. In some embodiments of formula (V), $R^2$ is hydrogen, $C_{1-6}$ alkyl or $C_{1-6}$ substituted alkyl. In some embodiments of formula (V), $R^3$ is hydrogen.

RCS-Responsive Trigger Group

In some instances, the analyte-responsive trigger is RCS-responsive. The subject probes can include a homoallylamine trigger group which is configured for selective reaction in a sample with a RCS of interest. In some embodiments, the probe can selectively react via a 2-aza-Cope rearrangement with a RCS. As used herein, a "homoallylamine trigger group" refers to a chemical group including a substituted homoallylamine (e.g., a group having the general formula $CH_2$=CH—$CR_2$—$CR_2$—NHR, where each R is independently H or any convenient substituent group, e.g., as described herein). In some embodiments, the probes include a homoallylamine trigger group that selectively reacts with a RCS (e.g., formaldehyde) to produce a Schiff base adduct that undergoes further rearrangement and/or reaction to release two products, e.g., an amino product and a keto or aldehyde product (see e.g., Scheme 1). The subject probes take advantage of the resulting rearrangement and cleavage of the homoallylamine trigger group to produce a detectable change in a property of the probe via its conversion to reaction products (e.g., to release a puromycin detectable moiety). In some cases, selective reaction of the probe with a RCS (e.g., formaldehyde) proceeds according to the exemplary reaction set forth in scheme 1.

Scheme 1

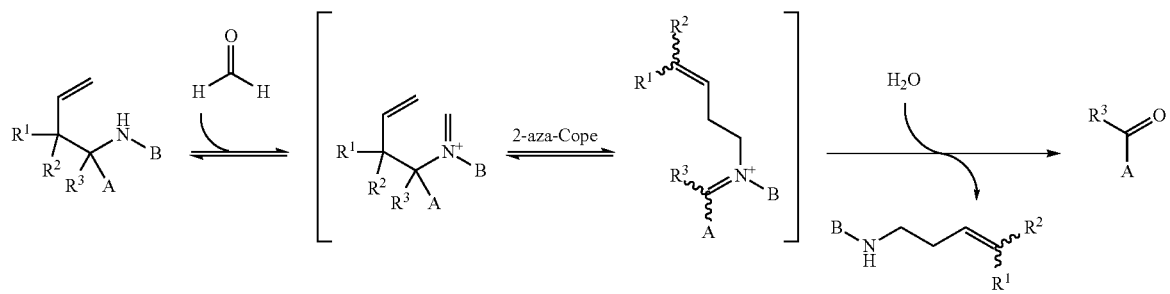

where R$^1$-R$^3$, A and B are any convenient substituent groups, where at least one of A and B includes a puromycin detectable moiety.

It is understood that other configurations of the probes described herein are possible that can also provide for release of a detectable puromycin moiety of the probe in response to reaction of a homoallylamine trigger group with a RCS.

Aspects of the present disclosure include a probe having the following analyte-response trigger group:

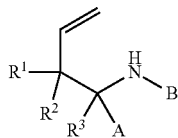

wherein: R$^1$, R$^2$, R$^3$, A and B are each independently selected from hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido; and wherein A comprises a puromycin detectable moiety; and wherein A and B are optionally cyclically linked.

In some instances, the puromycin-based probe has formula (VIII) and finds use in targeted a RCS, such as formaldehyde:

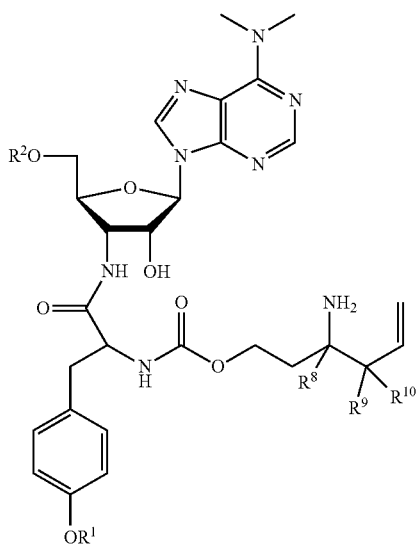

(VIII)

wherein:

R$^1$, R$^2$, R$^8$, R$^9$ and R$^{10}$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

In some embodiments of formula (VIII), R$^1$ is selected from hydrogen, alkyl, substituted alkyl, substituted or unsubstituted cycloalkyl, substituted or unsubstituted heteroalkyl, alkenyl, substituted alkenyl, alkynyl, substituted alkynyl, alkanoyl, substituted alkanoyl, aroyl, substituted aroyl, heteroaroyl, substituted heteroaroyl, phosphoryl, phosphonyl group, phosphate and sulfonyl. In some embodiments of formula (VIII), R$^2$ is hydrogen, C$_{1-6}$ alkyl or C$_{1-6}$ substituted alkyl. In some embodiments of formula (VIII), R$^8$, R$^9$, R$^{10}$ are independently selected from hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido. In some embodiments of formula (VIII), R$^8$, R$^9$, R$^{10}$ are independently selected from hydrogen, an alkyl and a substituted alkyl.

RSS-Responsive Trigger Group

In some instances, the analyte-responsive trigger is RSS-responsive. The subject probes can include an azide group for reacting with a RSS such as hydrogen sulfide. In some cases, the azide group is part of an aryl azide or a heteroaryl azide, where the aryl or heteroaryl ring is optionally further substituted. In certain cases, the RSS-responsive trigger group includes a 4-azido-phenyl group (p-N$_3$-Ph-). The aryl or heteroaryl azide trigger group can undergo H$_2$S-mediated reduction to an amine. The aryl or heteroaryl azide can be linked directly or indirectly to a self-immolative linker (e.g., as described herein). Conversion of the aryl or heteroaryl azide to the corresponding amine can provide for cleavage of a suitably configured labile bond in the attached linker.

In some instances, the puromycin-based probes have the formula (VI) for molecular imaging of a RSS (e.g., $H_2S$):

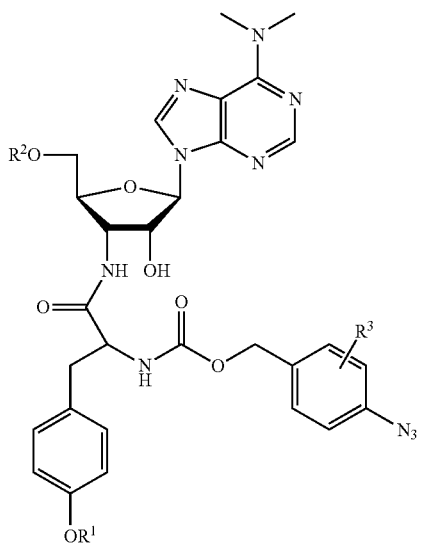

wherein:

$R^1$, $R^2$ and each $R^3$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

In some embodiments of formula (VI), $R^1$ is selected from hydrogen, alkyl, substituted alkyl, substituted or unsubstituted cycloalkyl, substituted or unsubstituted heteroalkyl, alkenyl, substituted alkenyl, alkynyl, substituted alkynyl, alkanoyl, substituted alkanoyl, aroyl, substituted aroyl, heteroaroyl, substituted heteroaroyl, phosphoryl, phosphonyl group, phosphate and sulfonyl. In some embodiments of formula (VI), $R^2$ is hydrogen, $C_{1-6}$ alkyl or $C_{1-6}$ substituted alkyl. In some embodiments of formula (VI), $R^3$ is one or more substituents. In some embodiments of formula (VI), $R^3$ is hydrogen.

Trigger Responsive to ROS Scavenger

In some instances, the analyte-responsive trigger is ROS-scavenger responsive. The subject probes can include an disulfide group for reacting with a ROS scavenger such as glutathione (GSH) or thioredoxin reductase or the like. Glutathione (GSH) is an important antioxidant in plants, animals, fungi, and some bacteria and archaea. Glutathione reduces disulfide bonds to thiols by serving as an electron donor. In some cases, the trigger group includes a disulfide that is configured upon reduction by a ROS scavenger to produce a terminal thiol group capable of intramolecular cyclization to a labile linking group (e.g., a carbamate group) of the self immolative linker to provide for release of the puromycin moiety. In certain cases, the ROS scavenger-responsive trigger group includes a disulfide head group —S—S—R, where R is any convenient substituent such as an alkyl or substituted alkyl. The disulfide can be linked directly to a self-immolative linker (e.g., as described herein). Conversion of the disulfide to a thiol can provide for cleavage of a suitably configured labile bond in the attached linker.

In some instances, the disulfide trigger group has the formula —S—S—$(CH_2CH_2X)_n$—Y wherein n is 0 to 20, X is $C_0$, NH, $CH_2$, O or S; and Y is hydrogen, substituted or unsubstituted alkyl, substituted or unsubstituted cycloalkyl, substituted or unsubstituted heteroalkyl, substituted or unsubstituted heterocycloalkyl, amido, carboxyl, ester, carbonyl, formyl, thio, alkythio, sulfonyl, sulfonic acid, azidyl, nitro, isocyanate-yl, alkenyl, alkynyl, sulfonyl, sulfonic acid, phosphoryl, phosphonyl group, aryl or substituted aryl. In some embodiments, X is O, Y is hydrogen, alkyl or substituted alkyl, and n is 1 to 20, e.g., 1 to 10 or 1 to 6.

In some instances, the puromycin-based probe has formula (VII) and finds use in targeting a ROS scavenger (e.g., GSH):

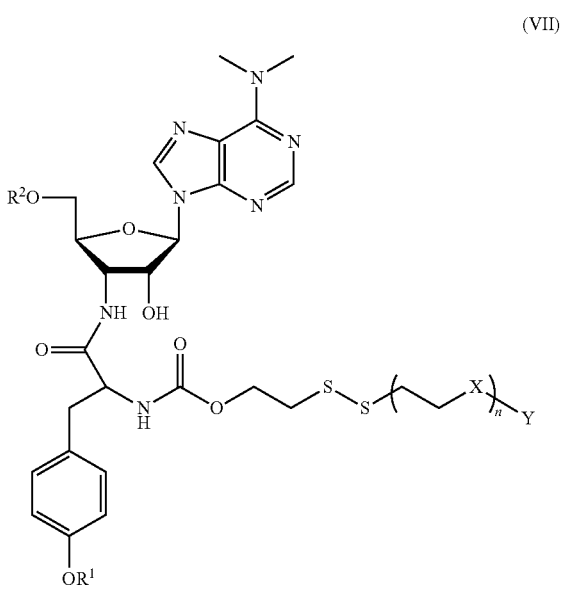

wherein:

$R^1$ and $R^2$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl;

X is $C_0$, NH, $CH_2$, O or S;

Y is hydrogen, substituted or unsubstituted alkyl, substituted or unsubstituted cycloalkyl, substituted or unsubstituted heteroalkyl, substituted or unsubstituted heterocycloalkyl, amido, carboxyl, ester, carbonyl, alkanoyl, substituted alkanoyl, formyl, thio, alkythio, sulfonyl, sulfonic acid, azidyl, nitro, isocyanate-yl, alkenyl, alkynyl, sulfonyl, sulfonic acid, phosphoryl, phosphonyl group, aryl or substituted aryl; and n is integer from 0 to 20 (e.g., 0 to 10, 1 to 10, 1 to 6).

In some embodiments of formula (VII), $R^1$ is selected from hydrogen, alkyl, substituted alkyl, substituted or unsubstituted cycloalkyl, substituted or unsubstituted heteroalkyl, alkenyl, substituted alkenyl, alkynyl, substituted alkynyl, alkanoyl, substituted alkanoyl, aroyl, substituted aroyl, heteroaroyl, substituted heteroaroyl, phosphoryl, phosphonyl group, phosphate and sulfonyl. In some embodiments of formula (VI), $R^2$ is hydrogen, $C_{1-6}$ alkyl or $C_{1-6}$ substituted alkyl. In some embodiments of formula (VII), X is O, Y is hydrogen, alkyl or substituted alkyl, and n is 1 to 20. In some embodiments of formula (VII), $R^1$ is $CH_3$; $R^2$ is H; X is O; Y is acetyl; and n is 1.

cases, the redox-active metal ion is Fe(II). In some cases, the redox-active metal ion is Co(II).

As such, in some instances the trigger group includes a metal ion chelator (Chel) including at least one aryl or heteryl group that is substituted with —$CH_2$—O— where the O atoms is covalently linked to an aryl or heteroaryl ring of a self-immolative linker. In some instances, the trigger has the formula (Chel)-$CH_2O$— where the O atom is covalently linked to, or is a part of a self immolative linker (e.g., as described herein). Any convenient chelating groups capable of chelating a target redox-active metal ion can be adapted for use as a trigger group in the subject probes.

In some embodiments, the puromycin-based probe has formula (IX) for targeting a redox-active metal such as copper(I) ion:

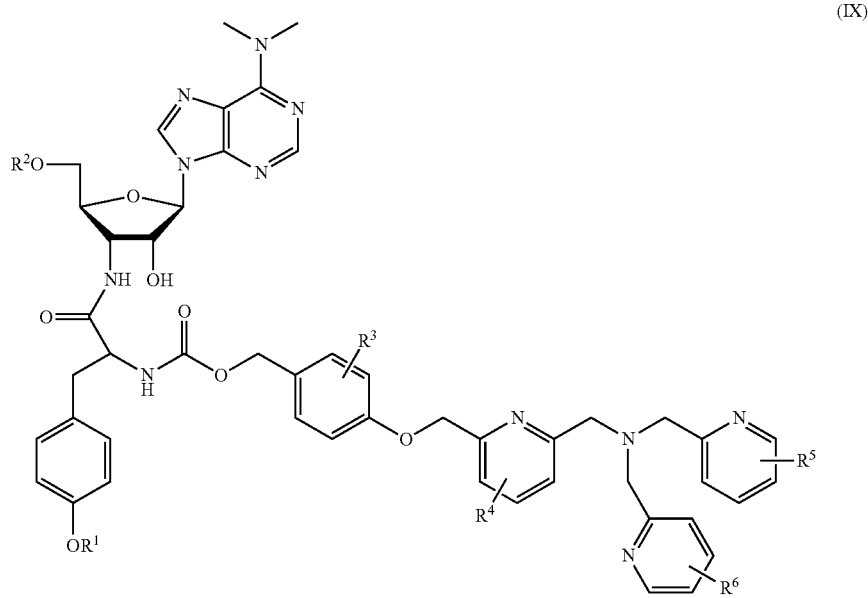

(IX)

Trigger for Redox-Active Metal Ions

In some instances, the analyte-responsive trigger is responsive to a redox-active metal ion. A variety of physiological redox reactions are catalyzed by redox-active metal ions such as iron and copper. The subject probes can include a chelating ligand for a metal ion of interest which is configured adjacent to a redox labile bond of the self-immolative linker. Upon binding of the metal ion analyte, a redox reaction can occur. The redox-active metal ion can be oxidized while an adjacent redox-labile bond, e.g., an aryl ether, can be reduced to result in cleavage of the ether, followed by spontaneous release of the puromycin moiety. In some cases, the redox-active metal ion is Cu(I). In some wherein:

$R^1$, $R^2$, $R^3$, $R^4$, $R^5$ and $R^6$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

In some embodiments, the puromycin-based probe has formula (X) for targeting a redox-active metal such as iron(II) ion:

(X)

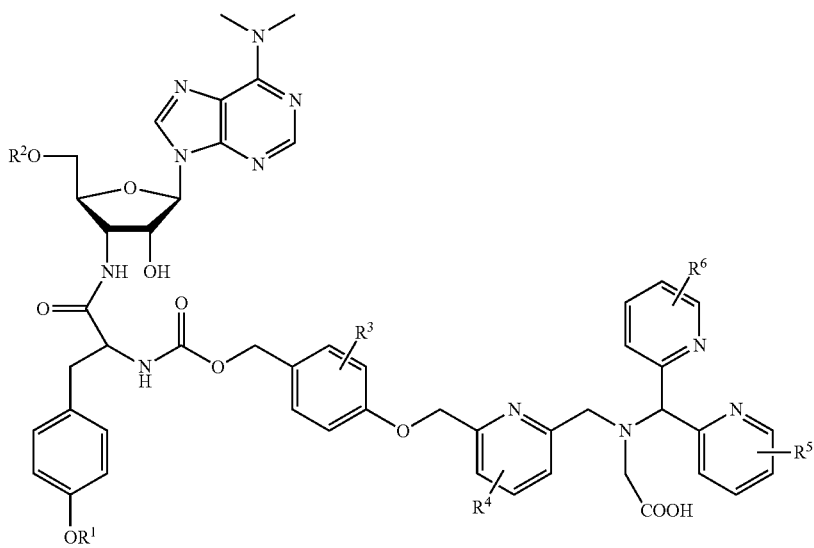

wherein:

$R^1$, $R^2$, $R^3$, $R^4$, $R^5$ and $R^6$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

In some embodiments, the puromycin-based probe has formula (XI) for targeting a redox-active metal such as cobalt(II) ion:

wherein:

$R^1$, $R^2$, $R^3$, $R^4$ and $R^5$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

In some embodiments of formulae (IX)-(XI), $R^1$ is selected from hydrogen, alkyl, substituted alkyl, substituted or unsubstituted cycloalkyl, substituted or unsubstituted (XI)

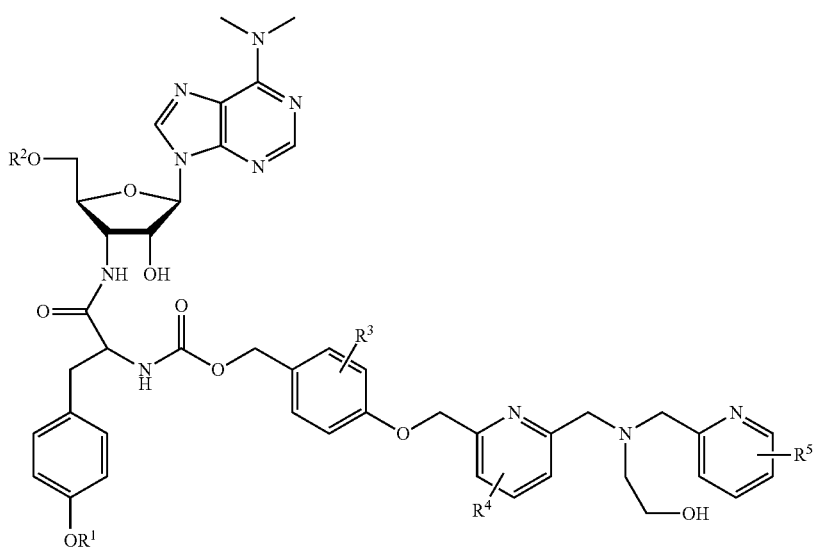

heteroalkyl, alkenyl, substituted alkenyl, alkynyl, substituted alkynyl, alkanoyl, substituted alkanoyl, aroyl, substituted aroyl, heteroaroyl, substituted heteroaroyl, phosphoryl, phosphonyl group, phosphate and sulfonyl. In some embodiments of formulae (IX)-(XI), $R^2$ is hydrogen, $C_{1-6}$ alkyl or $C_{1-6}$ substituted alkyl. In some embodiments of formulae (IX)-(XI), $R^3$ is hydrogen. In some embodiments of formulae (IX)-(XI), $R^4$-$R^6$ are each hydrogen.

Compositions

The present disclosure provides a composition comprising a compound of the present disclosure (e.g., a puromycin-based probe of the present disclosure). In some cases, e.g., where a compound of the present disclosure is to be administered to an individual, a composition of the present disclosure can comprise: a) a compound of the present disclosure (e.g., a puromycin-based probe of the present disclosure); and b) a pharmaceutically acceptable excipient. In some cases, e.g., where a compound of the present disclosure is to be used in an in vitro detection method, a composition of the present disclosure can comprise: a) a compound of the present disclosure (e.g., a puromycin-based probe of the present disclosure); and b) a buffer.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Pharmaceutically acceptable excipients include, e.g., substances required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

Methods of Detecting an Analyte

The present disclosure provides a method of detecting an analyte (e.g., a redox-active analyte) in a biological sample in vitro. The present disclosure provides a method of detecting an analyte (e.g., a redox-active analyte) in a cell, tissue, organ, or fluid in an individual in vivo. A compound of the present disclosure (a puromycin-based probe of the present disclosure) is contacted with a sample in vitro, or introduced into a subject in vivo. The compound reacts with a redox-active analyte (where the redox-active analyte is present in the sample in vitro; or is present in the cell, organ, tissue, or fluid in vivo); the reaction results in release of the P moiety (puromycin or puromycin analog) from the compound, generating free puromycin (or puromycin analog). The free puromycin (or puromycin analog) forms an amide linkage between a polypeptide in the sample (e.g., a nascent polypeptide chain) and the amino acid residue portion (e.g., O-methyl tyrosine portion) of free puromycin, thereby generating a puromycylated polypeptide. The puromycylated polypeptide is detected. The presence of the puromycylated polypeptide indicates the presence in the sample, cell, tissue, organ, or fluid, of the redox-active analyte. Thus, detection of the puromycylated polypeptide provides for detection of the redox-active analyte in the sample, cell, tissue, organ, or fluid.

The method may include contacting the sample of interest with a subject probe (e.g., as described herein). Any convenient method may be used to contact the sample with a probe that selectively reacts with the target analyte (e.g. ROS, RSS, RCS, ROS scavengers and redox-active metal ions) to release a free puromycin molecules which can then incorporate into nascent peptides, immunostained and hence giving rise to detectable change. In some instances, the sample is contacted with the probe under conditions in which probe selectively reacts with target analyte, if present.

The target analyte may be present in the sample at physiologically relevant concentrations. In some cases, for selective reaction of the probe with target analyte, an appropriate solution may be used that maintains the integrity of the probe and any other analytes of interest (e.g., biomolecules) in the sample. The solution may be a balanced salt solution, e.g., normal saline, phosphate buffered saline (PBS), Hank's balanced salt solution, etc., conveniently supplemented with fetal calf serum, human platelet lysate or other factors, in conjunction with an acceptable buffer at low concentration, such as from 5 μM to 50 mM. Convenient buffers include HEPES, phosphate buffers, lactate buffers, etc. Various media are commercially available and may be used according to the nature of the sample, including DMEM, HBSS, DPBS, RPMI, Iscove's medium, etc., frequently supplemented with fetal calf serum or human platelet lysate. The final components of the solution may be selected depending on the components of the sample which are included.

The temperature at which selective reaction of the probe and target analyte takes place may vary, and in some instances may range from 5° C. to 50° C., such as from 10° C. to 40° C., 15° C. to 40° C., 20° C. to 40° C., e.g., 20° C., 25° C., 30° C., 35° C., or 37° C. (e.g., as described above). In some instances, the temperature at which specific reaction takes place is selected to be compatible with the viability of a biological sample and/or the biological activity of an analyte of interest. In certain instances, the temperature is 25° C., 30° C., 35° C., or 37° C. In certain cases, the temperature at which the probe reaction takes place is room temperature (e.g., 25° C.), 30° C., 35° C., or 37° C. Any convenient incubation time for the probe reaction may be selected to allow for the formation of a desirable amount of free puromycin molecules, and in some instances, may be 10 minutes (min) or more, 30 min or more, 1 hour or more, 2 hours or more, 6 hours or more, 12 hours or more, or even 24 hours or more.

The subject methods may be performed in a variety of biological samples. As used herein, the term "a biological sample" refers to a whole organism or a subset of its tissues, cells or component parts (e.g. body fluids, including, but not limited to, blood, serum, plasma, bronchoalveolar lavage, mucus, lymphatic fluid, synovial fluid, saliva, cerebrospinal fluid, amniotic fluid, amniotic cord blood, urine, tears, vaginal fluid, and semen). A "biological sample" can also refer to a homogenate, lysate, extract or tissue sections prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms. In certain embodiments, cells include prokaryotic cells, such as from bacteria. In other embodiments, cells include eukaryotic cells, such as cells obtained from biological samples from animals, plants, or fungi. The sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the biological sample is an acellular in vitro biological sample. In some cases, the biological sample is an in vitro biological sample, and comprises cells.

In some embodiments, the biological sample includes a cell. A variety of cells may be used in conjunction with the subject methods. Target cells of interest include, but are not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus-infected cells (e.g., HIV-infected cells), natural killer (NK) cells, macrophages, monocytes, fibroblasts, epithelial cells, endothelial cells, and erythroid cells. Target cells of interest include cells that have a convenient cell surface marker or antigen that may be captured by a convenient specific binding member or conjugates thereof. Target cells include cells that are abnormal, e.g., diseased cells. Target cells include, e.g., cancer cells, virus-infected cells, and the like.

Aspects of the subject methods include detecting the generated puromycin molecules formed from the reaction between the probe and target analyte, thereby providing for detection of the analyte in the sample. In some embodiments, the detecting comprises fluorescently imaging the sample. Detection methods of interest include, but are not limited to, fluorescence microscopy, fluorescence spectroscopy, flow cytometry, absorbance spectroscopy. Detection may be achieved via a detectable moiety-functionalized secondary antibody that can specifically recognize primary α-puromycin antibody, or by secondary antibody which can couple with horseradish peroxidase, beta-galactosidase, and luciferase, and the like, for giving rise to measurable change. The detectable change can also be amplified by signal amplification systems (e.g., biotin-streptavidin technology, protein-A and protein-G mediated technology, or nucleic acid probe/anti-nucleic acid probes, and the like).

In some embodiments, the detection includes detecting a cell in a flow cytometer. Such a step may include exciting a fluorescent dye-secondary antibody with one or more lasers at an interrogation point of the flow cytometer, and subsequently detecting fluorescence emission from the dye using one or more optical detectors. It may be desirable, in addition to detecting the particle (e.g., cell), to determine the number of particles (e.g., cells) separated, or utilizing one or components of the methods for the purpose of sorting the particles. Accordingly, in some embodiments, the methods further include counting, sorting, or counting and sorting the labeled particle (e.g., target cell).

In some embodiments, the method further comprises analyzing the level of target analyte in the sample. Any convenient methods may be used to analyze the level of target analyte in the sample.

In certain embodiments, the probes may be used as an assay reagent. Assays using detectable moieties such as fluorophores, chromophores and luminophores are well known in the art. Such assays may be adapted for use in the subject methods for analyzing biological mechanisms for interest. In some cases, a sample of interest (e.g., cells) is contacted with a subject probe, then a change in an optical property is detected. The presence of a target analyte (e.g., $H_2O_2$) in the sample is determined by the addition of the probe reagent.

In some instances, the subject methods are bioorthogonal such that the subject probe can selectively react with target analyte in the presence of the endogenous components of any convenient biological sample. In some instances, $H_2O_2$ that is detected according to the subject methods is produced endogenously in a sample by paraquat incubation. In some instances, $H_2O_2$ that is detected according to the subject methods is produced endogenously in a sample by EGF stimulation. In some instance, $H_2S$ that is detected according to the subject methods is produced endogenously in a sample by cysteine incubation. In some instance, glutathione that is detected according to the subject methods is found to show inhibition in endogenous production in a sample by buthionine sulfoximine (BSO) incubation.

As such, the probes of the present disclosure are useful in in situ methods of analyzing cells. Methods of performing in situ analysis of cells using detectable moieties-antibody conjugates by immunostaining are known in the art and may be adapted for use in the subject methods.

In some cases, a detection method of the present disclosure is an in vitro method. Thus, the present disclosure provides a method of detecting an analyte (e.g., a redox-active analyte) in a biological sample in vitro. The method comprises: a) contacting the sample with a puromycin-based probe of the present disclosure, wherein, in the presence of the redox-active analyte, moiety P is released from the puromycin-based probe and reacts with a nascent polypeptide present in the sample, thereby forming a puromycylated polypeptide; and b) detecting the puromycylated polypeptide, wherein detection of the puromycylated polypeptide provides for detection of the redox-active analyte in the sample.

In some embodiments, the probes may be used as histochemical probes for detecting level of target analytes in sample. In some cases, the probes are administrated to the subject and the tissues from the subject are harvested afterward. In some cases, the level of target analyte in the tissue samples can then be detected by dot blot of homogenized tissues in RIPA buffer, through immunostaining of primary α-puromycin antibody and subsequently detectable moiety-secondary antibody, and then imaged. In some cases, the tissue sample can be fixed, cyroprotected and sectioned. The tissue sections can then be immunostained by primary α-puromycin antibody and detectable moiety-secondary antibody, and then imaged for detecting the level of target analyte in the sample.

Any convenient concentration of probe in the sample may be achieved in the subject methods. In some instances, the concentration of probe may be between 0.1 µM and 100 mM, such as between 0.1 µM and 10 µM, between 0.5 µM and 5 µM, between 5 µM and 10 µM, between 10 µM and 100 µM, between 100 µM and 1 mM, between 1 mM and 10 mM or between 10 mM and 100 mM. In certain cases, the solution is an aqueous solution.

In some cases, a detection method of the present disclosure is an in vivo method. Thus, the present disclosure provides a method of detecting a redox-active analyte in a cell, tissue, organ, or fluid in a living subject, the method comprising: a) administering to the subject puromycin-based probe of the present disclosure, wherein, in the presence of the redox-active analyte, moiety P is released from the puromycin-based probe and reacts with a nascent polypeptide in the subject, thereby forming a puromycylated polypeptide; and b) detecting the puromycylated polypeptide, wherein detection of the puromycylated polypeptide provides for detection of the redox-active analyte in the subject.

As summarized above, aspects of the present disclosure include methods of detecting analyte in a cell, tissue, organ or fluid by the puromycin-based probes. The method may comprise administering the probe (e.g., as described herein) to the subject thereby selectively reacting the probe with the target analyte in the sample to release free puromycin, thus allowing puromycin to incorporate into nascent peptides and hence being detected by immunostaining.

Aspects of the method include detecting the puromycin-incorporated peptides in cell, tissue, organ or fluid, thereby providing for detection of the target analyte. Any convenient methods of detecting (e.g., as described herein) may be utilized in the subject methods to detect the puromycin-incorporated peptides, which are generated from the reaction between puromycin-based probes and target analytes, in vivo, ex vivo or in vitro in a sample taken from the subject. In some cases, the subject is human. In some cases, the subject is a mammal. In some cases, the subject is a non-human animal, such as a mouse, rat, cat, dog, monkey, etc.

Administration of the subject probes may be systemic or local. In certain embodiments administration to a subject will result in systemic release of a compound of the invention (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. For example, the probes can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Kits

The present disclosure provides a kit for carrying out a detection method of the present disclosure. A kit of the present disclosure includes a compound of the present disclosure (a puromycin-based probe of the present disclosure), and may include one or more additional components.

In some cases, a kit of the present disclosure comprises: a) a compound of the present disclosure (a puromycin-based probe of the present disclosure); and b) an anti-puromycin antibody that specifically binds to puromycin in a puromycylated polypeptide. An anti-puromycin antibody suitable for use does not substantially bind to the P moiety (puromycin or puromycin analog) of a probe compound of the present disclosure.

In some cases, the antibody comprises a detectable label. For example, in some cases, the antibody comprises a fluorophore. In some cases, the antibody comprises a chromophore. In some cases, the antibody comprises a luminophore. The antibody can comprise a radioisotope. The antibody can comprise an enzyme that, when reacted with a substrate, generates a colored product, a luminescent product, a fluorescent product, etc.

A kit of the present disclosure can include additional components such as: a buffer; a protease inhibitor; one or more reagents for developing a detectable signal; and the like.

The components of the kit can be in the same or in separate containers. A kit can comprise instructions for use, where the instructions can be in printed form or electronic form.

Definitions

The term "cleavable linker group" refers to a linker that can be selectively cleaved to produce two products. Application of suitable cleavage conditions to a molecule containing a cleavable linker that is cleaved by the cleavage conditions will produce two byproducts. A cleavable linker of the present invention is stable, e.g. to physiological conditions, until the molecule is contacted with a cleavage-inducing stimulus, such as a cleavage-inducing analtyte (e.g., a reactive oxygen species).

As used herein, the term "immunostaining" refers to antibody-based method to bind to epitope in the sample. In one embodiment, the incorporated puromycin in sample is immunostained by primary α-puromycin antibody and subsequently by detectable moiety-functionalized secondary antibody.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorophore (e.g., a fluorescent protein; a fluorescent dye), a chromophore, a luminophore, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

Unless otherwise stated or required, each of the compound structures referred to in the invention include conjugate acids and bases having the same structure, crystalline and amorphous forms of those compounds, pharmaceutically acceptable salts, and prodrugs. This includes, for example, polymorphs, solvates, hydrates, unsolvated polymorphs (including anhydrates), and phosphorylated and unphosphorylated forms of the compounds.

The term "alkenyl" refers to a monovalent linear or branched chain group of one to twelve carbon atoms, and such as 1 to 6 carbon atoms, or 1 to 5, or 1 to 4, or 1 to 3 carbon atoms, derived from a straight or branched chain hydrocarbon (hydrocarbyl) containing at least one carbon-carbon double bond.

The term "alkoxy" refers to an alkyl group attached to the parent molecular moiety through an oxygen atom.

The term "alkyl" refers to a monovalent saturated aliphatic hydrocarbyl group having from 1 to 12 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "alkynyl" refers to a straight or branched chain hydrocarbyl group of one to twelve carbon atoms, and such as 1 to 6 carbon atoms, or 1 to 5, or 1 to 4, or 1 to 3 carbon atoms, containing at least one carbon-carbon triple bond.

The term "amino" refers to —$NR^aR^b$, wherein $R^a$ and $R^b$ are hydrogen, alkanoyl, alkenyl, alkoxyalkyl, alkoxyalkoxyalkyl, alkoxycarbonyl, alkyl, alkylaminoalkyl, alkylaminocarbonylalkyl, aryl, arylalkyl, cycloalkyl, (cycloalkyl)alkyl, cycloalkylcarbonyl, haloalkanoyl, haloalkyl, (heterocycle)alkyl, heterocyclecarbonyl, hydroxyalkyl, a nitrogen protecting group, —C(NH)NH$_2$, or —C(O)$NR^cR^d$, where $R^c$ and $R^d$ are hydrogen, alkyl, aryl, heteroaryl, carbocycle or heterocycle; wherein the aryl; the aryl part of the arylalkyl; the cycloalkyl; the cycloalkyl part of the (cycloalkyl)alkyl and the cycloalkylcarbonyl; and the heterocycle part of the (heterocycle)alkyl and the heterocyclecarbonyl can be optionally substituted with one, two, three, four, or five substituents independently selected from the group consisting of alkanoyl, alkoxy, alkyl, cyano, halo, haloalkoxy, haloalkyl, hydroxy, and nitro.

The terms "Aryl" or "Ar" refer to a monovalent aromatic carbocyclic group of from 6 to 18 carbon atoms having a single ring (such as is present in a phenyl group) or a ring system having multiple condensed rings, e.g., a bicyclic fused ring system or a tricyclic fused ring system (examples of such aromatic ring systems include naphthyl, anthryl and indanyl), which condensed rings may or may not be aromatic, provided that the point of attachment is through an atom of an aromatic ring. This term includes, by way of example, phenyl and naphthyl. Bicyclic fused ring systems are exemplified by a phenyl group fused to a cycloalkyl group as defined herein, a cycloalkenyl group as defined herein, or another phenyl group. Tricyclic fused ring systems are exemplified by a bicyclic fused ring system fused to a cycloalkyl group as defined herein, a cycloalkenyl group as defined herein, or another phenyl group. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocylooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO2-aryl, —SO$_2$-heteroaryl and trihalomethyl.

The term "arylalkoxy" refers an aryl group attached to the parent molecular moiety through an alkoxy group.

The term "arylalkyl" refers an aryl group attached to the parent molecular moiety through an alkyl group.

The term "aryloxy" refers to an aryl group attached to the parent molecular moiety through an oxygen atom.

The term "aryloxyalkoxy" refers an aryloxy group attached to the parent molecular moiety through an alkoxy group.

The term "aryloxyalkyl" refers to an aryloxy group attached to the parent molecular moiety through an alkyl group.

The term $C_{1-n}$alkyl linker where n is an integer of 1 to 100, e.g., n is 2, 3, 4, 5, 6, or more, refers to a divalent alkyl linker that connects two groups and has a backbone of "n" atoms in length. The divalent alkyl linker is optionally substituted.

The terms "carbocycle" and "carbocyclic" refer to a saturated or unsaturated group having a single ring or multiple condensed rings, including fused, bridged and spiro ring systems, and having from 3 to 20 ring carbon atoms. In fused ring systems, one or more of the rings can be cycloalkyl or aryl, provided that the point of attachment is through the non-aromatic ring.

The term "carbonyloxy" refers to an alkanoyl group attached to the parent molecular moiety through an oxygen atom.

The terms "carboxyl", "carboxy" or "carboxylate" refer to —CO$_2$H or salts thereof.

The term "carboxyalkyl" refers to a carboxy group attached to the parent molecular moiety through an alkyl group.

"Cyano" or "nitrile" refers to the group —CN.

The term "cycloalkenyl" refers to non-aromatic cyclic alkyl groups of from 3 to 10 carbon atoms having single or multiple rings and having at least one double bond and preferably from 1 to 2 double bonds.

The term "cycloalkenylalkyl" refers to a cycloalkenyl group attached to the parent molecular moiety through an alkyl group.

The term "cycloalkyl" refers to a saturated carbocyclic ring system having three to twelve carbon atoms and one to three rings including fused, bridged, and spiro ring systems. Examples of cycloalkyl groups include cyclopropyl, cyclobutyl, cyclopentyl, cyclooctyl, bicyclo(3.1.1)heptyl, adamantyl, and the like. The cycloalkyl groups of this invention can be optionally substituted with one, two, three, four, or five substituents independently selected from alkoxy, alkoxycarbonyl, alkyl, aminoalkyl, arylalkoxy, aryloxy, arylsulfanyl, halo, haloalkoxy, haloalkyl and hydroxy, where the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl and hydroxy.

The term "cycloalkylalkoxy" refers to a cycloalkyl group attached to the parent molecular moiety through an alkoxy group.

The term "cycloalkylalkyl" refers to a cycloalkyl group attached to the parent molecular moiety through an alkyl group.

The term "cycloalkylcarbonyl" refers to a cycloalkyl group attached to the parent molecular moiety through a carbonyl group (—CO—).

The term "cycloalkyloxy" refers to a cycloalkyl group attached to the parent molecular moiety through an oxygen atom.

The term "dialkylamino" refers to —N(R)$_2$, wherein each R is alkyl.

The term "haloalkoxy" refers to an alkoxy group substituted by one, two, three, or four halogen atoms.

The term "haloalkyl" refers to an alkyl group substituted by one, two, three, or four halogen atoms.

"Halo" or "halogen" refers to fluoro, chloro, bromo, and iodo.

"Heteroaryl" refers to an aromatic group of from 1 to 15 carbon atoms, such as from 1 to 10 carbon atoms, and 1 to 10 heteroatoms selected from oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, SO-heteroaryl, SO$_2$-alkyl, —SO$_2$-substituted alkyl, —SO$_2$-aryl and —SO$_2$-heteroaryl, and trihalomethyl.

The term "heteroarylalkyl" refers a heteroaryl group attached to the parent molecular moiety through an alkyl group.

"Heterocycle" "heterocyclic" and "heterocyclyl" refer to a saturated or unsaturated group having a single ring or multiple condensed rings, including fused, bridged and spiro ring systems, and having from 3 to 20 ring atoms, including 1 to 10 heteroatoms. These ring heteroatoms are selected from nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties. When the heterocycle is saturated it may be referred to as a "heterocycloalkyl".

The term "hydroxyalkyl" refers to a hydroxy group attached to the parent molecular moiety through an alkyl group.

Hydroxy" or "hydroxyl" refers to the group —OH.

The term "linker" or "linkage" refers to a linking moiety that connects at least two groups and has a backbone of 100 atoms or less in length between the at least two groups. A linker may be a covalent bond that connects two groups or a group having a backbone of between 1 and 100 atoms in length, for example a backbone of 1, 2, 3, 4, 5, 6, 8, 10, 12, 14, 16, 18 or 20 carbon atoms in length, where the linker may be linear, branched, cyclic or a single atom. A linker that is branched can connect three groups (i.e., trivalent). In certain cases, one, two, three, four or five or more carbon atoms of a linker backbone may be optionally substituted with a sulfur, nitrogen or oxygen heteroatom. The bonds between backbone atoms may be saturated or unsaturated, where usually not more than one, two, or three unsaturated bonds will be present in a linker backbone. The linker may include one or more substituent groups, for example an alkyl, aryl, heteroaryl or alkenyl group. A linker may include, without limitations, ethylene glycol or poly(ethylene glycol) units, ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heteroaryl, a heterocycle or a cycloalkyl group, where 2 or more atoms, e.g., 2, 3 or 4 atoms, of the cyclic group are included in the backbone. A linker may be cleavable or non-cleavable.

The term "monoalkylamino" refers to —NHR, where R is alkyl.

"Nitro" refers to the group —NO$_2$.

In addition to the disclosure herein, the term "substituted" when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{71}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O) NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, $-NR^{80}R^{80}$ is meant to include $-NH_2$, $-NH$-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, $-R^{60}$, halo, $-O^-M^+$, $-OR^{70}$, $-SR^{70}$, $-S^-M^+$, $-NR^{80}R^{80}$, trihalomethyl, $-CF_3$, $-CN$, $-OCN$, $-SCN$, $-NO$, $-NO_2$, $-N_3$, $-SO_2R^{70}$, $-SO_3M^+$, $-SO_3R^{70}$, $-OSO_2R^{70}$, $-OSO_3^-M^+$, $-OSO_3R^{70}$, $-PO_3^{-2}(M^+)_2$, $-P(O)(OR^{70})O^-M^+$, $-P(O)(OR^{70})_2$, $-C(O)R^{70}$, $-C(S)R^{70}$, $-C(NR^{70})R^{70}$, $-CO_2M^+$, $-CO_2R^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OCO_2^-M^+$, $-OCO_2R^{70}$, $-OC(S)OR^{70}$, $-NR^{70}C(O)R^{70}$, $-NR^{70}C(S)R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not $-O^-M^+$, $-OR^{70}$, $-SR^{70}$, or $-S^-M^+$.

In addition to the groups disclosed with respect to the individual terms herein, substituent groups for hydrogens on nitrogen atoms in "substituted" heteroalkyl and cycloheteroalkyl groups are, unless otherwise specified, $-R^{60}$, $-O^-M^+$, $-OR^{70}$, $-SR^{70}$, $-S^-M^+$, $-NR^{80}R^{80}$, trihalomethyl, $-CF_3$, $-CN$, $-NO$, $-NO_2$, $-S(O)_2R^{70}$, $-S(O)_2O^-M^+$, $-S(O)_2OR^{70}$, $-OS(O)_2R^{70}$, $-OS(O)_2O^-M^+$, $-OS(O)_2OR^{70}$, $-P(O)(O^-)_2(M^+)_2$, $-P(O)(OR^{70})O^-M^+$, $-P(O)(OR^{70})(OR^{70})$, $-C(O)R^{70}$, $-C(S)R^{70}$, $-C(NR^{70})R^{70}$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O)OR^{70}$, $-OC(S)OR^{70}$, $-NR^{70}C(O)R^{70}$, $-NR^{70}C(S)R^{70}$, $-NR^{70}C(O)OR^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "substituted alkoxy" refers to a substituted alkyl group attached to the parent molecular moiety through an oxygen atom.

The term "substituted alkyl" refers to an alkyl group where one or more carbon atoms in the alkyl chain have been optionally replaced with a heteroatom such as O—, N—, S—, $-S(O)_n-$ (where n is 0 to 2), —NR— (where R is hydrogen or alkyl) and having from 1 to 5 substituents selected from alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, SO$_2$-heteroaryl and $-NR^aR^b$, where $R^a$ and $R^b$ may be the same or different and are chosen from hydrogen, optionally substituted alkyl, cycloalkyl, alkenyl, cycloalkenyl, alkynyl, aryl, heteroaryl and heterocyclic.

The terms "sulfonate" or "sulfonic acid" refer to —SO$_3$H or salts thereof.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

In some embodiments, the subject compounds, are provided in the form of salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

Except where otherwise stated or required, other terms used in the specification have their ordinary meaning.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-51 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A compound of formula (I):

$$P\text{-}L\text{-}T \qquad (I)$$

wherein:
P is a puromycin detectable moiety;
L is a self-immolative linker; and
T is an analyte-responsive group configured to trigger cleavage of L and release P upon contact with a target analyte.

Aspect 2. The compound of aspect 1, wherein P is of formula (II):

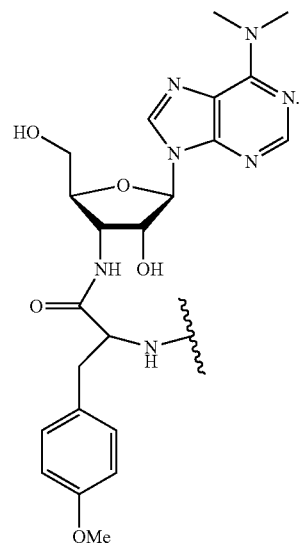

(II)

wherein:

n is 1 or 2;

$R^{11}$ and $R^{12}$ are each independently hydrogen, alkyl or substituted alkyl;

$R^2$, each $R^{13}$ and $R^{14}$ are each independently hydrogen, $C_{1-6}$ alkyl or $C_{1-6}$ substituted alkyl;

each $R^{15}$ is independently selected from alkyl, substituted alkyl, aryl, substituted aryl, heteroaryl, substituted heteroaryl, aryl-alkyl, substituted aryl-alkyl, heteroaryl-alkyl and substituted heteroaryl-alkyl.

Aspect 3. The compound of aspect 1 or 2, wherein the puromycin detectable moiety is:

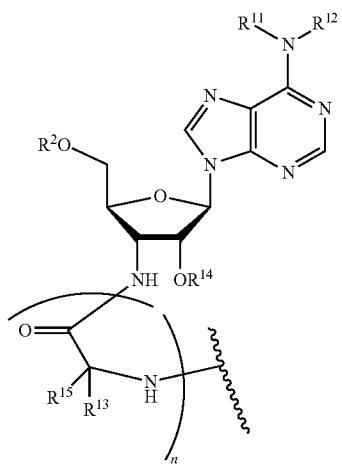

Aspect 4. The compound of any one of aspects 1-3, wherein L comprises one or more of the following linking groups:

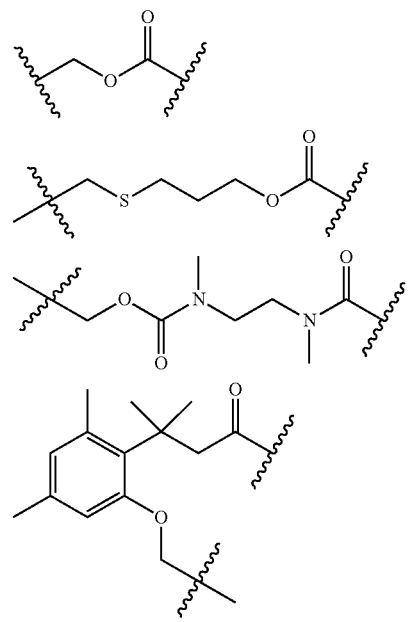

-continued

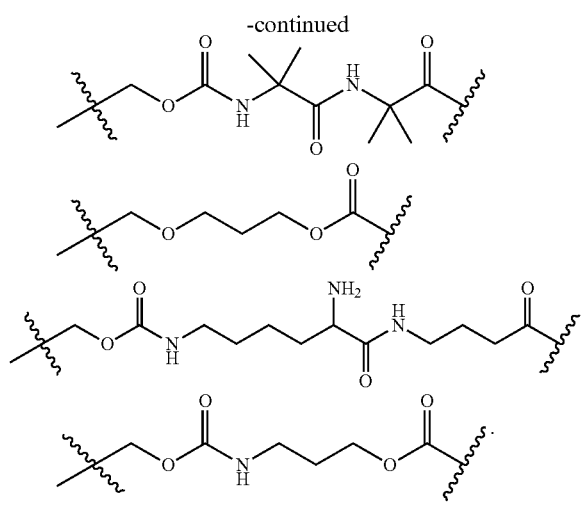

Aspect 5. The compound of any one of aspects 1-4, wherein T comprises a ROS-responsive trigger group, a RCS-responsive trigger group, a RSS-responsive trigger group, a ROS scavenger-responsive trigger group or a trigger group for a redox-active metal ion.

Aspect 6. The compound of any one of aspects 1-5, wherein T comprises:

a) a ROS-responsive trigger group selected from the following:

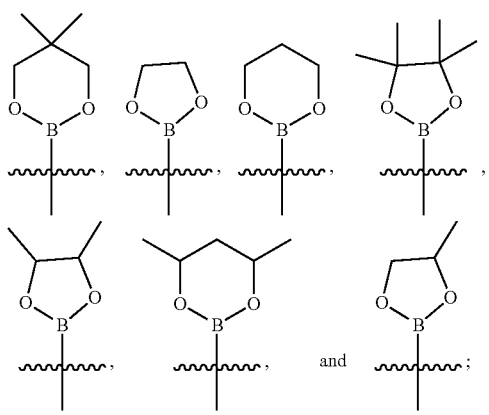

b) a RCS-responsive trigger group of the formula:

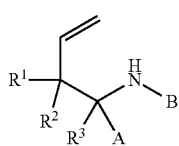

wherein:
R$^1$, R$^2$, R$^3$, A and B are each independently selected from hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido; and wherein A is linked to the puromycin detectable moiety; and wherein A and B are optionally cyclically linked;

c) a RSS-responsive trigger group that comprises an aryl azide or a heteroaryl azide;

d) a ROS scavenger-responsive trigger group that comprises a disulfide group of the formula:

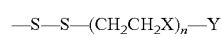

wherein:
n is 0 to 20;
X is C$_0$, NH, CH$_2$, O or S; and
Y is hydrogen, substituted or unsubstituted alkyl, substituted or unsubstituted cycloalkyl, substituted or unsubstituted heteroalkyl, substituted or unsubstituted heterocycloalkyl, amido, carboxyl, ester, carbonyl, formyl, thio, alkythio, sulfonyl, sulfonic acid, azidyl, nitro, isocyanate-yl, alkenyl, alkynyl, sulfonyl, sulfonic acid, phosphoryl, phosphonyl group, aryl or substituted aryl; or e) an analyte-responsive trigger group for a redox-active metal ion having the formula:

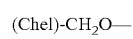

wherein: (Chel) is a metal ion chelator for the redox-active metal ion.

Aspect 7. The compound of any one of aspects 1-6, wherein the compound is of the formula:

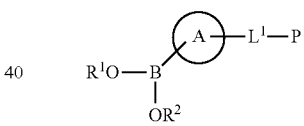

wherein:
P is the puromycin detectable moiety;
R$^1$ and R$^2$ are independently selected from hydrogen, alkyl and substituted alkyl; or R$^1$ and R$^2$ together form a boronic ester ring or substituted boronic ester ring;
A ring is selected from aryl, substituted aryl, heteroaryl, and substituted heteroaryl; and
L$^1$ is cleavable linker group that provides for release of Y upon reaction of the —B(OR$^1$)(OR$^2$) group with a reactive oxygen species (ROS).

Aspect 8. The compound of any one of aspects 1-7, wherein the compound comprises one of the following groups masking the alpha-amino group of the puromycin detectable moiety:

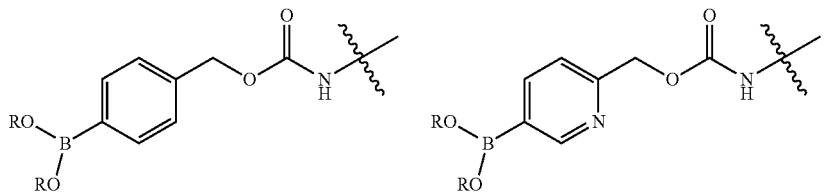

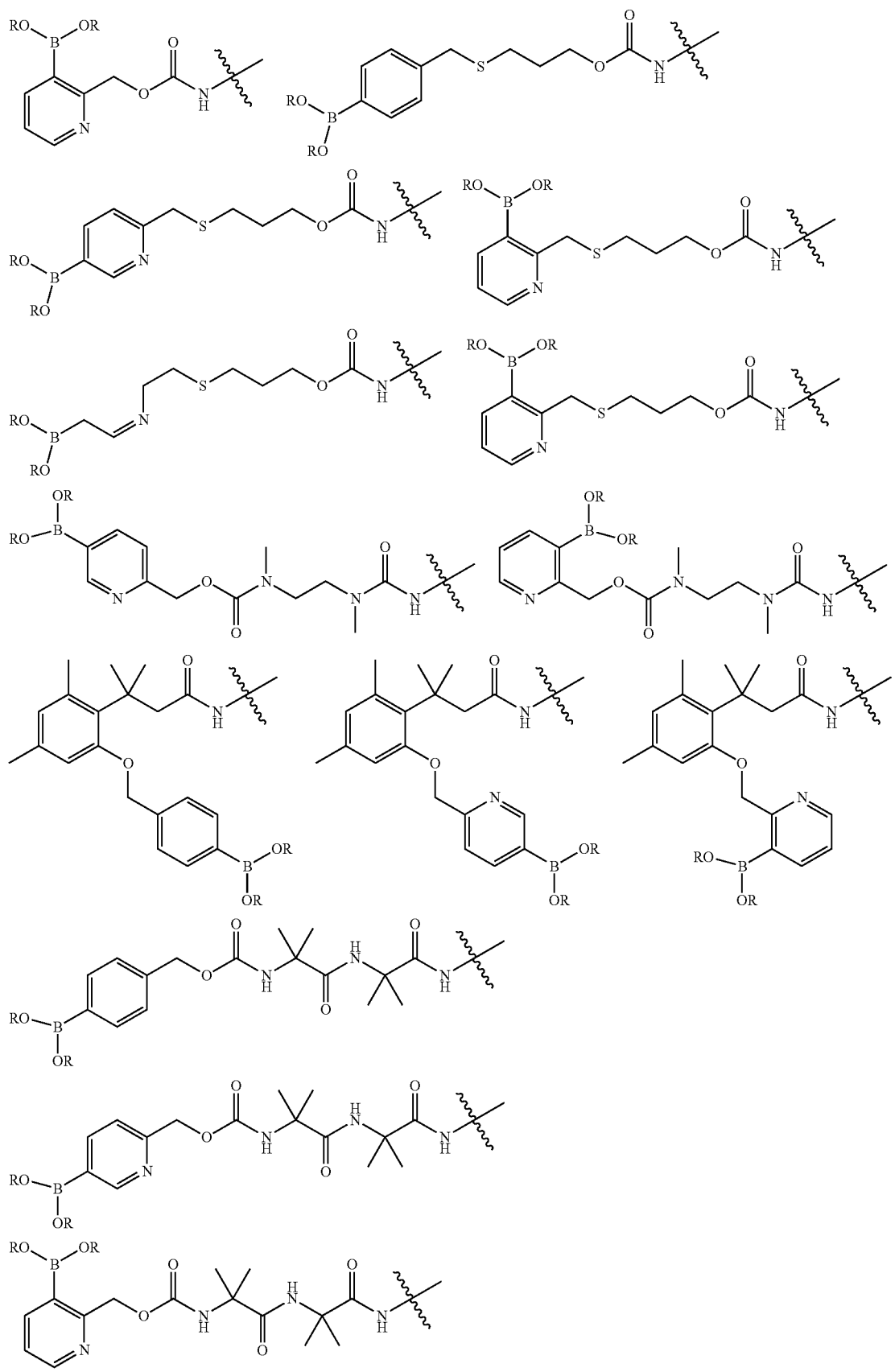

-continued
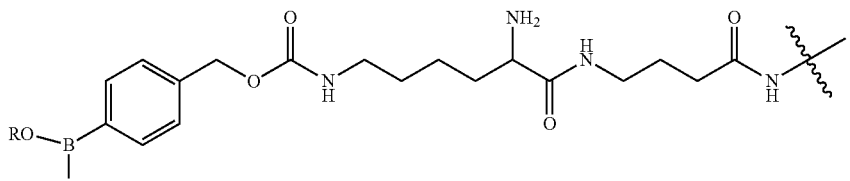
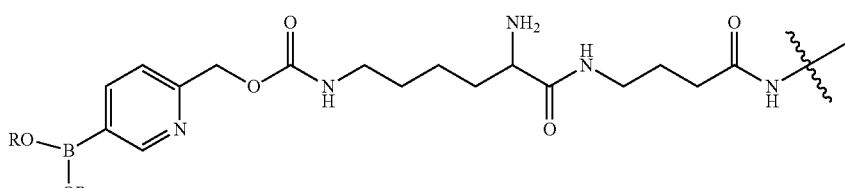
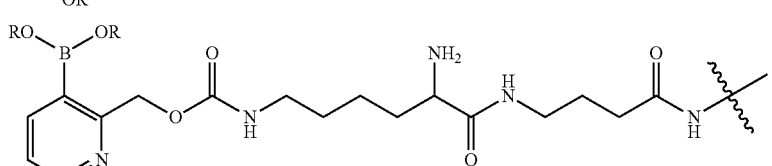
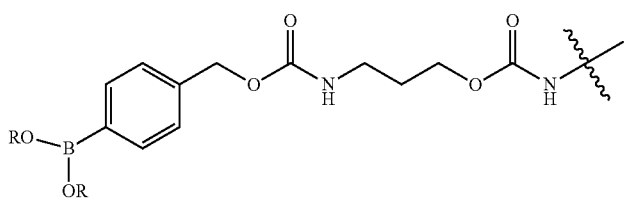
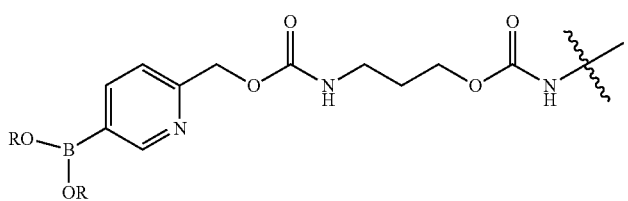
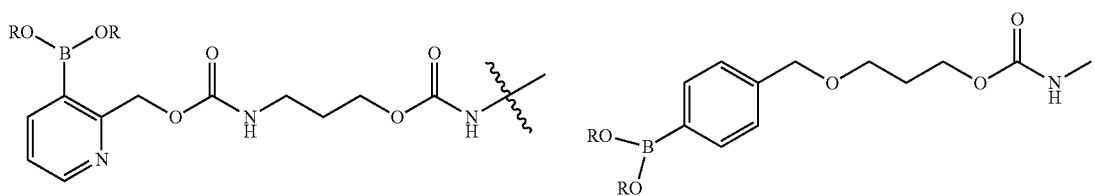
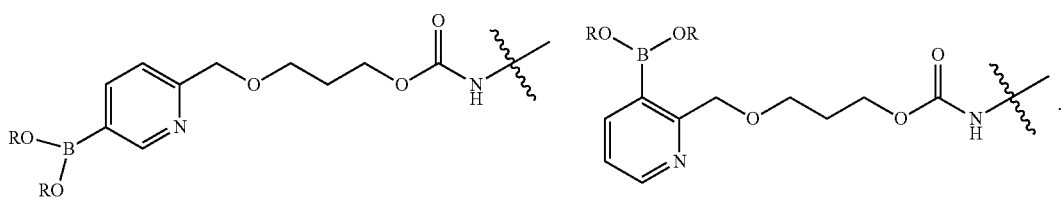

Aspect 9. The compound of aspect 7 or 8, wherein the compound is of formula (V):

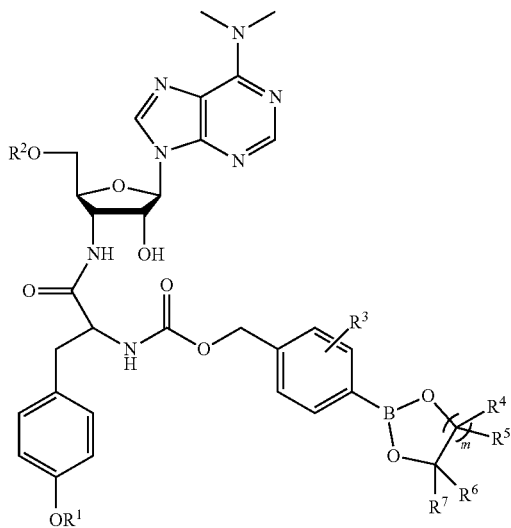

(V)

wherein:
R$^1$, R$^2$ and R$^3$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl;

R$^4$, R$^5$, R$^6$ and R$^7$ are independently hydrogen, substituted or unsubstituted alkyl, and substituted or unsubstituted heteroalkyl;

m is integer selected from 1, 2 and 3.

Aspect 10. The compound of aspect 6, wherein the compound is of formula (VI):

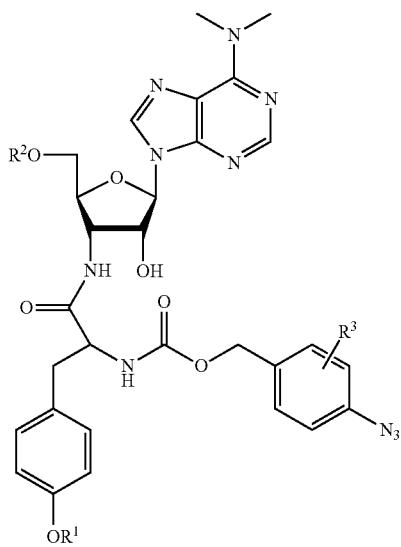

(VI)

wherein:
R$^1$, R$^2$ and each R$^3$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

Aspect 11. The compound of aspect 6, wherein the compound is of formula (VII):

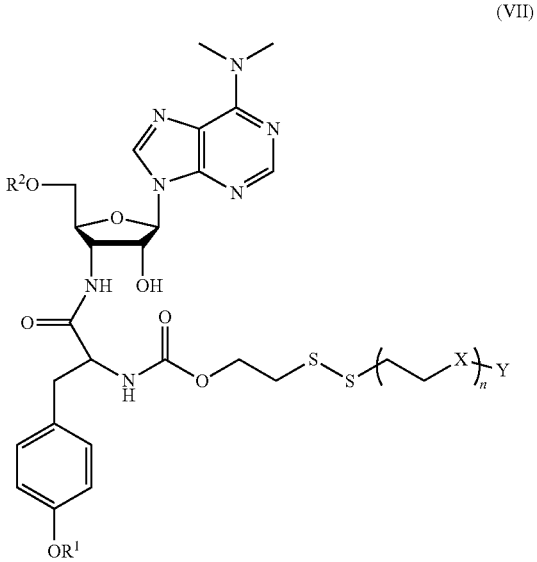

(VII)

wherein:
R$^1$ and R$^2$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl;

X is C$_0$, NH, CH$_2$, O or S;

Y is hydrogen, substituted or unsubstituted alkyl, substituted or unsubstituted cycloalkyl, substituted or unsubstituted heteroalkyl, substituted or unsubstituted heterocycloalkyl, amido, carboxyl, ester, carbonyl, alkanoyl, substituted alkanoyl, formyl, thio, alkythio, sulfonyl, sulfonic acid, azidyl, nitro, isocyanate-yl, alkenyl, alkynyl, sulfonyl, sulfonic acid, phosphoryl, phosphonyl group, aryl or substituted aryl; and n is integer from 0 to 20 (e.g., 0 to 10, 1 to 10, 1 to 6).

Aspect 12. The compound of aspect 6, wherein the compound is of formula (VIII):

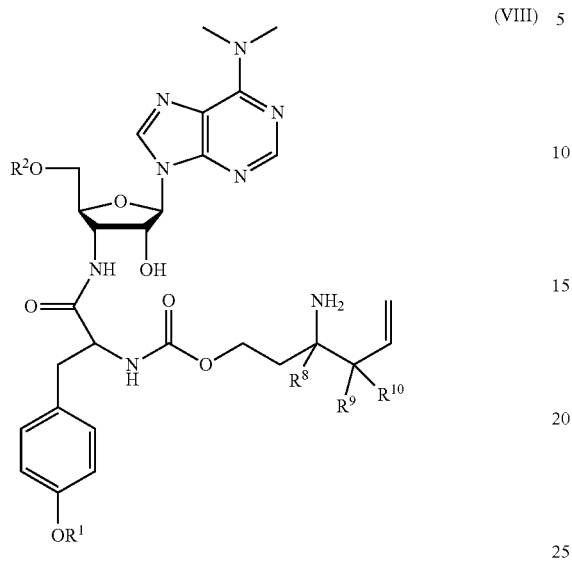

wherein:
$R^1$, $R^2$, $R^8$, $R^9$ and $R^{10}$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

Aspect 13. The compound of aspect 6, wherein the compound is of one of formulae (IX)-(XI):

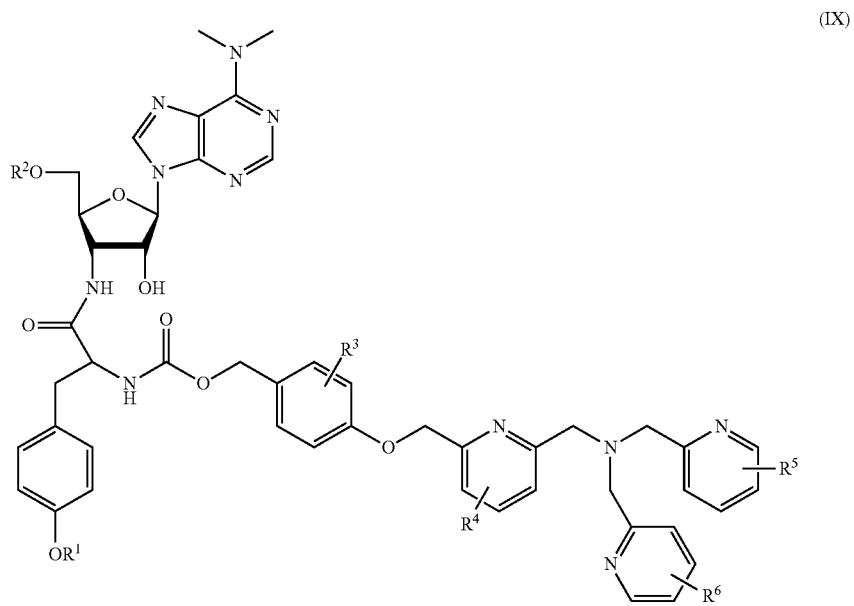

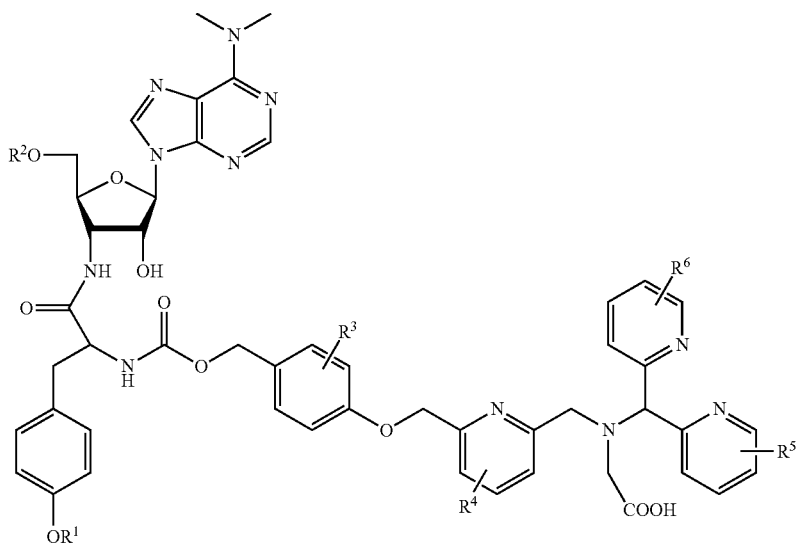

(X)

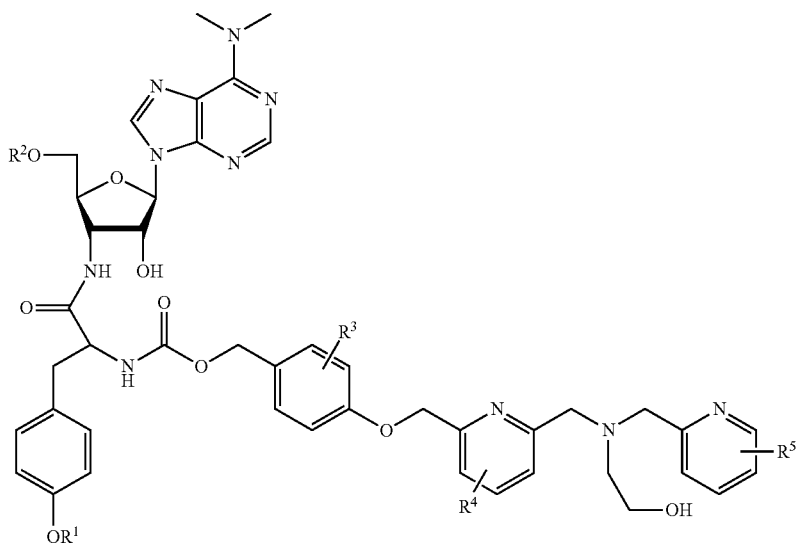

(XI)

wherein:

$R^1$, $R^2$, $R^3$, $R^4$, $R^5$ and $R^6$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

Aspect 14. The compound of any one of aspects 9-13, wherein $R^1$ is $CH_3$ and $R^2$ is H; and in formula (V), $R^3$ is H and $R^4$, R, $R^6$ and $R^7$ are each independently lower alkyl (e.g., methyl);

in formula (VI), $R^3$ is H;

in formula (VII), X is O, Y is alkanoyl (e.g., acetyl) and n is 1.

in formula (VIII), $R^8$, $R^9$ and $R^{10}$ are each independently lower alkyl (e.g., methyl); and in formulae (IX)-(XI), $R^3$-$R^6$ are each H.

Aspect 15. A composition comprising:
the compound of any one of aspects 1-14; and
a pharmaceutically acceptable excipient.

Aspect 16. A kit comprising:
the compound of any one of aspects 1-14; and
an antibody specific for a puromycylated polypeptide.

Aspect 17. The kit of aspect 16, wherein the antibody comprises a detectable label.

Aspect 18. The kit of aspect 17, wherein the detectable label comprises a fluorophore, a chromophore, or a luminophore Aspect 19 The kit of any one of aspects 16-18, wherein the compound and the antibody are in separate containers.

Aspect 20. The kit of any one of aspects 16-19, further comprising, one or more components selected from an analyte standard, a cell, tissue, an enzyme and instructions for use.

Aspect 21. The kit of aspect 20, wherein the kit further comprises the analyte standard that is a redox-active small molecule selected from $H_2O_2$, $H_2S$, glutathione, formaldehyde and a redox-active metal ion (e.g., copper(I) ion solution, iron(II) ion solution, or cobalt(II) ion solution).

Aspect 22. A method of detecting a redox-active analyte in a sample, the method comprising:

contacting the sample with the compound of any one of aspects 1-14, wherein, in the presence of the redox-active analyte, moiety P is released from the compound and reacts with a nascent polypeptide present in the sample, thereby forming a puromycylated polypeptide; and detecting the puromycylated polypeptide, wherein detection of the puromycylated polypeptide provides for detection of the redox-active analyte in the sample.

Aspect 23. The method of aspect 22, wherein said detecting comprises contacting the sample with an antibody that specifically binds to the puromycylated polypeptide.

Aspect 24. The method of aspect 23, wherein the antibody comprises a detectable label.

Aspect 25. The method of aspect 24, wherein the detectable label comprises a fluorophore, a chromophore, or a luminophore.

Aspect 26. The method of any one of aspects 22-25, wherein the redox-active analyte is one or more of a reactive oxygen species (ROS), a reactive sulfur species (RSS), a reactive carbonyl species (RCS), an ROS scavenger, and a redox-active metal ion.

Aspect 27. The method of aspect 26, wherein the ROS is hydrogen peroxide, hypochlorous acid (HOCl), singlet oxygen ($^1O_2$), lipid peroxides (ROOH), ozone ($O_3$), or hydroxyl radical.

Aspect 28. The method of aspect 26, wherein the RSS is hydrogen sulfide ($H_2S$), a hydrogen polysulfide, a hydrodisulfide (RSSH), a persulfide (RSSR), or thiosulfate ($S_2O_3^{2-}$).

Aspect 29. The method of aspect 26, wherein the RCS is formaldehyde, 4-hydroxynonenal, dehydroascorbate, glucosone, oxaloacetate, methylglyoxal, acetaldehyde, pyruvate, or glucose.

Aspect 30. The method of aspect 26, wherein the ROS scavenger is glutathione (GSH) or thioredoxin reductase.

Aspect 31. The method of aspect 26, wherein the redox-active metal ion is manganese, iron, cobalt, nickel, copper, or zinc.

Aspect 32. The method of any one of aspect 22-31, wherein the sample is an acellular sample.

Aspect 33. The method of any one of aspect 22-31, wherein the sample comprises a cell.

Aspect 34. The method of any one of aspect 22-31, wherein the sample comprises a cell lysate, a tissue, or a bodily fluid.

Aspect 35. The method of any one of aspects 22-31, wherein the sample comprises cerebrospinal fluid, bronchoalveolar lavage, blood, serum, plasma, tears, sputum, saliva, or mucus.

Aspect 36. The method of any one of aspects 22-35, wherein the sample is in vitro.

Aspect 37. The method of any one of aspects 22-31 and 33, wherein the sample is in vivo.

Aspect 38. A method of detecting a redox-active analyte in a cell, tissue, organ, or fluid in a living subject, the method comprising:

administering to the subject the compound of any one of aspects 1-14, wherein, in the presence of the redox-active analyte, moiety P is released from the compound and reacts with a nascent polypeptide in the subject, thereby forming a puromycylated polypeptide; and detecting the puromycylated polypeptide, wherein detection of the puromycylated polypeptide provides for detection of the redox-active analyte in the subject.

Aspect 39. The method of aspect 38, wherein the subject is a mammal.

Aspect 40. The method of aspect 38 or 39, wherein the cell is a diseased cell.

Aspect 41. The method of aspect 40, wherein the diseased cell is a cancer cell.

Aspect 42. The method of aspect 38 or 39, wherein the subject has non-alcoholic fatty liver disease (NAFLD), and wherein the organ is the liver.

Aspect 43. The method of any one of aspects 38-42, wherein said detecting comprises contacting the cell, organ, tissue, or fluid with an antibody that specifically binds to the puromycylated polypeptide.

Aspect 44. The method of aspect 43, wherein the antibody comprises a detectable label.

Aspect 45. The method of aspect 44, wherein the detectable label comprises a fluorophore, a chromophore, or a luminophore.

Aspect 46. The method of any one of aspects 38-45, wherein the redox-active analyte is one or more of a reactive oxygen species (ROS), a reactive sulfur species (RSS), a reactive carbonyl species (RCS), an ROS scavenger, and a redox-active metal ion.

Aspect 47. The method of aspect 46, wherein the ROS is hydrogen peroxide, hypochlorous acid (HOCl), singlet oxygen ($^1O_2$), lipid peroxides (ROOH), ozone ($O_3$), or hydroxyl radical.

Aspect 48. The method of aspect 46, wherein the RSS is hydrogen sulfide ($H_2S$), a hydrogen polysulfide, a hydrodisulfide (RSSH), a persulfide (RSSR), or thiosulfate ($S_2O_3^{2-}$).

Aspect 49. The method of aspect 46, wherein the RCS is formaldehyde, 4-hydroxynonenal, dehydroascorbate, glucosone, oxaloacetate, methylglyoxal, acetaldehyde, pyruvate, or glucose.

Aspect 50. The method of aspect 46, wherein the ROS scavenger is glutathione (GSH) or thioredoxin reductase.

Aspect 51. The method of aspect 46, wherein the redox-active metal ion is manganese, iron, cobalt, nickel, copper, or zinc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

EXAMPLES

Figure 2:
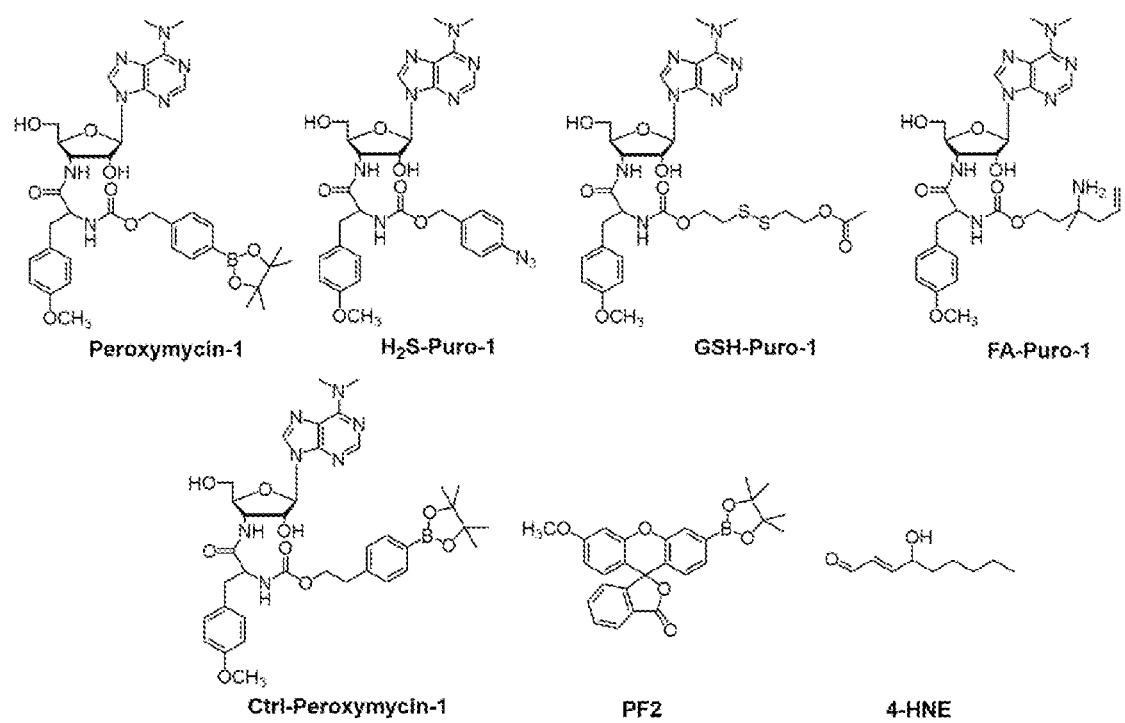
FIG. 2 shows the chemical structures of Peroxymycin-1, $H_2S$-Puro-1, GSH-Puro-1, FA-Puro-1 and Ctrl-Peroxymycin-1, as well as PF2 and 4-HNE. PF2 is a reported fluorescent $H_2O_2$ probe, while 4-HNE staining is often employed for measuring oxidative stress in fixed samples.

A puromycin-based method for molecular imaging and histochemistry of target analytes has been developed. The method is generally applicable to both cell and tissue samples, and these probes can be further applied for disease diagnosis and monitoring of treatment progress where the diseases are associated with the target analytes. A representative example, Peroxymycin-1, has been demonstrated as a selective and sensitive molecular probe for $H_2O_2$. Peroxymycin-1 utilizes the selective $H_2O_2$-mediated boronate oxidation reaction to generate puromycin and report $H_2O_2$ in a dose-dependent manner, whereas the negative control compound Ctrl-Peroxymycin-1 bearing the same boronate switch but with an extra carbon in the linker cannot eliminate to the parent puromycin product (FIG. 2). Peroxymycin-1 is capable of visualizing changes in exogenous and endogenous $H_2O_2$ levels in cells and can be used to profile differences in basal $H_2O_2$ levels across breast cell lines from non-tumorigenic cell models to non-metastatic to metastatic cancer cell lines. Moreover, this probe enables $H_2O_2$ detection in fixed tissues after in vivo application, as demonstrated by the identification of liver-specific elevations in $H_2O_2$ in a diet-induced mouse model of non-alcoholic fatty liver disease (NAFLD).

Example 1: Preparation and Characterization of Puromycin-Based Probes

In general, the syntheses of intermediates and puromycin-based probes were conducted under an inert atmosphere of nitrogen using Standard Schlenk technique. $^1$H NMR spectra were recorded with a AVB-400, AVQ-400 and AV-300 at the College of Chemistry NMR Facility at the University of California, Berkeley. All chemical shifts are reported in the standard δ notation of parts per million relative to residual solvent peak as an internal reference. Splitting patterns are indicated as follows: br, broad; s, singlet; d, doublet; t, triplet; m, multiplet; dd, doublet of doublets. Low-resolution electrospray mass spectra were recorded on a LC-MS (Agilent Technology 6130, Quadrupole LC/MS). High-resolution mass spectra were collected at the College of Chemistry Mass Spectrometry Facility at the University of California, Berkeley.

Synthesis and Characterization of 4-nitrophenyl [4-(4,4,5,5-tetramethyl-1,3,2-dioxaborolan-2-yl) phenyl]ethyl Carbonate 4-Nitrophenyl chloroformate (189.7 mg, 0.94 mmol) was dissolved in dry dichloromethane (20 mL). 4-(4,4,5,5-Tetramethyl-1,3,2-dioxaborolan-2-yl)phenylethanol (212.3 mg, 0.86 mmol) was added to the solution, followed by dropwise addition of 4-(dimethylamino)pyridine in dichloromethane (1.1 mmol, 2 mL) at 0° C. The reaction mixture was allowed to reach room temperature and stirred for 2 h. The reaction was quenched by saturated $NaHCO_{3(aq)}$ solution, and extracted with dichloromethane. The organic layer was further washed by saturated $NaHCO_{3(aq)}$ solution two times and once by saturated $NaCl_{(aq)}$ solution, dried over $MgSO_4$ and filtered. Volatile organic solvent was evaporated under reduced pressure, and the crude product was purified by column chromatography on silica gel using hexane-ethyl acetate (4:1, v/v) as eluent, yielding the desired product as a white solid (255.9 mg, 72%). $^1$H NMR (CDCl$_3$, 300 MHz): δ 8.22 (2H, d, J=7.8 Hz), 7.79 (2H, d, J=7.8 Hz), 7.28 (4H, m), 4.48 (2H, t, J=6.9 Hz), 3.08 (2H, t, J=6.6 Hz), 1.34 (12H, s). $^{13}$C{$^1$H} NMR (CDCl$_3$, 75 MHz) δ 155.5, 152.3, 145.3, 140.0, 135.2, 128.4, 125.2, 121.8, 83.8, 69.4, 35.1, 24.9. LRMS (ESI) m/z [M$^+$Na$^+$]$^+$ calcd for $C_{21}H_{24}BNO_7Na$: 436.15; found: 436.1.

Synthesis and Characterization of 2-{[2-(acetyloxy) ethyl]-2'-[2-[[(4-nitrophenoxy)carbonyl]oxy]ethyl]-dithio}ethane (2)

4-Nitrophenyl chloroformate (500.2 mg, 2.48 mmol) was dissolved in dry dichloromethane (20 mL). 2-{[2-(Acetyloxy)ethyl]dithio}ethanol (442.8 mg, 2.26 mmol) was added to the solution, followed by dropwise addition of 4-(dimethylamino)pyridine in dichloromethane (2.71 mmol, 2 mL) at 0° C. The reaction mixture was allowed to reach room temperature and stirred for 2 h. The reaction was quenched by saturated $NaHCO_{3(aq)}$ solution, and extracted with dichloromethane. The organic layer was further washed by saturated $NaHCO_{3(aq)}$ solution two times and once by saturated $NaCl_{aq}$) solution, dried over $MgSO_4$ and filtered. Volatile organic solvent was evaporated under reduced pressure, and the crude product was purified by column chromatography on silica gel using $CH_2C2$ as eluent, yielding the desired product as a white solid (148.8 mg, 18%). $^1$H NMR (CDCl$_3$, 300 MHz): δ 8.27 (2H, d, J=9.3 Hz), 7.39 (2H, d, J=9.0 Hz), 4.54 (2H, t, J=6.6 Hz), 4.33 (2H, t, J=6.6 Hz), 3.03 (2H, t, J=6.6 Hz), 2.95 (2H, t, J=6.6 Hz), 2.06 (3H, s). $^{13}$C{$^1$H} NMR (CDCl$_3$, 75 MHz) δ 170.9, 155.5, 152.4, 145.6, 125.4, 121.9, 66.9, 62.3, 37.3, 36.8, 21.0. LRMS (ESI) m/z [M$^+$Na$^+$]$^+$ calcd for $C_{13}H_{15}NO_7S_2Na$: 384.02; found: 384.0.

Synthesis and Characterization of Peroxymycin-1

Puromycin dihydrochloride (20 mg, 36.7 μmol) and 4-nitrophenyl [4-(4,4,5,5-tetramethyl-1,3,2-dioxaborolan-2-yl) benzyl carbonate (13.3 mg, 33.3 μmol) were dissolved in dry dimethylformamide (4 mL). 4-(Dimethylamino)pyridine in dimethylformamide (5 μmol; 1 mL) and N,N-diisopropylethylamine (23.3 μL; 134 μmol) were then added to the reaction mixture, and the solution was stirred at room temperature for 1 h. The reaction was then quenched by saturated $NaHCO_{3(aq)}$ solution, and extracted with ethyl acetate. The organic layer was further washed by saturated $NaHCO_{3(aq)}$ solution two times and once by saturated NaCl$_{(aq)}$ solution, dried over $MgSO_4$ and filtered. Volatile organic solvent was evaporated under reduced pressure, and the crude product was purified by column chromatography on silica gel using dichloromethane-methanol (9:1, v/v) as eluent, yielding the desired product as a white solid (16.6 mg, 68%). $^1$H NMR (CDCl$_3$, 400 MHz): δ 8.05 (1H, s), 7.93 (1H, s), 7.77 (2H, d, J=7.6 Hz), 7.28 (2H, d, J=7.6 Hz), 7.12 (2H, d, J=8.0 Hz), 6.84 (2H, d, J=8.0 Hz), 6.59 (1H, br), 5.63 (1H, d, J=6.4 Hz), 5.48 (1H, d, J=4.4 Hz), 5.02-5.11 (3H, m), 4.74 (1H, m), 4.43 (1H, m), 4.37 (1H, m), 4.02 (1H, s), 3.88 (1H, d, J=12.8 Hz), 3.76 (3H, s), 3.69 (1H, d, J=12.8 Hz), 3.10-3.67 (6H, br), 3.00-3.10 (1H, m), 2.90-3.00 (1H, m), 1.33 (12H, s). $^{13}$C{$^1$H} NMR (CDCl$_3$, 100 MHz) δ 172.1, 158.7, 156.2, 154.7, 151.3, 148.4, 139.1, 137.7, 135.0, 130.3, 128.4, 127.0, 121.0, 114.2, 90.9, 84.9, 83.9, 72.7, 67.0, 62.4, 56.6, 55.3, 51.7, 38.3, 24.9. HRMS (ESI) m/z [M$^+$H$^+$]$^+$ calcd for $C_{36}H_{47}BN_7O_9$: 732.3528; found: 732.3530.

Synthesis and Characterization of Ctrl-Peroxymycin-1

The procedure was similar to that of Peroxymycin-1 except that 4-nitrophenyl [4-(4,4,5,5-tetramethyl-1,3,2-dioxaborolan-2-yl)phenyl]ethyl carbonate (13.7 mg, 33.3 μmol) was used instead of [4-(4,4,5,5-tetramethyl-1,3,2-dioxaborolan-2-yl)benzyl carbonate, yielding the desired product as a white solid (15.4 mg, 62%). $^1$H NMR (CDCl$_3$, 400 MHz): δ 8.05 (1H, s), 7.92 (1H, s), 7.72 (2H, d, J=7.6 Hz), 7.18 (2H, d, J=7.6 Hz), 7.12 (2H, d, J=7.2 Hz), 6.85 (2H, d, J=8.4 Hz), 6.59 (1H, br), 5.51 (1H, d, J=7.2 Hz), 5.47 (1H, s), 5.10 (1H, br), 4.76 (1H, s), 4.30-4.45 (2H, m), 4.24 (2H, t, J=6.4 Hz), 4.05 (1H, s), 3.89 (1H, d, J=12.0 Hz), 3.75

(3H, s), 3.67 (1H, d, J=12.0 Hz), 3.10-3.67 (6H, br), 3.00-3.10 (1H, m), 2.85-2.95 (3H, m), 1.31 (12H, s). $^{13}C\{^1H\}$ NMR (CDCl$_3$, 100 MHz) δ 172.1, 158.7, 156.2, 154.8, 151.0, 148.0, 141.1, 137.7, 135.0, 130.3, 128.4, 121.1, 114.3, 91.0, 84.9, 83.8, 72.9, 65.7, 62.3, 56.5, 55.3, 51.5, 38.2, 35.6, 24.9. HRMS (ESI) m/z [M$^+$H$^+$]$^+$ calcd for C$_{37}$H$_{49}$BN$_7$O$_9$: 746.3685; found: 746.3685.

Synthesis and Characterization of H$_2$S-Puro-1

The procedure was similar to that of Peroxymycin-1 except that 4-azidobenzyl 4-nitrophenyl carbonate (15.7 mg, 50.0 μmol) was used instead of [4-(4,4,5,5-tetramethyl-1,3,2-dioxaborolan-2-yl)benzyl carbonate, yielding the desired product as a white solid (19.6 mg, 61%). $^1$H NMR ([D$_6$] DMSO, 400 MHz): δ 8.45 (1H, s), 8.24 (1H, s), 8.16 (1H, d, J=7.6 Hz), 7.47 (1H, d, J=8.4 Hz), 7.10-7.30 (4H, m), 6.95-7.10 (2H, m), 6.82 (2H, J=8.4 Hz), 6.11 (1H, d, J=4.0 Hz), 6.00 (1H, d, J=2.4 Hz), 5.00-5.30 (1H, br), 4.80-5.00 (2H, m), 4.40-4.55 (2H, m), 4.25-4.40 (1H, m), 3.95 (1H, s), 3.72 (3H, s), 3.68 (1H, d, J=12.8 Hz), 3.20-3.60 (7H, br), 2.85-3.00 (1H, m), 2.69 (1H, t, J=10.8 Hz). $^{13}C\{^1H\}$ NMR ([D$_6$]DMSO, 100 MHz) δ 171.9, 157.8, 155.7, 154.3, 151.8, 149.7, 138.7, 137.9, 134.1, 130.3, 129.8, 129.2, 119.6, 119.0, 113.4, 89.4, 83.4, 73.0, 64.6, 60.9, 56.3, 54.9, 50.3, 37.1, 29.6. IR (solid, cm$^{-1}$): 2114 (azide). HRMS (ESI) m/z [M$^+$H$^+$]$^+$ calcd for C$_{30}$H$_{35}$N$_{10}$O$_7$: 647.2690; found: 647.2688.

Synthesis and Characterization of GSH-Puro

The procedure was similar to that of Peroxymycin-1 except that 2-{[2-(acetyloxy)ethyl]-2'-[2-[[(4-nitrophenoxy)carbonyl]oxy]ethyl]-dithio}ethane (18.1 mg, 50 μmol) was used instead of [4-(4,4,5,5-tetramethyl-1,3,2-dioxaborolan-2-yl)benzyl carbonate, yielding the desired product as a white solid (25.9 mg, 75%). $^1$H NMR (CDCl$_3$, 400 MHz): δ 8.05 (1H, s), 7.96 (1H, s), 7.14 (2H, d, J=8.4 Hz), 6.86 (2H, d, J=8.8 Hz), 6.67 (1H, br), 5.76 (1H, d, J=7.6 Hz), 5.52 (1H, d, J=4.4 Hz), 5.25-5.35 (1H, br), 4.76 (1H, m), 4.35-4.48 (2H, m), 4.25-4.34 (4H, m), 4.06 (1H, br), 3.90 (1H, d, J=12.0 Hz), 3.77 (3H, s), 3.70 (1H, d, J=12.8 Hz), 3.35-3.65 (6H, br), 2.85-3.10 (7H, m), 2.05 (3H, s). $^{13}C\{^1H\}$ NMR (CDCl$_3$, 100 MHz) δ 172.2, 171.2, 158.9, 156.0, 154.9, 151.8, 148.0, 137.8, 130.4, 128.5, 121.1, 114.4, 91.1, 85.1, 73.0, 63.1, 62.6, 62.5, 56.7, 55.5, 53.6, 51.7, 38.2, 37.8, 37.1, 31.1, 21.1. HRMS (ESI) m/z [M$^+$H$^+$]$^+$ calcd for C$_{29}$H$_{40}$N$_7$O$_9$S$_2$: 694.2329; found: 694.2328.

Example 2: Spectroscopic Materials and Methods

MilliQ water was used in all experiments unless otherwise stated. Reaction kinetics of the probes with species of interest and other substrates were investigated by LC-MS (Agilent Technology 6130, Quadrupole LC/MS) coupled with photodiode array for detection (X=275 nm). Confocal microscopy images were recorded on a Zeiss laser scanning microscope 710 with a 40× water-immersion objective lens using Zen 2009 software (Carl Zeiss).

2.1 LC-MS Analysis

Peroxymycin-1 and Ctrl-Peroxymycin-1 (0.3 mM), respectively, were dissolved in phosphate buffer (20 mM, pH 7.4)-methanol solution mixture (2:1, v/v) with 3 vol % DMSO and allowed to stand at room temperature. At predetermined time intervals, an aliquot of the solution mixture was taken for LC-MS analysis. Separation was achieved by gradient elution from 5-100% MeOH in water (constant 0.1 vol % formic acid) over 8 min, isocratic with 100% MeOH from 8 to 12 min and returned to initial conditions and equilibrated for 3 minutes. The LC chromatograms were recorded by monitoring absorption at 275 nm.

For the study of the reaction with H$_2$O$_2$, Peroxymycin-1 and Ctrl-Peroxymycin-1 (0.3 mm), respectively, were dissolved in phosphate buffer (20 mM, pH 7.4)-methanol solution mixture (2:1, v/v) with 3 vol % DMSO. H$_2$O$_2$ was then added to the solution mixture (final concentration=0.1 mM), and the reaction mixture was allowed to stand at room temperature. At predetermined time intervals, an aliquot of the solution mixture will be taken for LC-MS analysis as described above.

For other ROS, they were generated as described previously (Carroll, et al. J. Am. Chem. Soc. 2014, 136, 14742), and then added to the solution of peroxymycin with final concentration of 0.1 mM, except that the final concentration of peroxynitrite was 0.05 mM which is its physiologically relevant concentration. An aliquot of the solution was then taken for LC-MS analysis as described above.

2.2 Cell culture

Human cervical epithelial carcinoma (HeLa), human epidermoid carcinoma (A-431) and human breast carcinoma (MDA-MB-231 and MDA-MB-468) were maintained in DMEM medium (high glucose) supplemented with GlutaMAX and 10 vol % FBS. Human breast carcinoma (MCF-7) was maintained in DMEM medium (high glucose) supplemented with GlutaMAX, 10 vol % FBS, 1 vol % non-essential amino acids and 1% sodium pyruvate. Human breast carcinoma (HS 578T) was maintained in DMEM medium (high glucose) supplemented with GlutaMAX, 10 vol % FBS, 1% sodium pyruvate and insulin (10 μg/mL). Human non-tumorigenic breast epithelial cells (MCF-10A) were maintained in DMEM/F12 (with L-glutamate, HEPES and phenol red) supplemented with 5 vol % horse serum, EGF (20 ng/mL), hydrocortisone (0.5 mg/mL), cholera toxin (100 ng/mL), insulin (10 μg/mL) and 1 vol % penicillin/streptomycin. Human normal breast epithelial cells (HS 578Bst) were maintained in ATCC Hybri-Care Medium (No. 46-X) supplemented with sodium bicarbonate (1.5 g/mL), EGF (30 ng/mL) and 10 vol % FBS. All cells were incubated in 5% CO$_2$ humidified air, and subcultured when 80% confluence was reached. For cell-imaging experiments, the cells were plated on 8-well Lab Tek borosilicate chambered coverglass slides (Nunc) or 24-well plates with 12 mm coverslips, and allowed to grow to ca. 60% confluency before performing the cell imaging experiments.

2.3 Immunostaining of Cells Treated with Puromycin-Based Probes

Cells were incubated with the compound (1 μM) for indicated time intervals. The cells were then washed three-times by PBS solution and fixed by 4% paraformaldehyde at room temperature for 10 min. The cells were washed by PBS solution and PBS solution with 0.1 vol %-Triton X-100, followed by incubation with α-puromycin antibody [3RH11] (Kerafast; 1:500, v/v) in PBS solution containing 10 vol % FBS and 0.1 vol % Triton X-100 at 37° C. for 30 min. Subsequently, the cells were washed by PBS solution and PBS solution with 0.1 vol %-Triton X-100, and stained by α-mouse secondary antibody-Alexa Fluor 488 (1:100, v/v) in PBS solution containing 10 vol % FBS and 0.1 vol % Triton X-100 at 37° C. for 30 min. The cells were then washed by PBS solution and stained by Hoechst 33342 at room temperature for 10 min. After that, the cells were washed three-times by PBS solution and imaged by confocal fluorescence microscopy.

2.4 Stimulation and Inhibition of $H_2O_2$ or NO Production in A431 Cells

EGF stimulation was carried out by pretreatment of A431 cells by EGF (100 ng/mL) for 20, 40 and 60 min, then washed by PBS and incubated with Peroxymycin-1 (1 μM) for 4 h.

For the study with L-NAME, A431 cells were pretreated with L-NAME (100 μM) for 25 min, then washed by PBS and incubated with EGF (100 ng/mL) for 40 min, followed by washing and incubation with Peroxymycin-1 (1 μM) for 4 h.

For the DPI experiment, the cells were pretreated with a mixture of DPI (5 μM) and EGF (100 ng/mL) for 40 min, followed by incubation with a mixture of DPI (5 μM) and Peroxymycin-1 (1 μM) for 4 h.

For the inhibition of $H_2O_2$ production by gp91 Tat peptide, the cells were pretreated with gp91 Tat peptide (100 μM) for 30 min, then incubated with a mixture of gp91 Tat peptide (100 μM) and Peroxymycin-1 (1 μM) for 4 h.

2.5 Confocal Fluorescence Microscopy Imaging

Confocal fluorescence cell imaging was performed with a Zeiss laser scanning microscope 710 with a 40× water-immersion objective lens using Zen 2009 software (Carl Zeiss). Hoechst 33342 was excited with a 405 nm diode laser, and emission was collected using a META detector between 450 and 500 nm. Alexa Fluor 488 was excited with 488 nm with an Ar laser, and emission was collected using a META detector between 500 and 625 nm. Alexa Fluor 647 was excited with a 633 nm HeNe laser, and emission was collected using a META detector between 638 and 647 nm. PBS solution was used as the imaging buffer for all the confocal experiments. Image analysis was performed using ImageJ. A region of interest (ROI) was created around a single cell, and cellular fluorescence intensity was measured. The reported cellular fluorescence intensity was determined by averaging the measured intensity of 5 different cells from at least 3 different images in triplicate experiments. Statistical analyses were performed with a two-tailed Student's t-test (MS Excel).

2.6 Animal Work 8 wk old male C57BL/6 mice were fed either standard chow or high fat diet (60% kcal from fat, Research Diets D12492) for 20 weeks. Body weight of the mice were measured weekly. All animal studies were approved by and performed according to the guidelines of the Animal Care and Use Committee of the University of California, Berkeley.

2.7 Imaging $H_2O_2$ in Liver Tissues of Mice Fed with NC or HFD

NC and HFD mice, respectively, were injected intraperitoneally with 10 mg/kg of peroxymycin. After 4 hours, mice were euthanized and liver tissue harvested.

For dot blots, 10 mg of liver tissues were homogenized in RIPA buffer. Cleared lysates were quantified and spotted on a nitrocellulose membrane at protein content of 2 g. After blocking, the membrane was incubated with anti-puromycin and anti-lamin B (Abcam 16048) primary antibodies (1:1000, v/v) at 4° C. overnight. Then, the dot blot was incubated with dye-conjugated secondary antibodies (Invitrogen, 1:10,000, v/v) for 1 hour at room temperature and visualized using a Licor Odyssey Imaging System. ImageJ was used for blot quantification.

For confocal fluorescence imaging of liver tissue sections, liver tissues were fixed by 4% paraformaldehyde at 4° C. overnight. Then, the tissues were injected into 30% sucrose solution for cryoprotection at 4° C. overnight. The tissues were then embedded in TFM, and 30 micron sections were taken on a cryostat and subsequently adhered to slides. After washing with PBS, the sections were incubated in PBS containing 0.5% BSA and 0.5% Triton X-100 at room temperature for 20 min, followed by incubation with anti-mouse IgG Fab (1:10, v/v) in PBS containing 0.5% BSA and 0.5% Triton X-100 at room temperature for 2 h. After that, the sections were washed with PBS containing 0.5% BSA and 0.5% Triton X-100 for 5 min at room temperature three times, and then incubated with donkey serum (10 vol %) in PBS containing 0.5% BSA and 0.5% Triton X-100 at room temperature for 2 h, followed by incubation with mouse α-puromycin antibody (1:100, v/v) in PBS containing 0.5% BSA and 0.5% Triton X-100 at room temperature for 1 h. Then the sections were washed with PBS containing 0.5% BSA and 0.5% Triton X-100 at room temperature for 5 min three times, and incubated with anti-mouse-Alexa647 antibody (1:250, v/v) in PBS containing 0.5% BSA and 0.5% Triton X-100 at room temperature for 1 h. The sections were washed with PBS containing 0.5% BSA and 0.5% Triton X-100 at room temperature for 10 min three times, mounted with coverslips and imaged by confocal fluorescence microscope.

For 4-HNE staining, after fixation, cryoprotection and sectioning, the sections were washed with PBS, incubated in PBS containing 0.5% BSA and 0.5% Triton X-100 at room temperature for 20 min, and then incubated with donkey serum (10 vol %) in PBS containing 0.5% BSA and 0.5% Triton X-100 at room temperature for 2 h. After that, the sections were incubated with goat anti-4HNE antibody (1:100, v/v) in PBS containing 0.5% BSA and 0.5% Triton X-100 at room temperature for 1 h, washed with PBS containing 0.5% BSA and 0.5% Triton X-100 at room temperature for 5 min three times, and incubated with anti-goat-Alexa647 antibody (1:250, v/v) in PBS containing 0.5% BSA and 0.5% Triton X-100 at room temperature for 1 h. The sections were washed with PBS containing 0.5% BSA and 0.5% Triton X-100 at room temperature for 10 min three times, mounted with coverslips and imaged by confocal fluorescence microscope.

Example 3: Reactivity of Puromycin-Based Probes with Target Analytes

Figure 4:
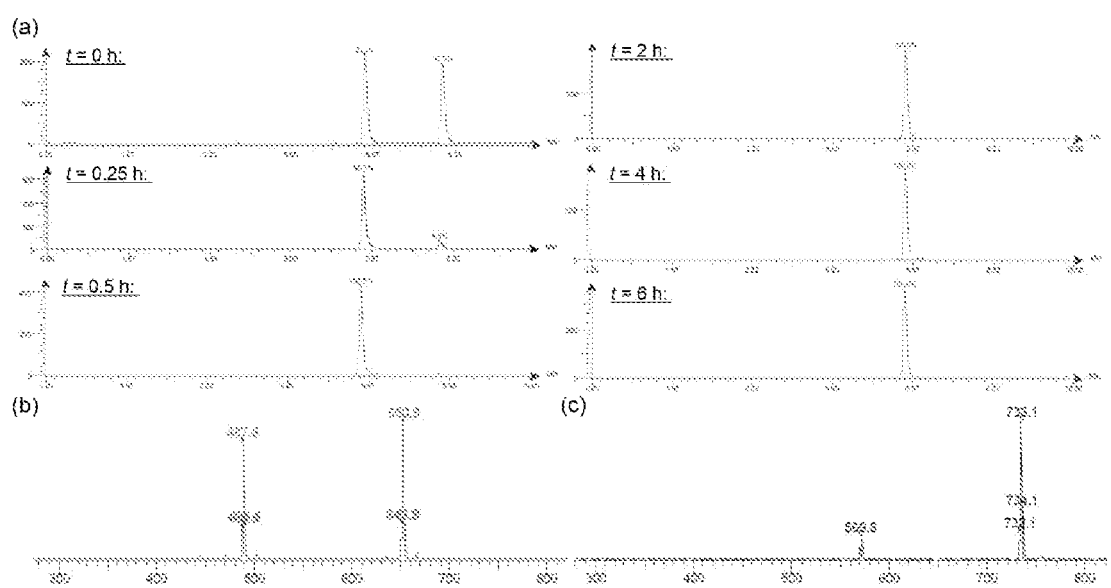
FIG. 4 shows stability of Peroxymycin-1 in the phosphate buffer (20 mM, pH 7.4)-methanol solution mixture (2:1, v/v) with 3 vol % DMSO.
Figure 5:
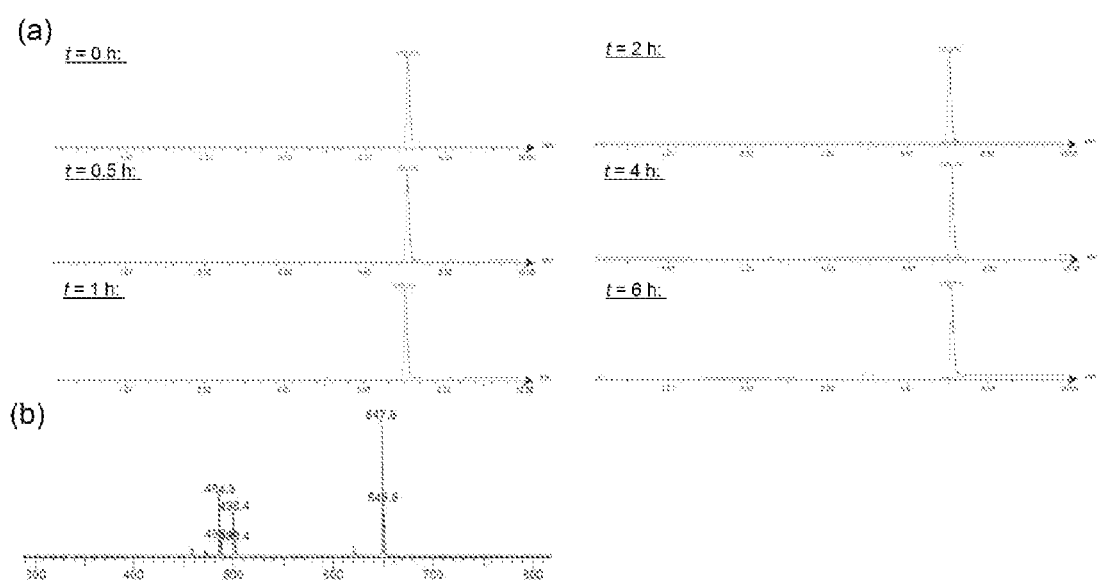
FIG. 5 shows stability of $H_2S$-Puro-1 in the phosphate buffer (20 mM, pH 7.4)-methanol solution mixture (2:1, v/v) with 3 vol % DMSO.
Figure 6:
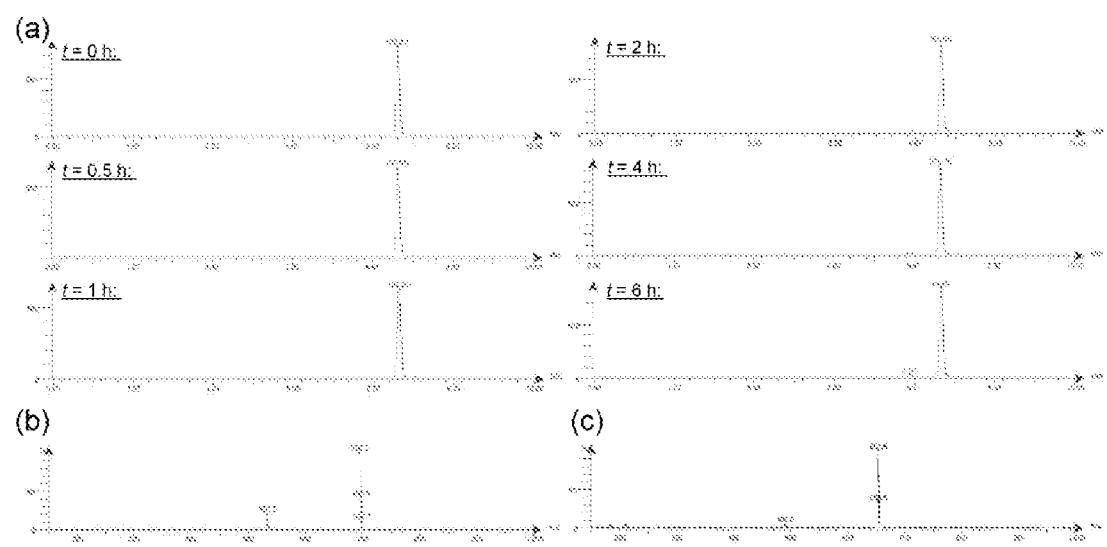
FIG. 6 shows stability of GSH-Puro-1 in the phosphate buffer (20 mM, pH 7.4)-methanol solution mixture (2:1, v/v) with 3 vol % DMSO.

Peroxymycin-1 maintains good stability in aqueous solution buffered to physiological pH, showing only conversion of the pinacol boronate to the parent boronic acid with no release of puromycin in the absence of $H_2O_2$ (FIG. 4). Similarly, $H_2$S-Puro-1 and GSH-Puro-1 are found to be stable in aqueous buffer solution for at least 6 h (FIGS. 5 and 6)

Figure 7:
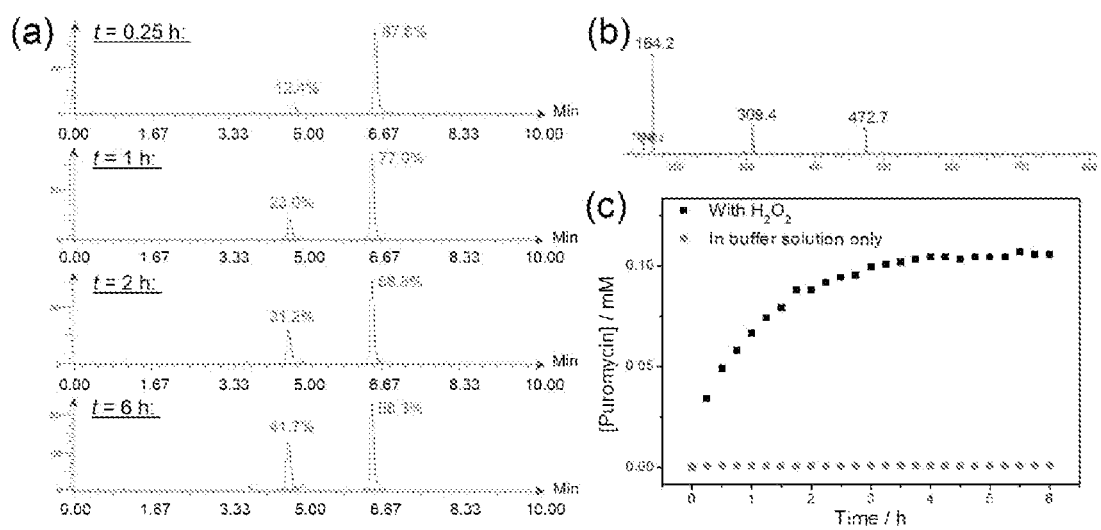
FIG. 7A shows LC chromatograms of the reaction mixture of Peroxymycin-1 (0.3 mM) and $H_2O_2$ (0.1 mM) in phosphate buffer (20 mM, pH 7.4)-methanol solution mixture (2:1, v/v) with 3 vol % DMSO at different time intervals.
FIG. 7B shows MS of the peak with retention time of 4.62 min, confirming formation of puromycin from the reaction between Peroxymycin-1 and $H_2O_2$.
FIG. 7c shows generation of puromycin from the solution of Peroxymycin-1 with and without $H_2O_2$, respectively, over time.

Treatment of Peroxymycin-1 with $H_2O_2$ produces puromycin, as shown by LC-MS analysis (FIGS. 7B and C), confirming the reaction depicted in Scheme 2a. The pseudo-first-order rate constant of the reaction at 25° C. was determined to be $1.0 \times 10^{-3}$ $s^{-1}$, with control experiments showing negligible puromycin generation from Peroxymycin-1 in the absence of $H_2O_2$ (FIG. 7C).

Figure 8:
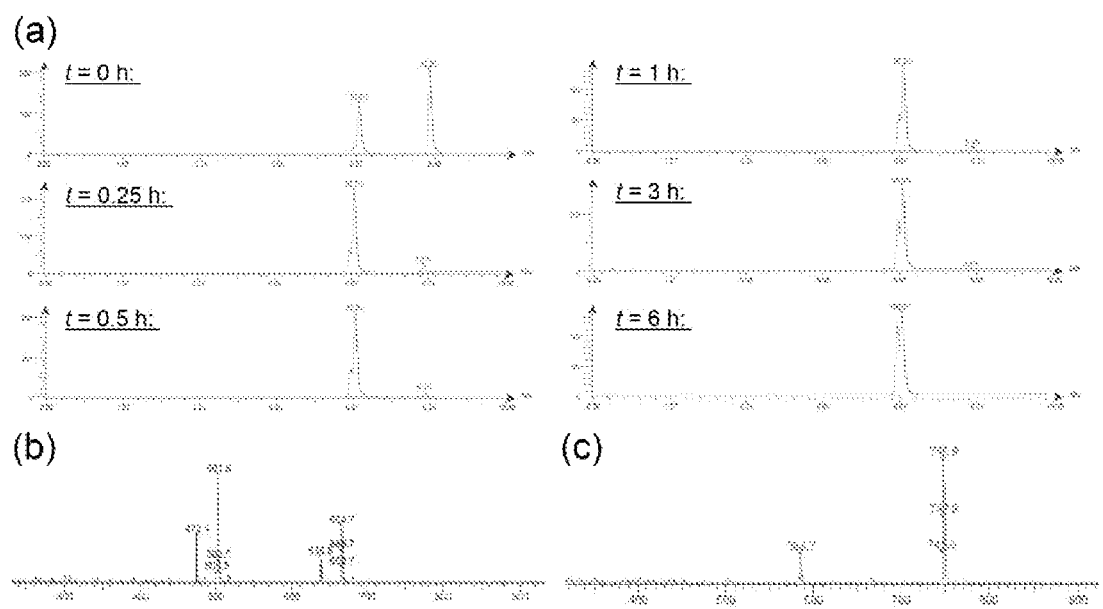
FIG. 8A shows LC chromatograms of the reaction mixture of Ctrl-Peroxymycin-1 (0.3 mM) and $H_2O_2$ (0.1 mM) in phosphate buffer (20 mM, pH 7.4)-methanol solution mixture (2:1, v/v) with 3 vol % DMSO at different time intervals.
FIG. 8B shows MS of the two peaks with retention time ranging from 6.50 to 6.80 min.
FIG. 8C shows MS of the peak with retention time of 8.22 min.

In another control experiment, the reaction between Ctrl-Peroxymycin-1 and $H_2O_2$ was also studied by LC-MS and shows only the corresponding phenol as a boronate oxidation product without self-immolative cleavage to produce puromycin (FIG. 8). These data further support the pathway depicted in Scheme 2 in which Peroxymycin-1 reacts with $H_2O_2$ through oxidation and subsequent self-immolation to yield free puromycin, rather than a mechanism involving direct cleavage of the carbamate linkage by $H_2O_2$.

Figure 3:
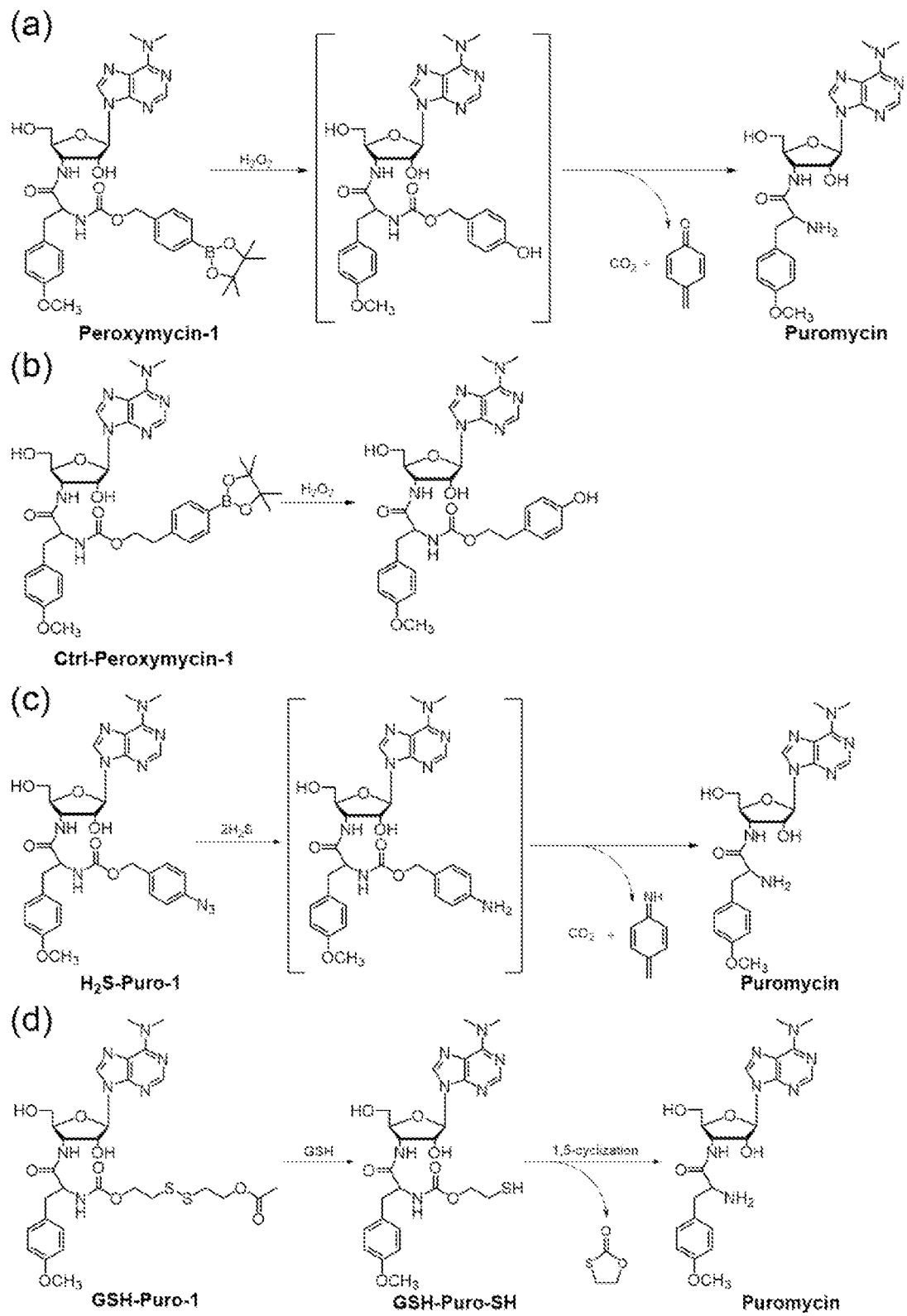
FIGS. 3A, 3B, 3C and 3D show reaction mechanism of Peroxymycin-1, Ctrl-Peroxymycin-1, $H_2S$-Puro-1 and GSH-Puro-1, respectively, as determined by LC-MS experiments
Figure 9:
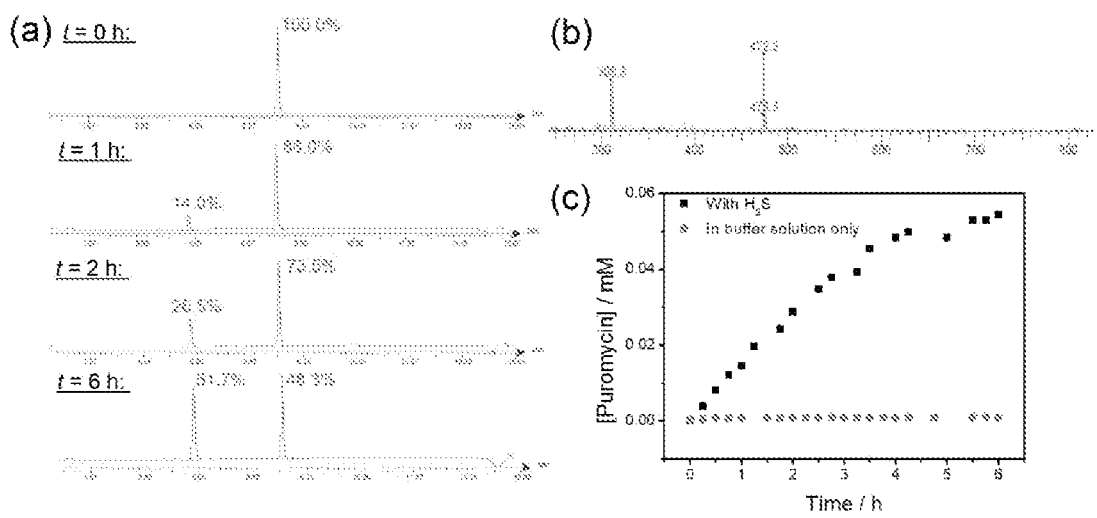
FIG. 9A shows LC chromatograms of the reaction mixture of $H_2S$-Puro-1 (0.3 mM) and $H_2S$ (1.0 mM) in phosphate buffer (20 mM, pH 7.4)-methanol solution mixture (2:1, v/v) with 3 vol % DMSO at different time intervals.
FIG. 9B shows MS of the peak with retention time of 4.62 min.
FIG. 9c shows generation of puromycin from the solution of $H_2S$-Puro-1 with and without $H_2S$, respectively, over time.

The reaction of $H_2S$-Puro-1 (0.3 mM) with $H_2S$ (1 mM) was also studied by LC-MS. A decrease in the peak of $H_2S$-Puro with retention time of 7.57 min was found, with concomitant growth of puromycin peak with retention time of 4.62 min over 6 h incubation (FIG. 9A). This supports that $H_2S$-Puro-1 can be reduced readily by $H_2S$, followed by self-immolation to form the free puromycin molecule (FIG. 3C). The reaction rate of $H_2S$-Puro-1 with $H_2S$ is relatively slow as compared to that of $H_2O_2$-Puro with $H_2O_2$. The pseudo-first-order rate constant of the reaction at 25° C. was found to be $6.3\times10^{-5}$ $s^{-1}$.

Figure 10:
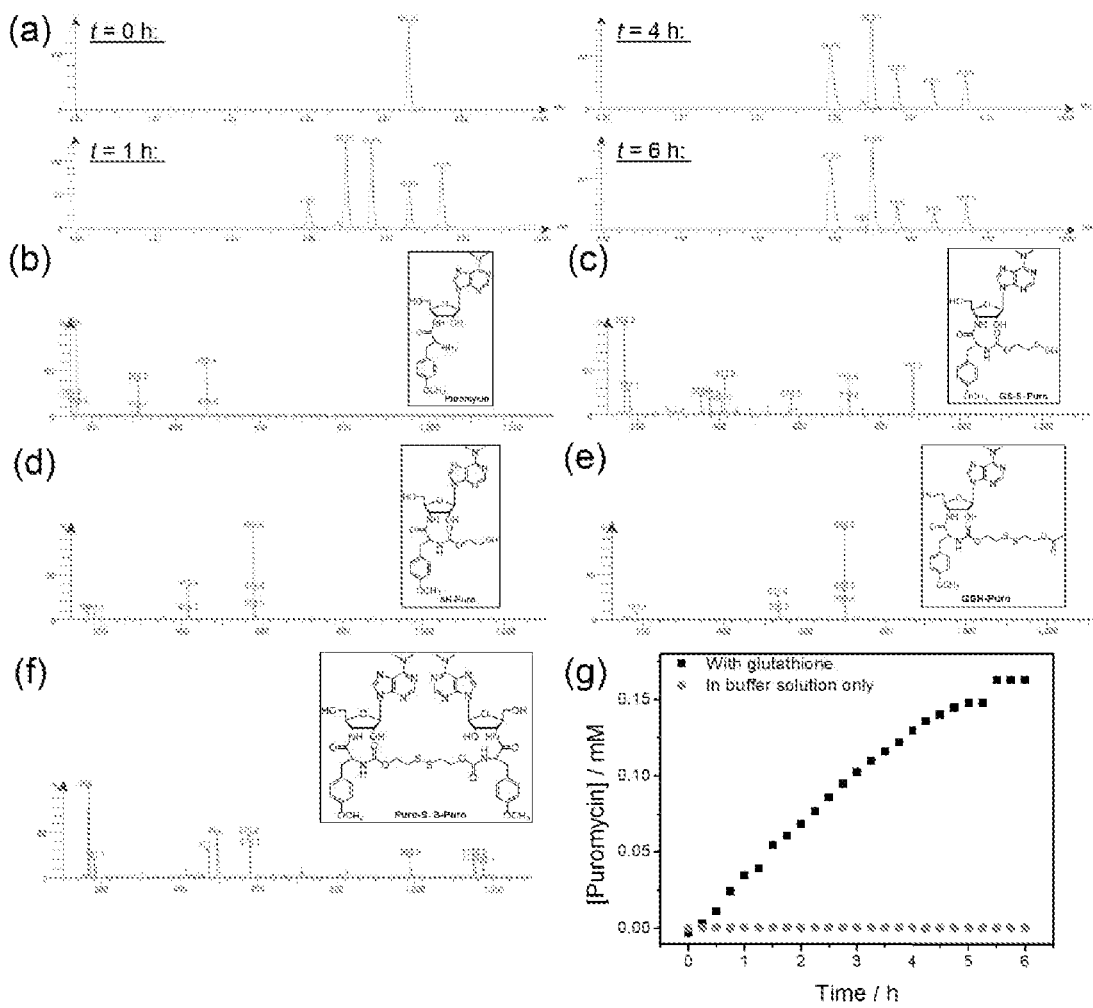
FIG. 10A shows LC chromatograms of the reaction mixture of GSH-Puro-1 (0.3 mM) and GSH (1.0 mM) in phosphate buffer (20 mM, pH 7.4)-methanol solution mixture (2:1, v/v) with 3 vol % DMSO at different time intervals.
FIGS. 10B, 10C, 10D, 10E and 10F shows MS of the peak with retention time of 4.62, 5.79, 6.34, 7.21 and 7.85 min respectively.
FIG. 10G shows generation of puromycin from the solution of GSH-Puro-1 with and without GSH, respectively, over time.

LC chromatograms of the reaction mixture of GSH-Puro-1 and GSH recorded over 6 h revealed peaks with retention times of 5.79, 6.34 and 7.85 min, in addition to the peaks of puromycin and GSH-Puro with retention times of 4.62 and 7.21 min respectively (FIG. 10A). According to the MS and the isotopic pattern (FIG. 10B-F), the peaks with retention times of 5.79, 6.34 and 7.85 min should be attributable to GS-S-Puro, GSH-Puro-SH and Puro-S—S-Puro respectively. Nonetheless, from the significant growth of intensity of the puromycin peak over time, the dithio species should be readily reduced by GSH to GSH-Puro-SH, which underwent further 1,5-cyclization to form free puromycin (FIG. 3D). The pseudo-first-order rate constant of the reaction at 25° C. was found to be $9.4\times10^{-5}$ $s^{-1}$, and hence the reaction rate is faster than that of $H_2S$-Puro and $H_2S$ but slower than that of $H_2O_2$-Puro and $H_2O_2$.

The selectivity of puromycin-based probes with target analytes were also investigated by LC-MS experiments. Peroxymycin-1 exhibits high selectivity for $H_2O_2$ over other ROS and reactive nitogen congeners as shown by LC-MS analyses (FIG. 11A). Only peroxynitrite at 50 µM, which is far higher than estimated physiologically relevant concentrations, gives any response, and the production of puromycin is an order of magnitude less than for $H_2O_2$. On the other hand, physiologically relevant concentration of $H_2S$, GSH, cysteine (Cys) and homocysteine (Hcys) can be 10-600 µM, 1-10 mM, 30-200 µM and 0.8-1.6 µM respectively. Under this condition, $H_2S$-Puro-1 and GSH-Puro-1 were found to be highly selective for $H_2S$ and GSH, with the formation of at least 5.0- and 4.9-fold more puromycin molecules respectively, as compared to their reactions with other substrates for 1 h (FIGS. 11B and 11C).

Figure 12:
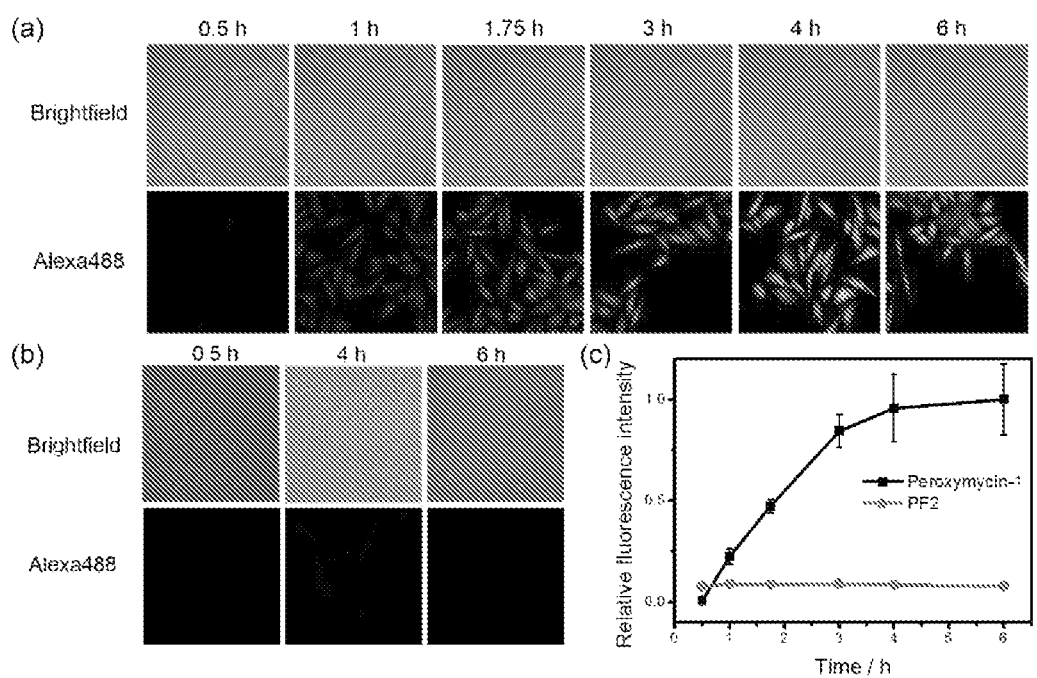
FIG. 12A shows confocal fluorescence microscopy images of HeLa cells stained with Peroxmycin-1 (1 μM) for indicated time intervals. The cells were then washed, fixed, stained and imaged.
FIG. 12B shows confocal fluorescence microscopy images of HeLa cells treated with PF2 (10 μM) for 0.5, 4 and 6 h respectively. The medium was then replaced by PBS solution and imaged. All the images in FIGS. 12A and 12b were recorded using the same imaging parameters with the Alexa488 channel.
FIG. 12C shows normalized cellular fluorescence intensities of the HeLa cells as determined by ImageJ, showing superior sensitivity for $H_2O_2$ detection for the new histochemical boronate $H_2O_2$ probe over a fluorescent probe counterpart. All the data are shown as mean±SEM. (n=5).
Figure 13:
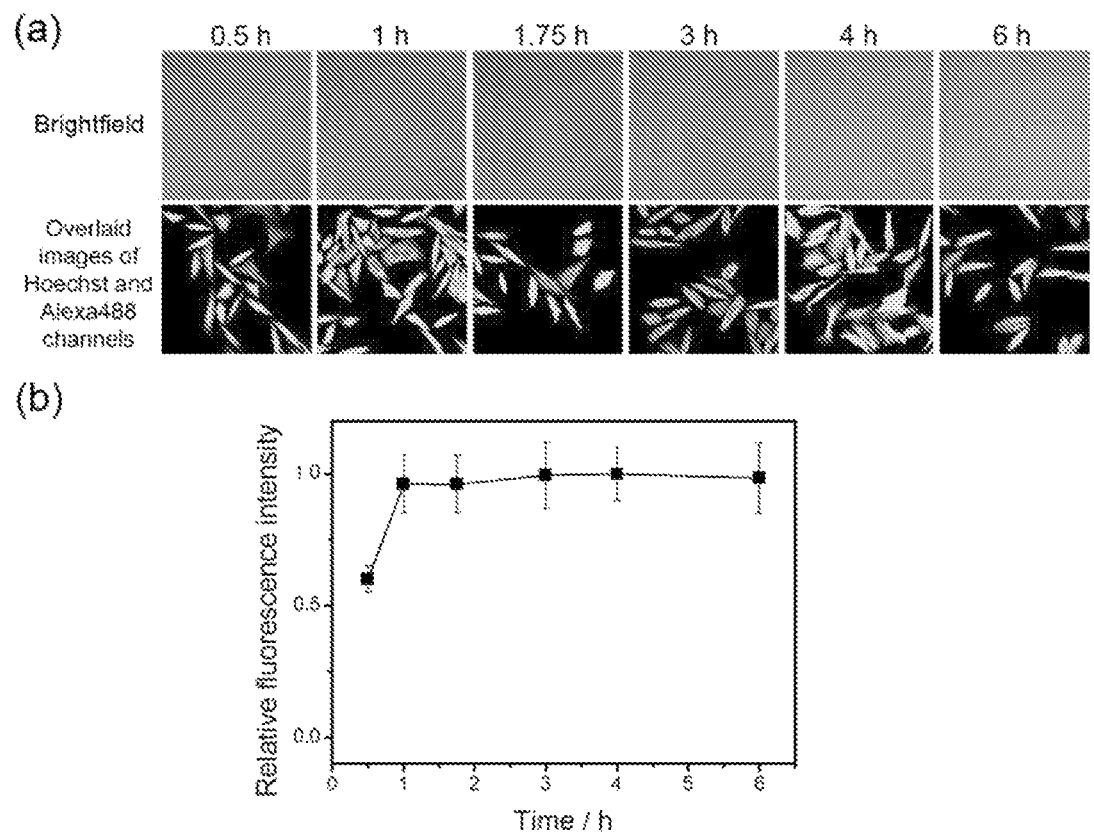
FIG. 13A shows confocal fluorescence microscopy images of HeLa cells treated with puromycin (1 µM) for indicated time intervals. The cells were then washed, fixed, stained and imaged.
FIG. 13B shows normalized cellular fluorescence intensities of the HeLa cells as determined by ImageJ. All the data are shown as mean±SEM. (n=5).

Example 4: Histochemical Detection of Cellular Analyte Levels Using Puromycin-Based Probes With in vitro characterization results in hand establishing the sensitivity and selectivity of puromycin-based probes for target analytes, we sought to apply these new chemical tools for histochemical detection of target analytes in cells. In initial experiments, HeLa cells were treated with either Peroxymycin-1 or puromycin at equivalent doses (1 µM), respectively, and monitored at different time intervals in order to assess cellular uptake and reaction of the probe with $H_2O_2$ relative to the time required for incorporating puromycin into cellular proteins (FIGS. 12 and 13). Puromycin serves as a positive control representing the fully deprotected product of Peroxymycin-1. Treated cells were then fixed and immunostained with primary α-puromycin antibody and secondary antibody-Alexa Fluor 488 and subsequently imaged by confocal fluorescence microscopy. Puromycin-treated cells revealed strong green fluorescence within 0.5 h with saturation at 1 h (FIG. 13), suggesting fast uptake and incorporation of puromycin into cellular proteins. In contrast, Peroxymycin-1-treated cells show no significant green fluorescence at 0.5 h, but we were pleased to observe increases in fluorescence intensity at longer time points from 1 to 6 h (FIG. 12), presumably due to reaction of the probe with $H_2O_2$ followed by incorporation of the puromycin product into nascent cellular peptides. The statistically significant "turn-on" of the green fluorescence from cells treated with Peroxymycin-1 (FIG. 12) suggests that this reagent is sensitive enough to detect basal levels of $H_2O_2$ in cell culture.

To compare the sensitivity of this new histochemical method to a fluorescent probe counterpart, we treated HeLa cells with Peroxyfluor-2 (PF2), a boronate probe with negligible background in the absence of $H_2O_2$ owing to its closed lactone structure that shows strong green fluorescence upon reaction with $H_2O_2$(Dickinson, et al. *J. Am. Chem. Soc.* 2010, 132, 5906). HeLa cells treated with 10 µM PF2 for 0.5, 4 and 6 h and washed display negligible fluorescence (FIG. 12B), suggesting that this reagent is not sensitive enough to detect basal $H_2O_2$ levels in HeLa cells under these conditions. We suggest that the higher sensitivity of Peroxymycin-1 over PF2 comes from two main origins. First, covalent staining for the histochemical Peroxymycin-1 reagent can lead to a permanent mark that survives sample washing and fixation, as opposed to PF2 and other fluorescent dyes where probe leakage can decrease signal-to-noise responses (Clark, et al. *Anal. Chem.* 1999, 71, 4837). Second, immunostaining offers advantages of low background noise owing to specific interactions from antibodies and higher signal due to the potential for multivalent binding of secondary antibody-dye conjugates onto the primary antibody. Taken together, the data show that Peroxymycin-1 exhibits excellent sensitivity for cellular detection of $H_2O_2$.

Figure 14:
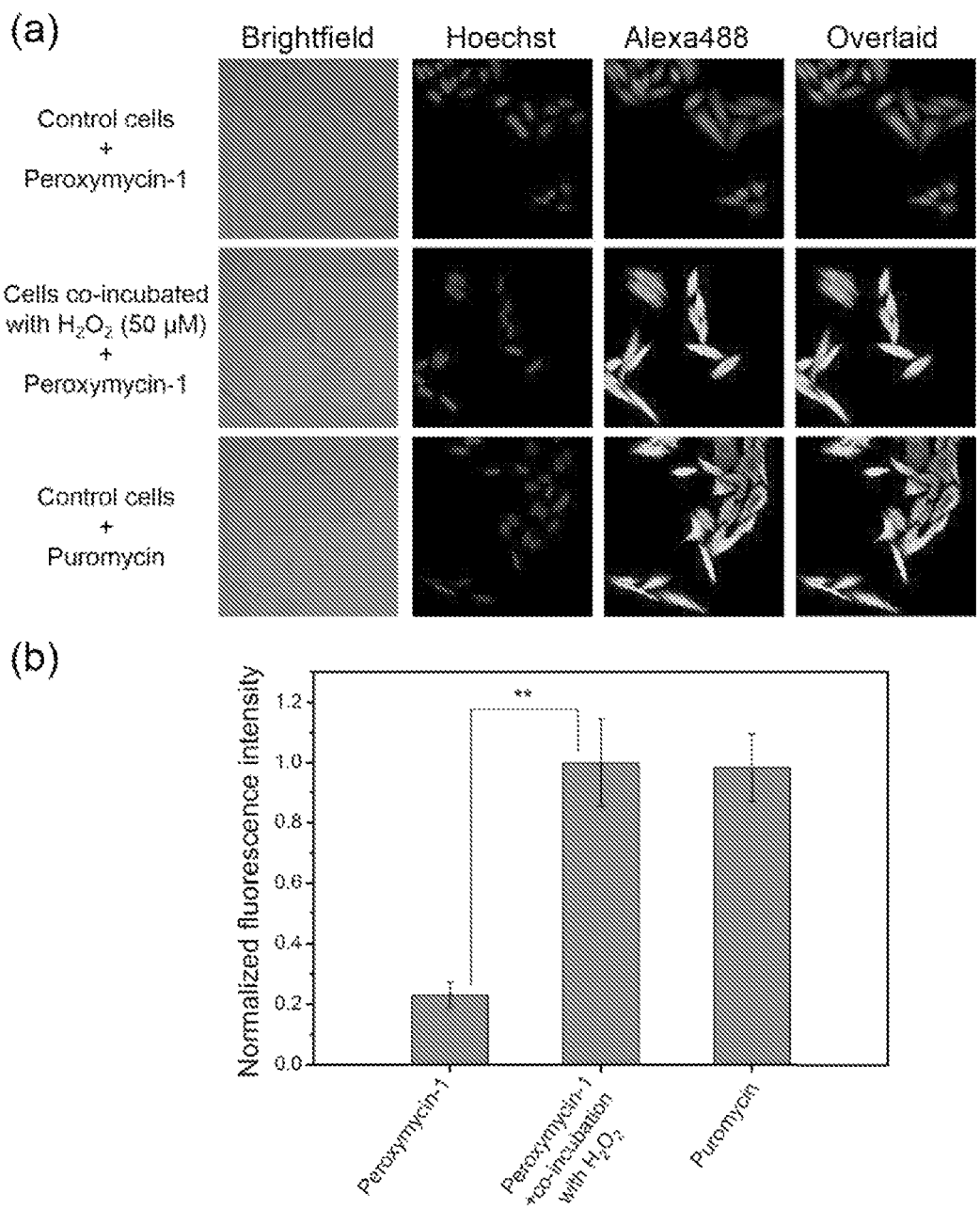
FIG. 14A shows confocal fluorescence microscopy images of HeLa cells stained with Peroxmycin-1 and puromycin (1 µM), respectively, for 4 h, with or without co-incubation with $H_2O_2$ (50 µM) for the last 2 h. The cells were then washed, fixed, stained and imaged. All the images were recorded using the same imaging parameters with the Alexa488 channel.
FIG. 14B shows cellular fluorescence intensities of the HeLa cells as determined by ImageJ. All the data are shown as mean±SEM. (n=5; ** denoted p<0.01).

The readiness of the reaction between Peroxymycin-1 and $H_2O_2$ in vitro was further studied by co-incubation of HeLa cells with Peroxymycin-1 and $H_2O_2$ for 2 h (FIG. 14). The cells co-incubated with Peroxymycin-1 and $H_2O_2$ were found to show similar fluorescence intensity to those treated with puromycin, and the fluorescence intensity was 4.3 times higher than that from cells treated with Peroxymycin-1 only (FIG. 14). This indicates a fast and clean conversion of Peroxymycin-1 into puromycin by $H_2O_2$ and readily incorporation of the generated puromycin into cellular proteins in vitro.

Figure 15:
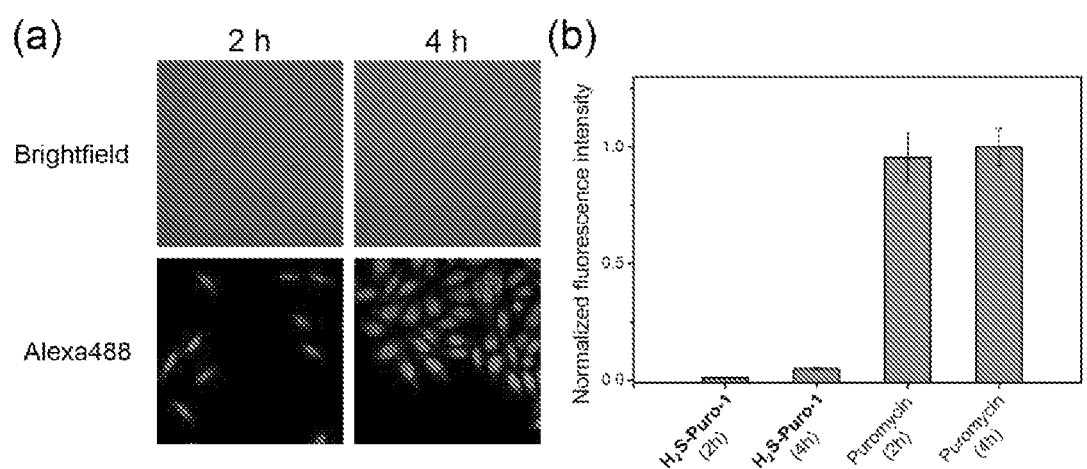
FIG. 15A shows confocal fluorescence microscopy images of HeLa cells stained with $H_2S$-Puro-1 (1 µM) for indicated time intervals. The cells were then washed, fixed, stained and imaged.
FIG. 15B shows normalized cellular fluorescence intensities of the $H_2S$-Puro-1-treated HeLa cells by that of the puromycin-treated cells. All the data are shown as mean±SEM. (n=5).

HeLa cells treated with $H_2S$-Puro-1, fixed and immunostained also revealed time-dependent increase in green fluorescence intensity (FIG. 15). However, the intensity was only around 5% from that of cells treated by puromycin after 4 h incubation. This value was significantly lower than the relative fluorescence intensity of cells treated by peroxymycin for the same time interval (30.5% relative to the intensity from cells treated by puromycin). Such lower relative fluorescence intensity can be ascribed to the difference in intracellular concentrations of $H_2S$ and $H_2O_2$, and more importantly, the difference in reaction rates of $H_2S$-Puro and Peroxymycin-1 with their substrates. The slower reaction of $H_2S$-Puro-1 with $H_2S$, as indicated by the pseudo first-order reaction rate constant determined by LC-MS experiment, led to release of fewer puromycin molecules and hence slower "turn-on" of green immunofluorescence from the treated cells. Nonetheless, the immunofluorescence from $H_2S$-Puro-1-treated HeLa cells was still strong enough to be imaged by confocal fluorescence microscopy, suggesting that $H_2S$-Puro-1 is sensitive enough to detect basal $H_2S$ level in vitro.

Figure 16:
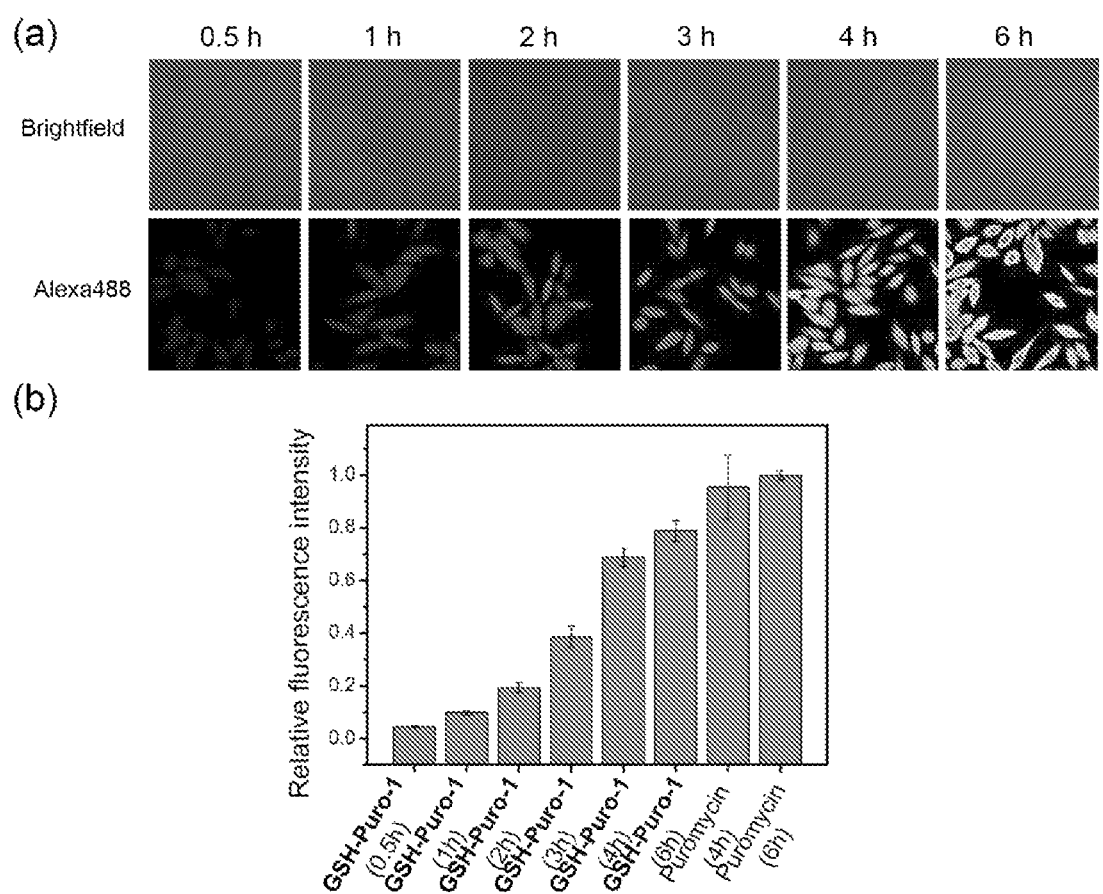
FIG. 16A shows confocal fluorescence microscopy images of HeLa cells treated with GSH-Puro-1 (1 µM) for indicated time intervals. The cells were then washed, fixed, stained and imaged.
FIG. 16B shows normalized cellular fluorescence intensities of the GSH-Puro-treated HeLa cells by that of the puromycin-treated cells. All the data are shown as mean±SEM. (n=5).

Time-dependent increase in immunofluorescence intensity from GSH-Puro-1-treated HeLa cells was found in the confocal fluorescence microscopy images (FIG. 16). It is noteworthy that the relative fluorescence intensity of the cells, as compared to the cells treated by puromycin, was very strong (69 and 79% after 4 ad 6 h incubation respectively). Such significant "turn-on" of green immunofluorescence from GSH-Puro-treated cells can be attributable to the higher GSH concentration (in mM range) than $H_2O_2$ and $H_2S$ (in μM range) under physiologically relevant condition, thus allowing GSH-Puro-1 to react readily with basal GSH level in vitro.

Figure 17:
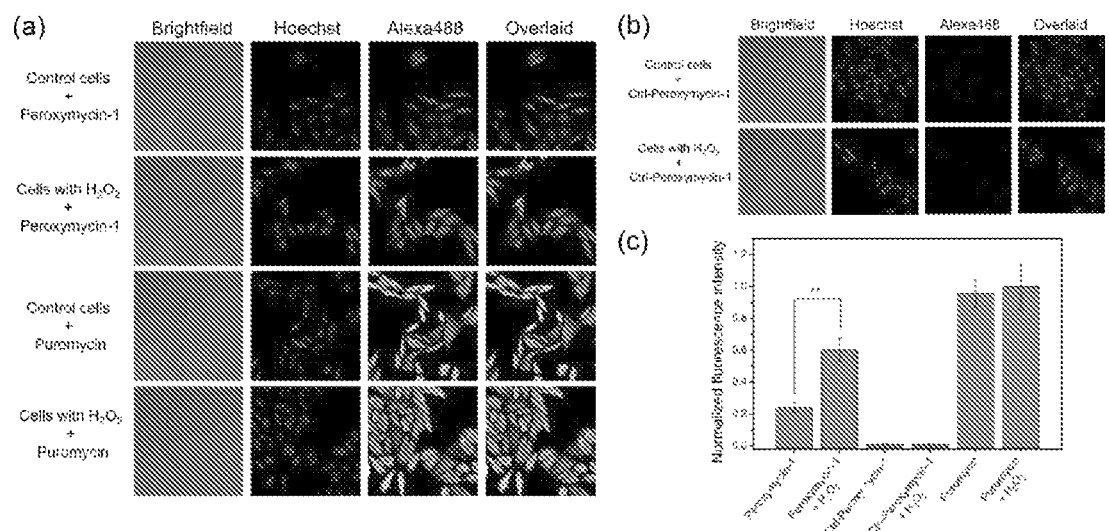
FIG. 17A shows confocal fluorescence microscopy images of HeLa cells, with or without pre-treatment with $H_2O_2$ (50 µM) for 2 h, stained with Peroxmycin-1 and puromycin (1 µM) respectively.
FIG. 17B shows confocal fluorescence microscopy images of HeLa cells treated with Ctrl-Peroxmycin-1 (1 µM) for 4 h. The cells were subsequently washed, fixed, stained and imaged. All the images were recorded using the same imaging parameters with the Alexa488 channel.
FIG. 17C shows cellular fluorescence intensities of the HeLa cells as determined by ImageJ. All the data are shown as mean±SEM. (n=5; ** denoted p<0.01).

Example 5: Peroxmycin-1 and Histochemical Detection of Cellular $H_2O_2$ Under Oxidative Stress or Physiological Stimulation Conditions We next moved on to evaluate the ability of Peroxymycin-1 to respond to changes in $H_2O_2$ levels under oxidative stress conditions. HeLa cells were pretreated with $H_2O_2$ (50 μM) for 2 h and washed before incubation with Peroxymycin-1, Ctrl-Peroxymycin-1, or puromycin (1 μM), respectively, for 4 h. Peroxymycin-1-stained cells exposed to $H_2O_2$ show a clear, statistically significant increase in fluorescence intensity compared to Peroxymycin-1-stained control cells without $H_2O_2$ pretreatment (FIG. 17). On the other hand, neither puromycin-stained cells nor Ctrl-Peroxymycin-1-stained cells show differences in fluorescence intensity when samples are exposed to $H_2O_2$ or mock vehicle (FIG. 17B). Notably, the lack of observed changes in fluorescence intensity with puromycin-stained cells upon $H_2O_2$ addition indicates that ROS treatment does not alter its cellular uptake and incorporation into proteins, whereas the lack of signal from Ctrl-Peroxymycin-1-stained cells shows that there is also no off-target release of puromycin from this reagent. As such, only Peroxymycin-1 is responsive to oxidative stress induced by $H_2O_2$ treatment owing to its ability to react with this ROS and undergo a self-immolative cleavage to release puromycin.

Figure 18:
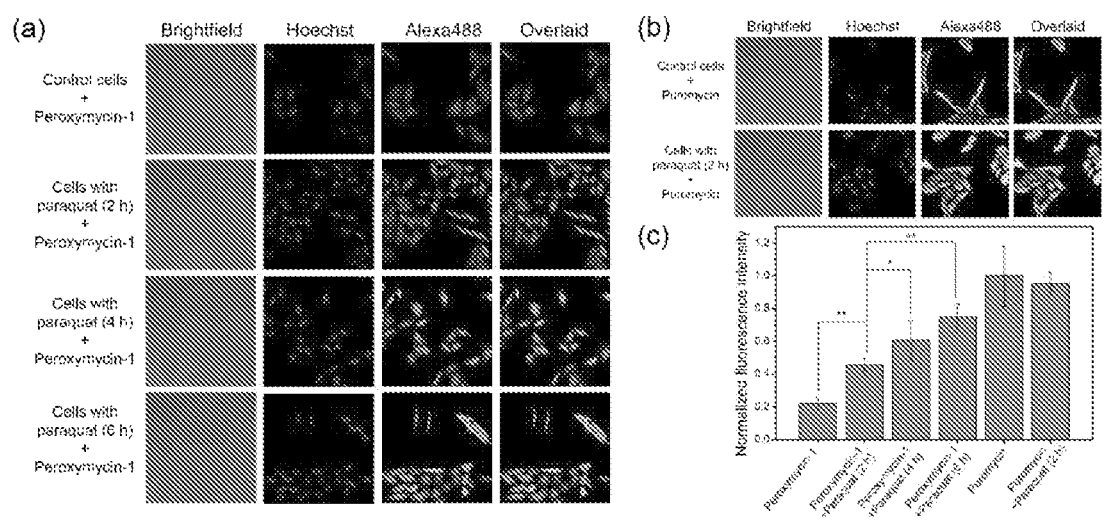
FIGS. 18A and 18B show confocal fluorescence microscopy images of HeLa cells stained with Peroxmycin-1 (1 µM) and puromycin (1 µM), respectively, for 6 h, with or without co-incubation of paraquat (1 mM) for the indicated time intervals. The cells were then washed, fixed, stained and imaged. All the images were recorded using the same imaging parameters with the Alexa488 channel.
FIG. 18C shows cellular fluorescence intensities of the HeLa cells as determined by ImageJ. All the data are shown as mean±SEM (n=5; * and ** denoted p<0.05 and 0.01 respectively).

Next, we utilized Peroxymycin-1 for detection of endogenous $H_2O_2$ production through treatment of HeLa cells with paraquat, a small-molecule inducer of ROS and oxidative stress. HeLa cells co-incubated with Peroxymycin-1 (1 μM) and paraquat (1 mM) showed significant increases in fluorescence intensity compared to Peroxymycin-1-stained control cells without paraquat treatment (FIG. 18). In control experiments, we observed no significant changes in fluorescence between puromycin-stained cells with or without paraquat exposure, showing that Peroxymycin-1 responds to paraquat via ROS detection rather than changes in cellular uptake or puromycin incorporation (FIG. 18). The data establish that Peroxymycin-1 is an effective chemical tool for detection of endogenous $H_2O_2$ production in cells.

Figure 19:
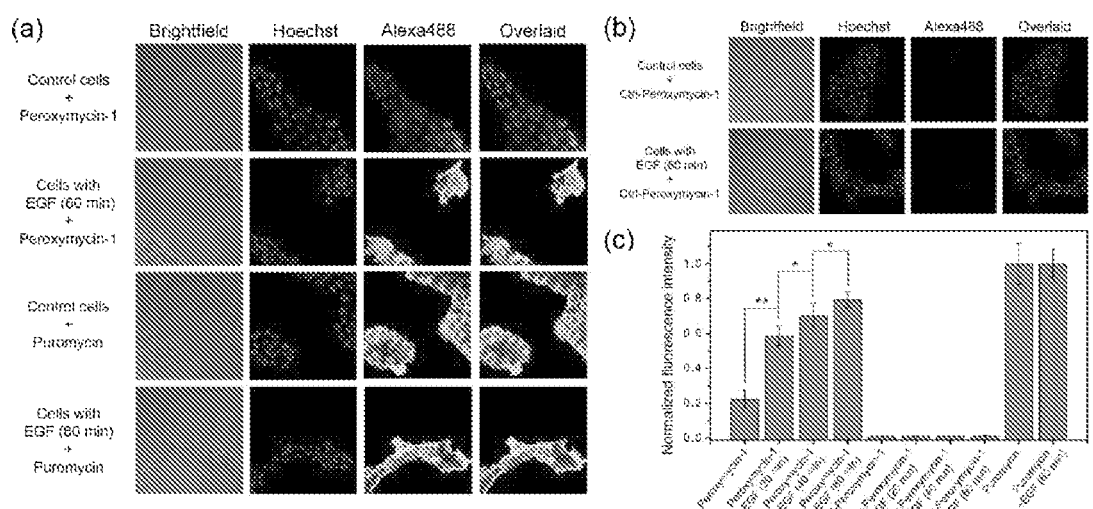
FIG. 19A shows confocal fluorescence microscopy images of A431 cells, stained with Peroxmycin-1 or puromycin (1 µM), with or without pretreatment with EGF (100 ng/mL) for 60 min.
FIG. 19B shows images of A431 cells treated with Ctrl-Puro (1 µM) for 4 h. The cells were then washed, fixed, stained and imaged. All the images were recorded using the same imaging parameters with the Alexa488 channel.
FIG. 19C shows cellular fluorescence intensity of the HeLa cells as determined by ImageJ. All the data are shown as mean±SEM. (n=5; * and ** denoted p<0.05 and 0.01 respectively).

Peroxymycin-1 was then used to detect changes in cellular $H_2O_2$ levels upon physiological stimulation under signaling conditions. A431 cells possess a high expression of epidermal growth factor receptors (EGFR), and thus can respond to EGF stimulation for endogenous generation of $H_2O_2$ through an Nox/PI3K pathway (Dickinson, et al. J. Am. Chem. Soc. 2010, 132, 5906). A431 cells were stimulated with EGF (100 ng/mL) for 20, 40, and 60 min, and then washed and incubated with Peroxymycin-1 (1 μM) for 4 h (FIG. 19). EGF stimulation triggers a statistically significant increase in fluorescence intensity with increasing EGF incubation times. On the other hand, Ctrl-Peroxymycin-1-stained A431 cells with or without EGF stimulation revealed no observable differences in immunofluorescence, indicating that this probe does not give off-target production of puromycin (FIGS. 19B and 19C). As another control, puromycin-stained cells with or without EGF stimulation also do not show any significant changes in fluorescence intensity, again ruling out any alterations in rates of cellular uptake and puromycin incorporation with EGF exposure (FIGS. 19A and 19C). Indeed, the collective results establish that Peroxymycin-1 allows imaging of changes in intracellular $H_2O_2$ levels under both stress and signaling conditions.

Figure 20:
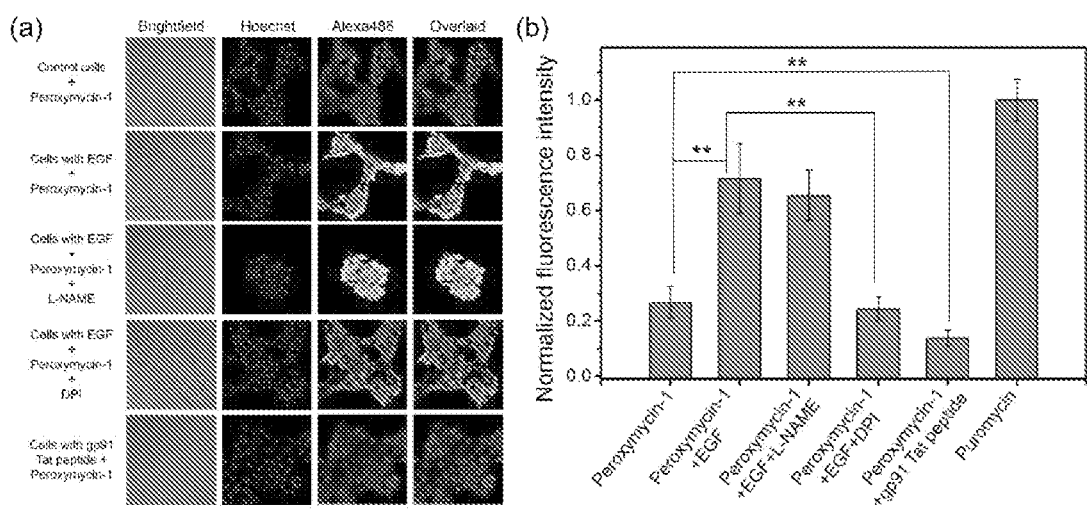
FIG. 20A shows confocal fluorescence microscopy images of A431 cells with or without EGF stimulation (100 ng/mL) for 40 min and with or without various Nox or NO synthase inhibitors, followed by washing and incubation with Peroxymycin-1 (1 µM) for 4 h. The cells were then washed, fixed, stained and imaged. All the images were recorded using the same imaging parameters with the Alexa488 channel.
FIG. 20B shows cellular fluorescence intensities of the HeLa cells as determined by ImageJ. All the data are shown as mean±SEM. (n=5; ** denoted p<0.01).

To further validate that the increases in cellular immunofluorescence observed using Peroxymycin-1 in this EGF/A431 cell model are due to $H_2O_2$ and not peroxynitrite or related reactive nitrogen species (RNS), control experiments were performed wherein A431 cells were pretreated with the nitric oxide (NO) synthase inhibitor, L-$N^G$-nitroarginine methyl ester (L-NAME; 100 μM; 25 min) (Miller, et al. Nat. Chem. Biol. 2007, 3, 263) along with EGF (100 ng/mL; 40 min), washed, incubated with Peroxymycin-1 (1 μM) for 4 h and then imaged (FIG. 20). Inhibition of NO generation blocks formation of peroxynitrite and other RNS. Therefore, A431 cells pretreated with L-NAME and EGF should show elevated $H_2O_2$ levels but not peroxynitrite levels. Indeed, inhibition with L-NAME does not block EGF-stimulated increases in Peroxymycin-1 immunofluorescence (FIG. 20), showing that the probe selectively detects elevations in $H_2O_2$ level without any peroxynitrite interference under these biological conditions.

To identify the molecular source of $H_2O_2$ production upon EGF stimulation, A431 cells were treated with EGF (100 ng/mL; 40 min) in the presence of the broad-spectrum Nox inhibitor diphenyleneiodonium (DPI; 5 μM). Peroxymycin-1-stained, EGF-stimulated A431 cells show a statistically significant decrease in immunofluorescent signal with DPI incubation (FIG. 20), establishing that Nox is responsible for the physiological $H_2O_2$ burst in this cell model.

Figure 21:
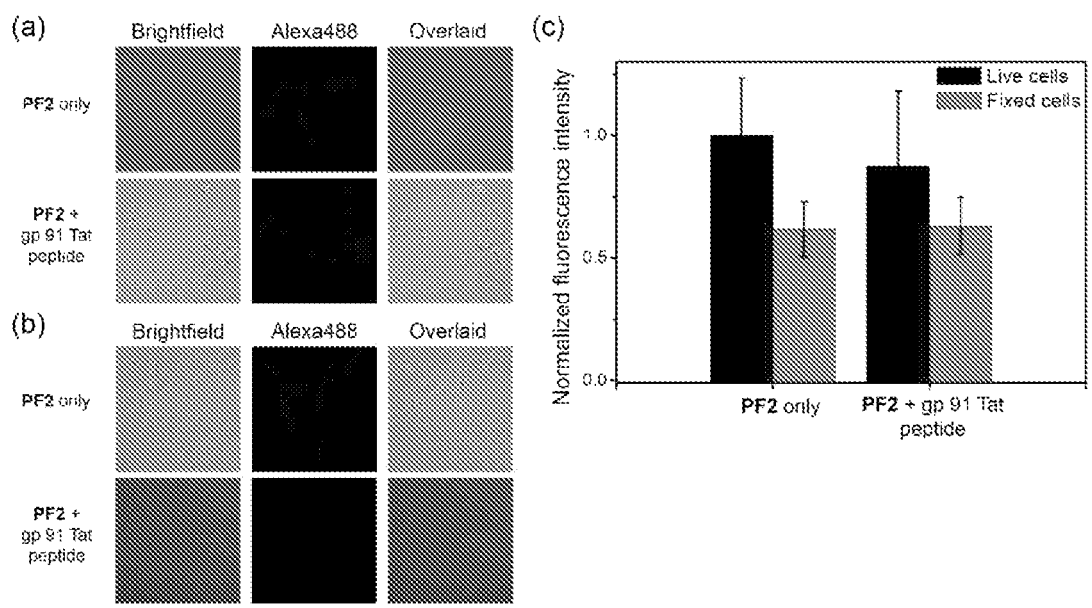
FIG. 21 shows confocal fluorescence microscopy images of HeLa cells, without pre-treatment or with pre-treatment with gp91 Tat peptide (100 µM) for 30 min and subsequent washing by PBS, stained with PF2 (10 µM) for 4 h.

Finally, with the high selectivity and sensitivity of $H_2O_2$ established for Peroxymycin-1 for use in histochemical celluar assays, we sought to utilize this reagent for imaging basal $H_2O_2$ production derived from Nox. To this end, A431 cells were pretreated with gp91 Tat peptide (100 μM; 30 min) (Miller, et al. Nat. Chem. Biol. 2007, 3, 263), an isoform-specific inhibitor of Nox2 that can suppress $H_2O_2$ production, and then stained with Peroxymycin-1 (1 μM; 4 h). Indeed, gp91 Tat peptide-treated cells exhibit markedly lower levels of Peroxymycin-1 immunofluorescence compared to controls without inhibitor treatment (FIG. 20). For comparison, the fluorescent $H_2O_2$ probe PF2 failed to show statistically significant decreases in signal in response to Nox2 inhibition by the gp91 Tat peptide (FIG. 21), again illustrating that this histochemical approach affords improved sensitivity through enabling permanent staining of the cells in response to $H_2O_2$ with low background noise and improved multivalent signal through immunostaining.

Example 6: Histochemical Detection of Exogenous and Endogenous $H_2S$

Figure 22:
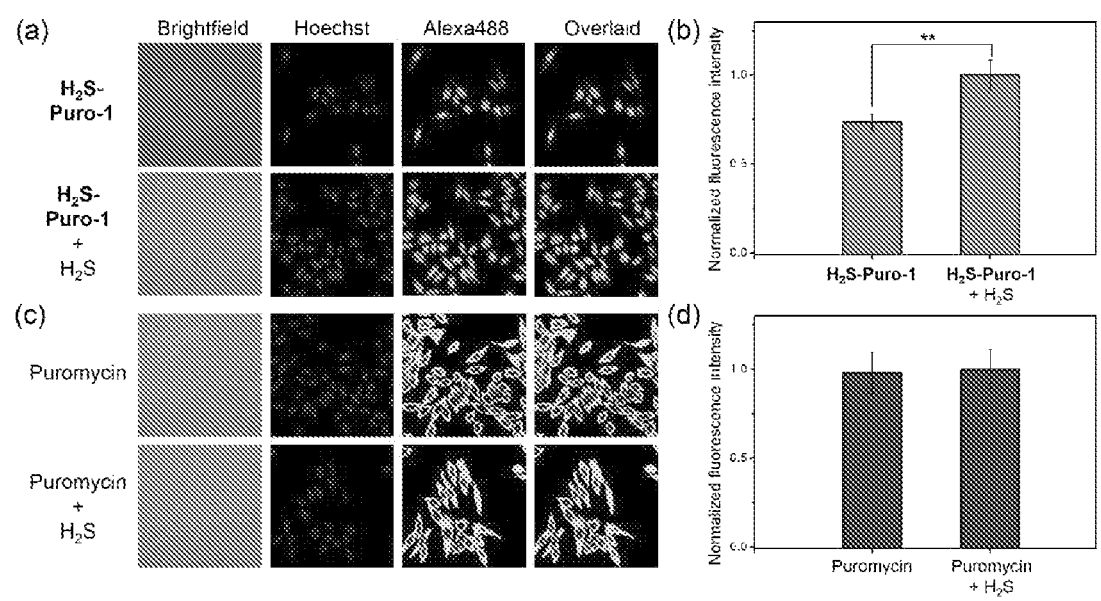
FIG. 22A shows confocal fluorescence microscopy images of HeLa cells, with pre-treatment with $H_2S$ (100 µM) in PBS for 30 min or without pre-treatment, stained with $H_2S$-Puro-1 (1 µM) for 4 h. The cells were then washed, fixed, stained and imaged. All the images were recorded using the same imaging parameters.
FIG. 22B shows cellular fluorescence intensities of the $H_2S$-Puro-1-treated cells as determined by ImageJ. All the data are shown as mean±SEM. (n=5; ** denoted p<0.01).
FIG. 22C shows confocal fluorescence microscopy images of HeLa cells, with or without pre-treatment with $H_2S$, stained with puromycin (1 µM) for 4 h. All the images were recorded using the same imaging parameters.
FIG. 22D shows cellular fluorescence intensities of the puromycin-treated cells as determined by ImageJ (n=5).

HeLa cells pretreated with $H_2S$ (100 μM; 30 min) were incubated with $H_2S$-Puro-1 (1 μM) for 4 h, and were found to show stronger immunofluorescence than cells without pretreating with $H_2S$ (1.4-fold; FIG. 22). No significant change in immunofluorescence intensity from puromycin-treated cells was found by the $H_2S$ pretreatment (FIGS. 22C and 22D), indicating that the pretreatment with $H_2S$ would not significantly alter cellular uptake rate and puromycin incorporation rate. As a result, the stronger immunofluorescence from $H_2S$-Puro-1-treated cells with $H_2S$ pretreatment should be ascribed to the increase in exogenous $H_2S$ level in the pretreated cells, leading to faster release of puromycin from $H_2S$-Puro.

Figure 11:
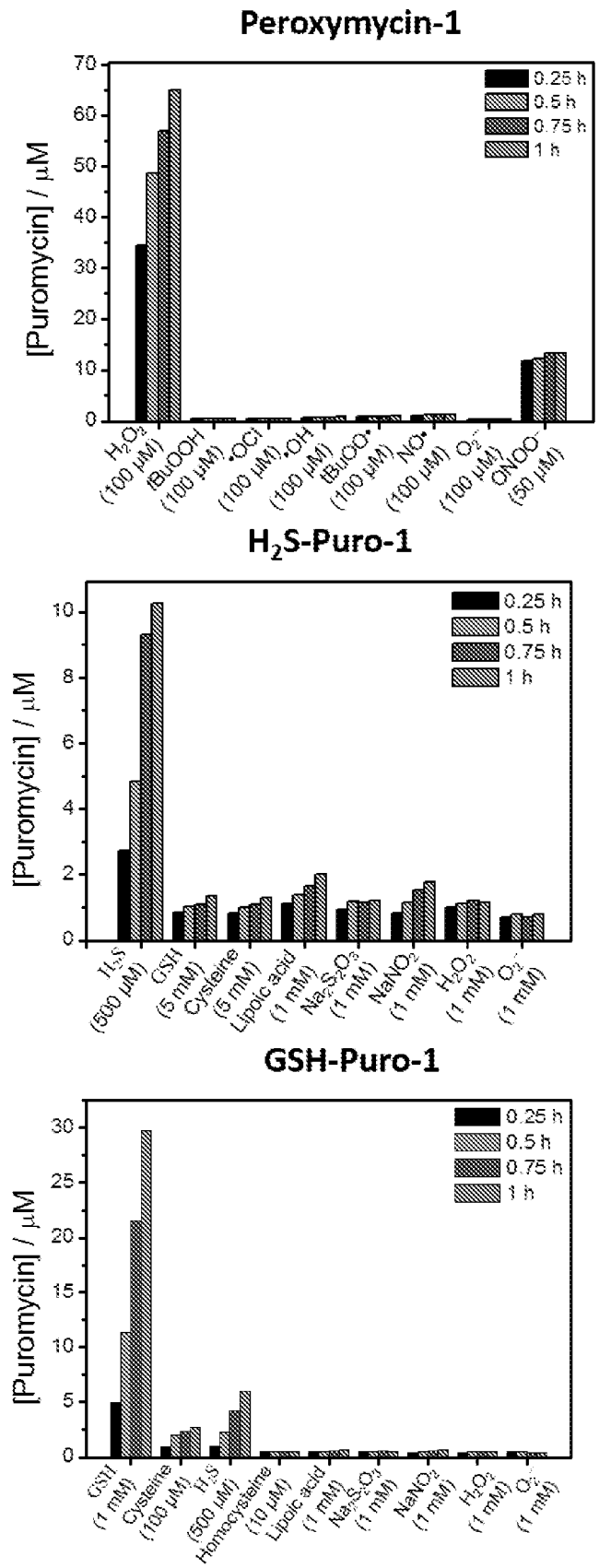
FIG. 11 shows selectivity of the puromycin-based probes (0.3 mM) in phosphate buffer (20 mM, pH 7.4)-methanol solution mixture (2:1, v/v) with 3 vol % DMSO toward target analytes over other substrates.
Figure 23:
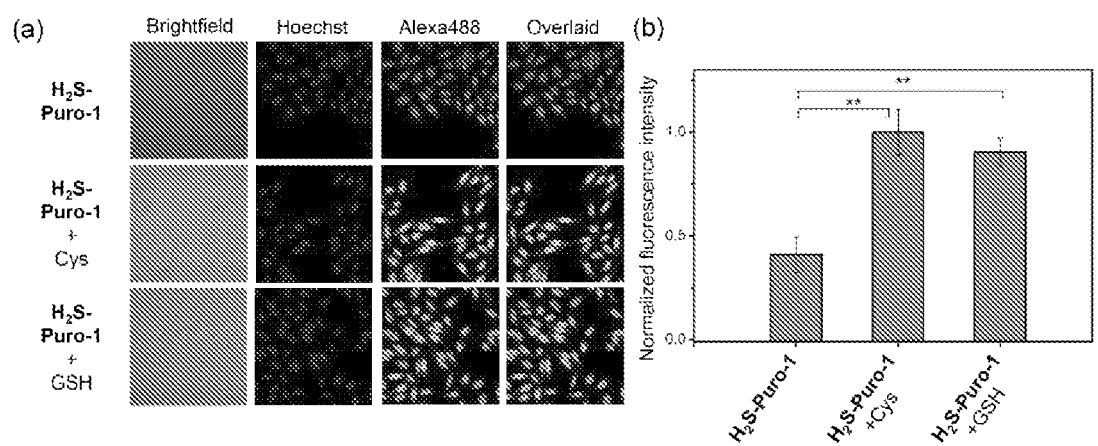
FIG. 23A shows confocal fluorescence microscopy images of HeLa cells stained with $H_2S$-Puro-1 (1 µM) for 4 h, with co-incubation with cysteine (100 µM) or glutathione (100 µM). The cells were then washed, fixed, stained and imaged. All the images were recorded using the same imaging parameters.
FIG. 23B shows normalized cellular fluorescence intensities of the HeLa cells as determined by ImageJ. All the data are shown as mean±SEM. (n=5; ** denoted p<0.01).
Figure 24:
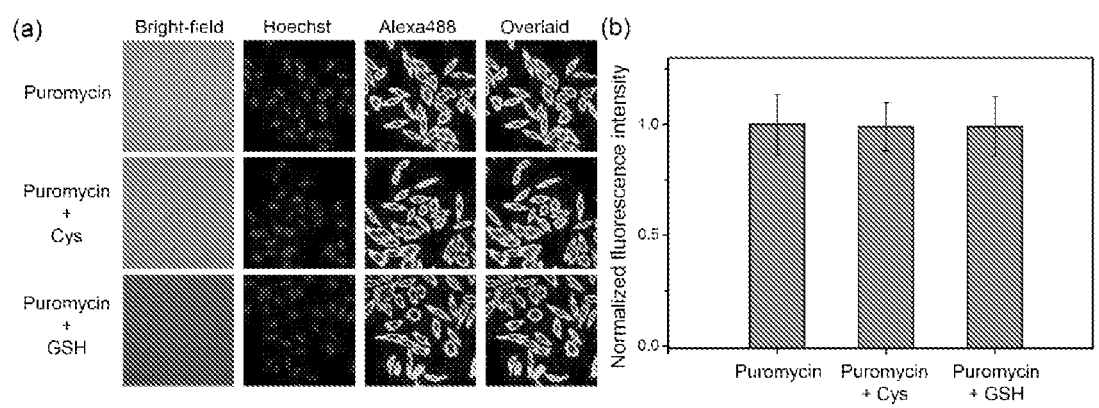
FIG. 24A shows confocal fluorescence microscopy images of HeLa cells stained with puromycin (1 µM) for 4 h, with co-incubation with cysteine (100 µM) or glutathione (100 µM). The cells were then washed, fixed, stained and imaged. All the images were recorded using the same imaging parameters.
FIG. 24B shows normalized cellular fluorescence intensities of the HeLa cells as determined by ImageJ. All the data are shown as mean±SEM. (n=5; ** denoted p<0.01).

The ability of H$_2$S-Puro-1 to image endogenous H$_2$S production was also studied. HeLa cells incubated with H$_2$S-Puro (1 µM) and cysteine or GSH (100 µM) for 4 h were found to show a significant increase in immunofluorescence intensity as compared to the cells without incubation with cysteine/GSH (FIG. 23). Control experiments on cells treated with puromycin and cysteine or GSH showed negligible change in fluorescence intensity (FIG. 24), suggesting that no significant change in cellular uptake rate and puromycin incorporation rate by treating cells with cysteine or GSH. As LC-MS experiments showed that no significant release of free puromycin from H$_2$S-Puro-1 even in the presence of high concentrations of cysteine or GSH (5 mM; FIG. 11), the increase in immunofluorescence intensity from treated cells should not be owing to the direct reaction of H$_2$S-Puro with cysteine/GSH. Instead, cystathionine γ-lyase (CSE) and cystathionine β-synthase (CBS) are two enzymes that can utilize cysteine as substrate for H$_2$S biogenesis (Lin, et al. *Chem. Soc. Rev.* 2015, 44, 4596). GSH can be degraded extracellularly by γ-glutamyl transpeptidase with the generation of H$_2$S (Bae, et al. *J. Am. Chem. Soc.* 2013, 135, 9915). Therefore, incubation of HeLa cells with cysteine and GSH should lead to an increase in endogenous H$_2$S level. This would result in faster specific reaction between H$_2$S-Puro and H$_2$S, leading to the formation of more puromycin molecules and hence the treated cells showed stronger immunofluorescence. These experiments indicate that H$_2$S-Puro-1 can sensitively probe changes in endogenous H$_2$S level in vitro.

Figure 25:
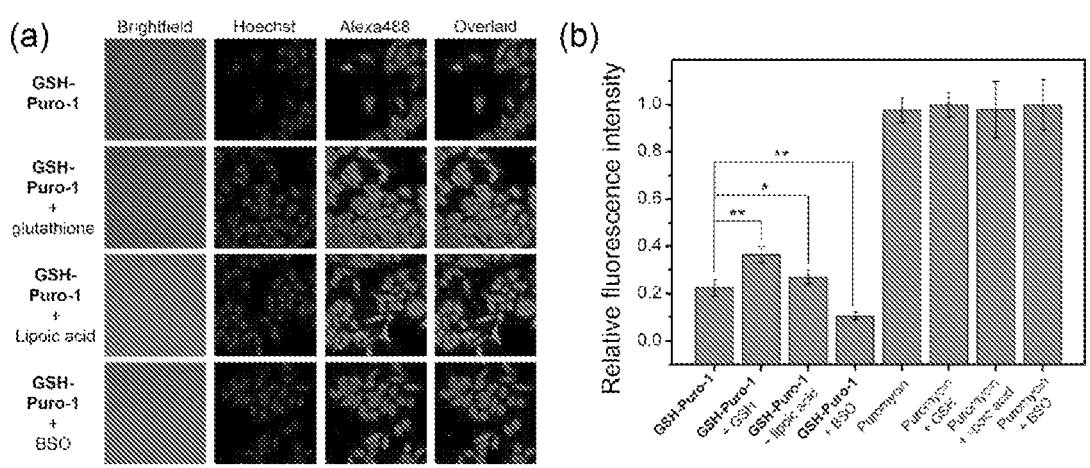
FIG. 25A shows confocal fluorescence microscopy images of HeLa cells pretreated with GSH (100 µM, 24 h), lipoic acid (1.8 mM, 24 h) or BSO (1 mM, 3 h), and then stained with GSH-Puro-1 (1 µM) for 2 h. The cells were then washed, fixed, stained and imaged. All the images were recorded using the same imaging parameters.
FIG. 25B shows normalized cellular fluorescence intensities of the HeLa cells as determined by ImageJ. All the data are shown as mean±SEM. (n=5; ** denoted p<0.01).

Example 7: Histochemical Detection of GSH Under Physiological Stimulation or Inhibition Conditions HeLa cells pretreated with GSH (100 µM, 24 h) or lipoic acid (1.8 mM, 24 h), followed by incubation with GSH-Puro-1 for 2 h displayed stronger immunofluorescence than cells without pretreatment (FIG. 25). On the other hand, cells pretreated with buthionine sulfoximine (BSO; 1 mM, 3 h) and incubated with GSH-Puro-1 for 2 h showed significantly weaker fluorescence than cells without pretreatment (FIG. 25). As there is no significant change in immunofluorescence intensity from puromycin-treated cells with or without pretreatment (FIG. 25), the pretreatment with GSH, lipoic acid and BSO should not cause significant alteration of cellular uptake rate and puromycin incorporation rate. Therefore, the increase in immunofluorescence intensity from GSH-Puro-1-treated cells with GSH pretreatment was likely caused by an increase in exogenous GSH level. On the other hand, since lipoic acid has been reported to stimulate GSH biosynthesis by improving cystine utilization (Packer, et al. *Free Radical Biol. Med.* 1997, 22, 359) and BSO is known to be an inhibitor of GSH biosynthesis (Mari, et al. *Free Radicals Biol. Med.* 2002, 32, 73), the stronger and weaker immunofluorescence from pretreated cells with lipoic acid and BSO, respectively, should be attributable to the stimulation and inhibition of endogenous GSH production. As a result, these experiments demonstrate that GSH-Puro-1 is capable of sensitive detection of changes in exogenous and endogenous GSH.

Example 8: Peroxymycin-1 and H$_2$O$_2$ Profiling Across Multiple Cell Types

Figure 26:
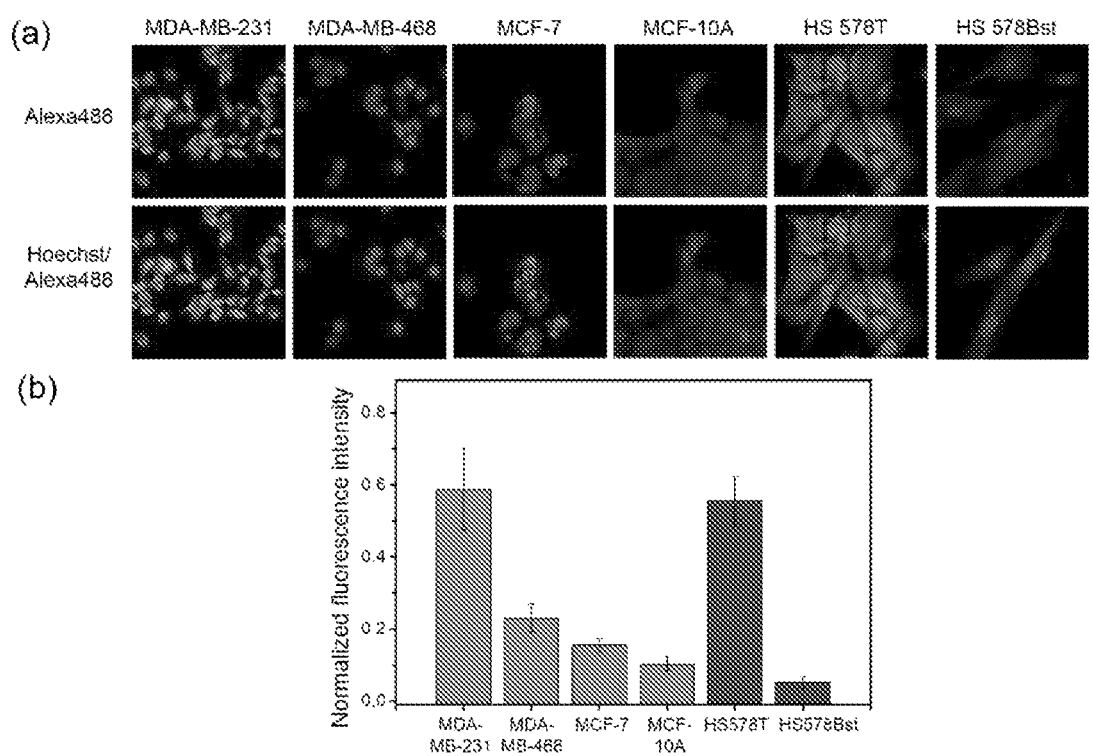
FIG. 26A shows confocal fluorescence microscopy images of normal breat cells (HS 578Bst), non-tumorigenic breast epithelial cells (MCF-10A), breast cancer cells (MDA-MB-468 and MCF-7), invasive breast cancer cells (HS 578T) and highly metastatic breast cancer cells (MDA- MB-231) assayed with Peroxmycin-1 (1 μM) for 4 h. The cells were subsequently washed, fixed, stained and imaged. All the images were recorded using the same imaging parameters.
FIG. 26B shows fluorescence intensities from cells treated with Peroxymycin-1 normalized by fluorescence intensities from cells treated with puromycin as an internal standard (n=5).
Figure 27:
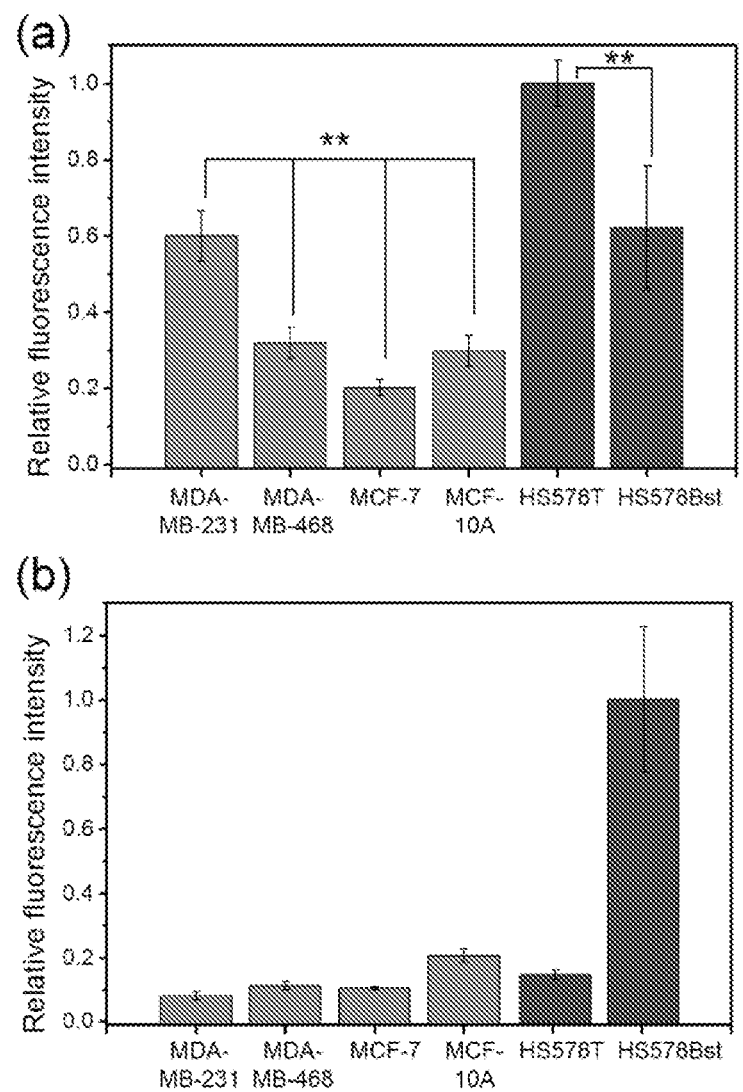
FIGS. 27A and 27B show fluorescence intensities from cells treated by Peroxmycin-1 and puromycin (1 μM) respectively, for 4 h. All the data are shown as mean±SEM. (n=5; ** denoted p<0.01).
Figure 28:
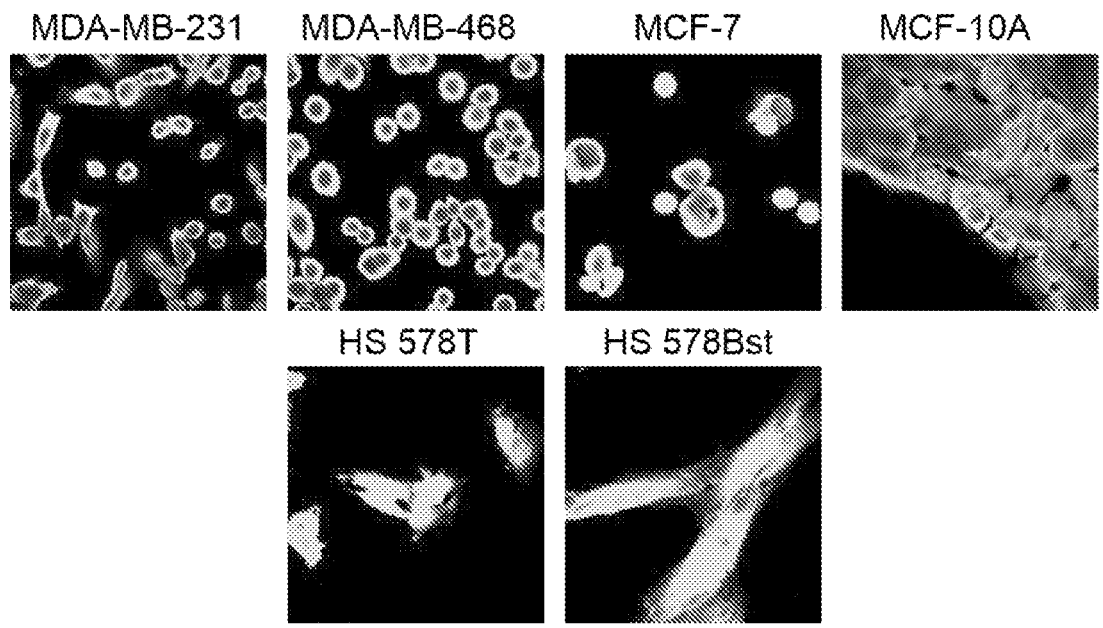
FIG. 28 shows confocal fluorescence microscopy images of breast normal cells (HS 578Bst), non-tumorigenic breast epithelial cells (MCF-10A), breast cancer cells (MDA-MB-468 and MCF-7), invasive breast cancer cells (HS 578T) and highly metastatic breast cancer cells (MDA-MB-231) treated with puromycin (1 μM) for 4 h. The cells were then washed, fixed, stained and imaged. All the images were recorded using the same imaging parameters.

The high sensitivity and selectivity of the histochemical approach to H$_2$O$_2$ detection enabled by Peroxymycin-1 can be exploited to profile levels of this ROS across a panel of cell types. In this context, elevated levels of ROS in cancer can contribute to cell growth, proliferation and migration in this disease, and the ability to assess relative ROS levels across related but distinct types of cells can help characterize and correlate this biochemical marker with key oncogenic properties such as metastatic potential. To achieve this goal, we sought to profile H$_2$O$_2$ levels across a panel of related cancer and non-tumorigenic breast cell lines. These lines include highly metastatic breast cancer (MDA-MB-231), invasive breast cancer (HS 578T), less-invasive breast cancer (MDA-MB-468 and MCF-7), non-tumorigenic breast epithelial (MCF-10A) and normal breast cell (HS 578Bst) models. Samples of each of these cell lines were labeled with Peroxymycin-1 (1 µM) for 4 h, immunostained, and imaged (FIG. 26-28). A correlation between H$_2$O$_2$ levels and metastatic potential was observed, as the highly metastatic MDA-MB-231 cell lines showed higher H$_2$O$_2$-dependent fluorescence intensities compared to less invasive MDA-MB-468 and MCF-7 and non-tumorigenic MCF-10A cells (p<0.01; FIG. 27). Moreover, for HS 578T and HS 578Bst cells that are derived from primary invasive ductal carcinoma and normal adjacent tissues, respectively, the former cell line exhibited a higher fluorescence intensity (FIG. 27A). To normalize for potential differences in cell size and puromycin incorporation rate across this panel of cell lines, control experiments were conducted with puromycin for the same time interval (FIGS. 27 and 28), these data were used as an internal standard for the Peroxymycin-1-stained cells. Indeed, these normalized fluorescence intensities follow the order of metastatic/invasive cancer cells>cancer cells>non-tumorigenic cells (FIG. 26B), suggesting that metastatic/invasive cancer cells show higher H$_2$O$_2$ level than less invasive cancer cells and non-tumorigenic cells. These imaging results are consistent with chemoproteomics experiments showing higher levels of protein sulfenic acids, which are major initial oxidation products of proteins by H$_2$O$_2$, in metastatic/invasive breast cancer cells relative to healthy control cells, and highlight the potential of this histochemical approach to rapidly assess and compare multiple types of biological specimens in the context of ROS status.

Example 9: Peroxymycin-1 as a Histochemical Probe for Detection of H$_2$O$_2$ in Tissues: Identification of Elevations in Liver Peroxide Levels in a Diet-Induced Model of Non-Alcoholic Fatty Liver Disease (NAFLD)

Figure 29:
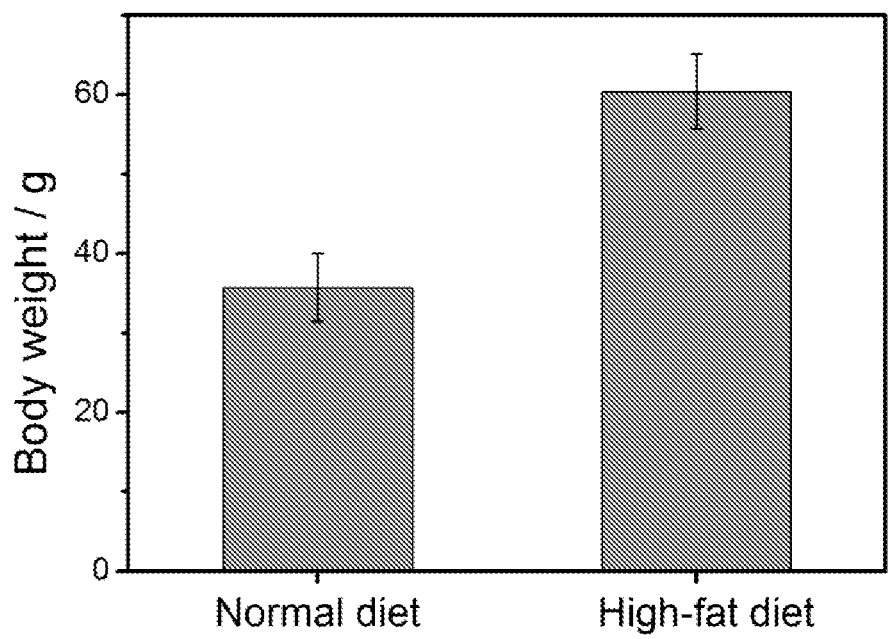
FIG. 29 shows body weight of mice fed with normal chow (NC) or high-fat diet (HFD) monitored at the end of feeding (20 wk).
Figure 30:
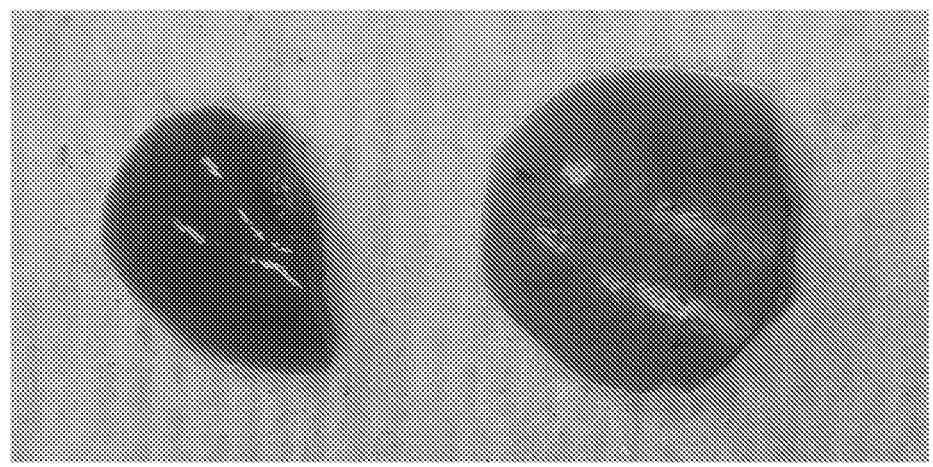
FIG. 30 shows photograph of representative liver tissues harvested from mice fed with normal chow (NC; left) and high-fat diet (HFD; right) respectively, showing ectopic lipid deposition in livers of HFD mice.
Figure 31:
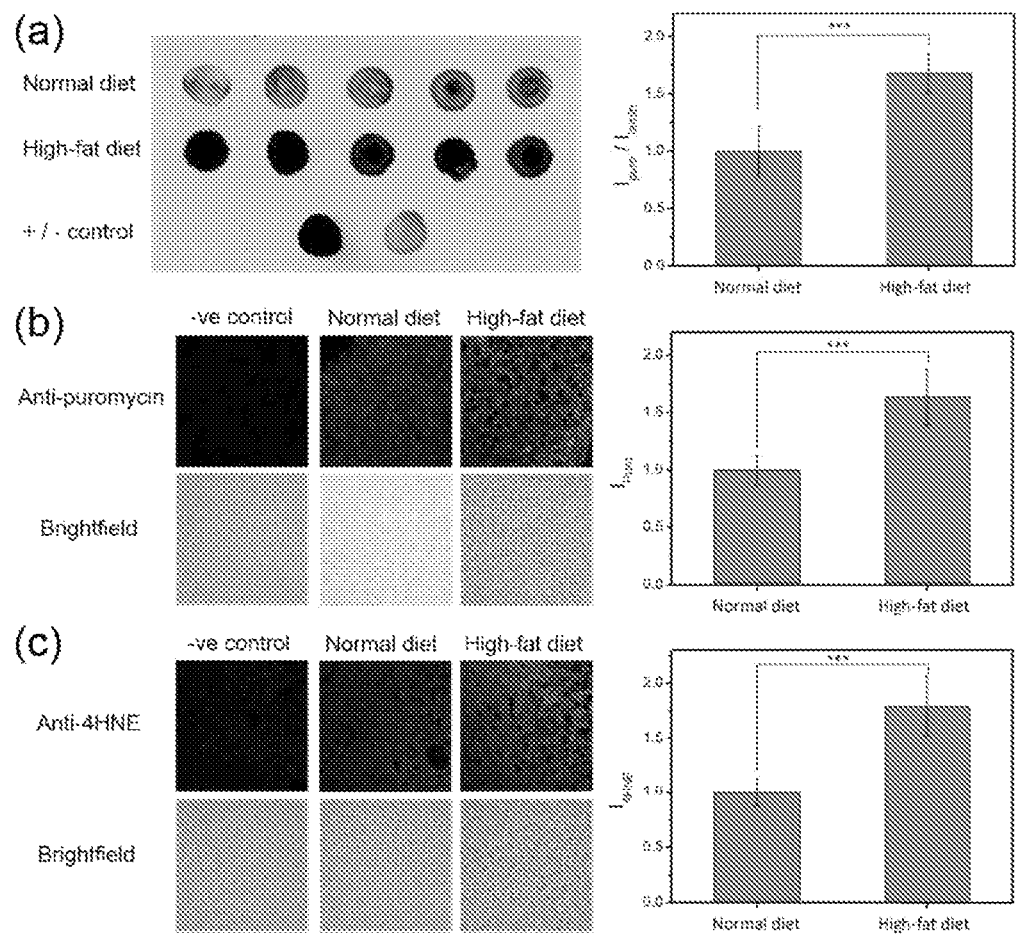
FIG. 31A shows Dot blots of liver tissue lysates from individual normal-chow diet and high-fat diet mice injected with Peroxymycin-1 (10 mg/kg).
FIG. 31B shows immunofluorescence from liver tissues of Peroxymycin-1-treated mice stained with anti-puromycin and anti-mouse-Alexa647 as primary and secondary antibody respectively.
FIG. 31C shows immunofluorescence from liver tissues of Peroxmycin-1-treated mice stained with anti-4-HNE and anti-goat-Alexa647 as primary and secondary antibody respectively. All the data are shown as mean±SEM. (n=5; *** denoted p<0.001).

Technologies to reliably and directly assess ROS levels within intact tissues, and in particular specific individual ROS molecules, remain insufficiently developed. Indeed, one of the most common traditional histochemical assays that is employed to probe ROS and inflammation in tissue biopsies is staining for 4-hydroxy-2-noneal (4-HNE), which is an oxidized lipid metabolite that shows no selectivity toward a particular ROS and thus offers limited and indirect information on overall redox status. As such, the Peroxymycin-1 approach was tested in order to validate its utility for histochemical H$_2$O$_2$ detection from tissue specimens derived from in vivo animal models, particularly during disease development and progression. For the present study, this reagent was applied to a mouse model of non-alcoholic fatty liver disease (NAFLD), as it is the most common liver disease in developed countries and is strongly associated with obesity, diabetes, liver cirrhosis and cancer. In addition, lipid oxidation products such as 4-HNE have been found in fatty liver, providing motivation to develop a complementary method to directly and selectively monitor potential changes in H₂O₂ status during NAFLD onset and progression. To establish a diet-induced NAFLD model with hepatic steatosis, 8-week old male C57BL/6 mice were fed either normal chow (NC) or high fat diet (HFD; 60% kcal from fat, Research Diets D12492) for 20 weeks. A significant increase in body weight of mice fed with HFD, as compared to those fed with NC (FIG. 29), was observed along with ectopic lipid deposition in livers of HFD mice (FIG. 30). Peroxymycin-1 (10 mg/kg) was then introduced to either NC or HFD mice through intraperitoneal injection. The mice were euthanized 4 h after injection and their liver tissues were then harvested. Dot blots of homogenized liver tissue lysates (2 g) from HFD mice injected with Peroxymycin-1 revealed a higher fluorescence ratio for anti-puromycin to anti-lamin B1 staining (the latter was employed for staining nuclear envelop and hence for normalization of total protein spotted) compared to what was observed for NC mice (FIG. 31A), suggesting elevated H₂O₂ levels in liver tissues of HFD mice compared to NC controls. With these results in hand, we moved on to utilize Peroxymycin-1 for histochemical imaging of H₂O₂ in fixed tissue. Liver tissues were fixed, sectioned, immunostained and imaged by confocal fluorescence microscopy. The images obtained show higher fluorescence intensities in the HFD tissue sections compared to NC controls, validating the elevation of H₂O₂ in the NAFLD disease model induced by HFD feeding (FIG. 31B). Negative control experiments without staining primary α-puromycin antibody (FIG. 31B) confirm that immunofluorescence from the tissue samples originates from specific interactions between primary and secondary antibodies. Complementary positive control experiments using 4-HNE staining are also consistent with higher levels of global oxidation in liver tissues from HFD mice (FIG. 31C). Taken together, these results identify that HFD feeding can trigger an increase in H₂O₂ in the liver and establish Peroxymycin-1 as a unique chemical tool for directly assessing H₂O₂ pools with high selectivity and sensitivity in a broad range of cell and tissue specimens While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (I):

P-L-T  (I)

wherein:

P is a puromycin detectable moiety;

L is a self-immolative linker; and

T is an analyte-responsive group configured to trigger cleavage of L and release P upon contact with a target analyte, wherein the puromycin detectable moiety is:

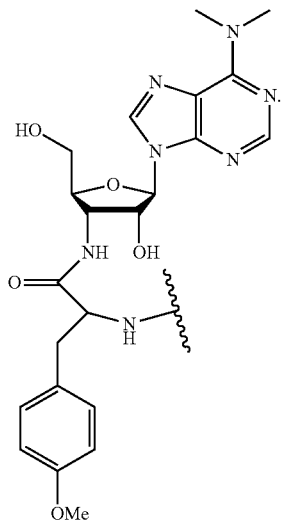

2. The compound of claim 1, wherein L comprises one or more of the following linking groups:

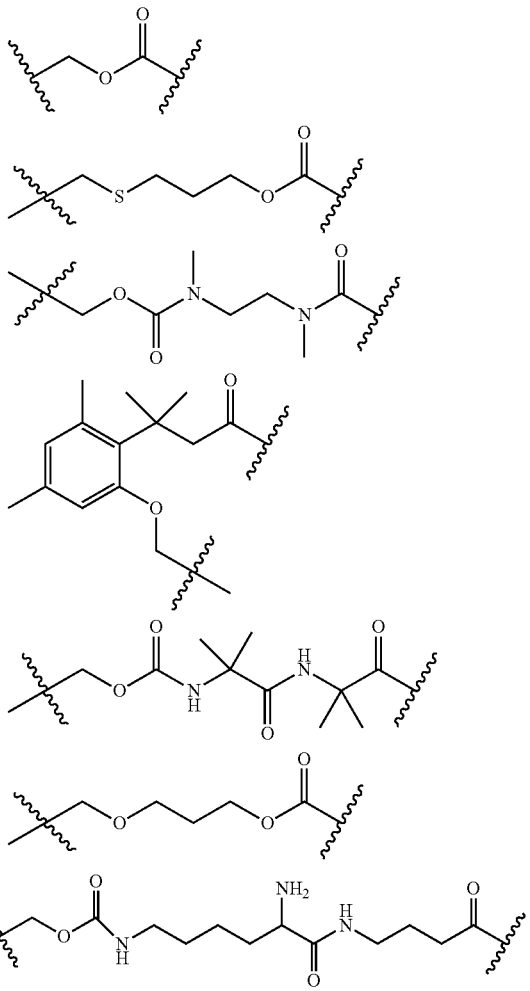

-continued

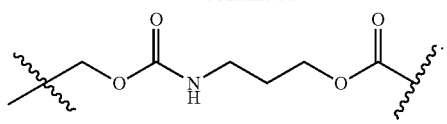

3. The compound of claim 1, wherein T comprises a reactive oxygen species (ROS)-responsive trigger group, a reactive carbonyl species (RCS)-responsive trigger group, a reactive sulfur species (RSS)-responsive trigger group, a ROS scavenger-responsive trigger group or a trigger group for a redox-active metal ion.

4. The compound of claim 1, wherein T comprises:

a) a ROS-responsive trigger group selected from the following:

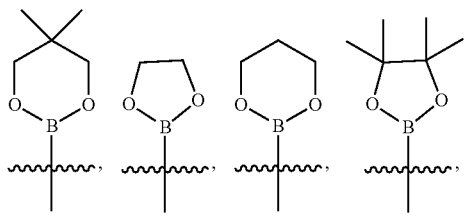

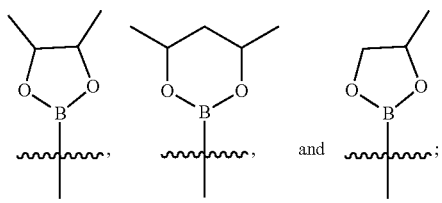 and b) a RCS-responsive trigger group of the formula:

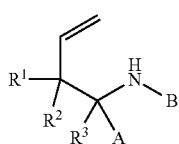

wherein:

$R^1$, $R^2$, $R^3$, A and B are each independently selected from hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido; and wherein A is linked to the puromycin detectable moiety; and wherein A and B are optionally cyclically linked;

c) a RSS-responsive trigger group that comprises an aryl azide or a heteroaryl azide;

d) a ROS scavenger-responsive trigger group that comprises a disulfide group of the formula:

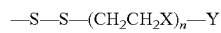

wherein:

n is 0 to 20;

X is $C_0$, NH, $CH_2$, O or S; and

Y is hydrogen, substituted or unsubstituted alkyl, substituted or unsubstituted cycloalkyl, substituted or unsubstituted heteroalkyl, substituted or unsubstituted heterocycloalkyl, amido, carboxyl, ester, carbonyl, formyl, thio, alkythio, sulfonyl, sulfonic acid, azidyl, nitro, isocyanate-yl, alkenyl, alkynyl, sulfonyl, sulfonic acid, phosphoryl, phosphonyl group, aryl or substituted aryl; or e) an analyte-responsive trigger group for a redox-active metal ion having the formula:

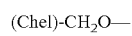

wherein: (Chel) is a metal ion chelator for the redox-active metal ion.

5. The compound of claim 4, wherein the compound is of formula (VI):

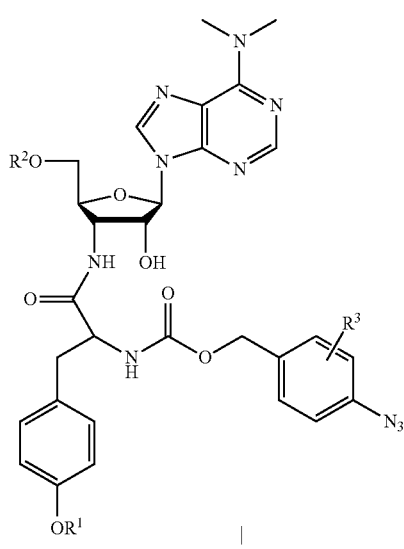

(VI)

wherein:

$R^1$, $R^2$ and each $R^3$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

6. The compound of claim 4, wherein the compound is of formula (VII):

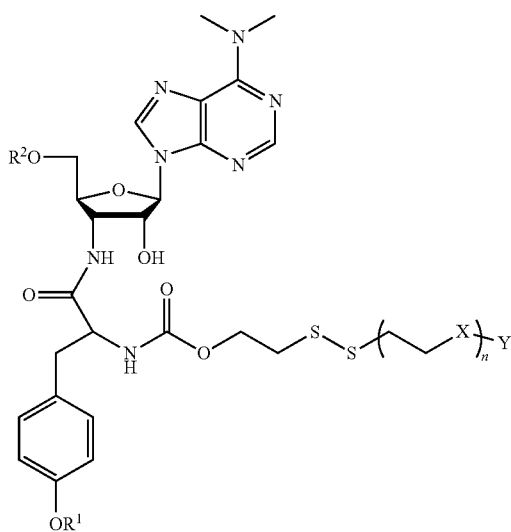

(VII)

wherein:
R$^1$ and R$^2$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl;

X is C$_0$, NH, CH$_2$, O or S;

Y is hydrogen, substituted or unsubstituted alkyl, substituted or unsubstituted cycloalkyl, substituted or unsubstituted heteroalkyl, substituted or unsubstituted heterocycloalkyl, amido, carboxyl, ester, carbonyl, alkanoyl, substituted alkanoyl, formyl, thio, alkythio, sulfonyl, sulfonic acid, azidyl, nitro, isocyanate-yl, alkenyl, alkynyl, sulfonyl, sulfonic acid, phosphoryl, phosphonyl group, aryl or substituted aryl; and n is integer from 0 to 20 (e.g., 0 to 10, 1 to 10, 1 to 6).

7. The compound of claim 4, wherein the compound is of formula (VIII):

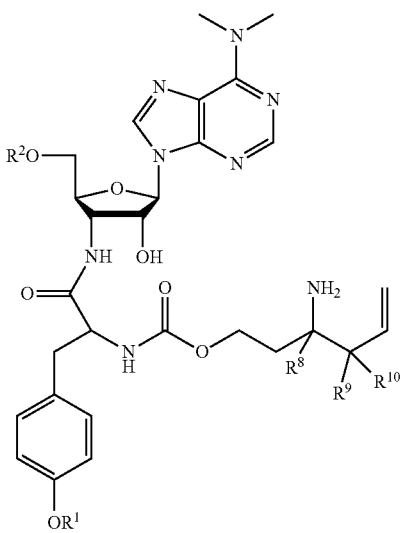

(VIII)

wherein:
R$^1$, R$^2$, R$^8$, R$^9$ and R$^{10}$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

8. The compound of claim 4, wherein the compound is of one of formulae (IX)-(XI):

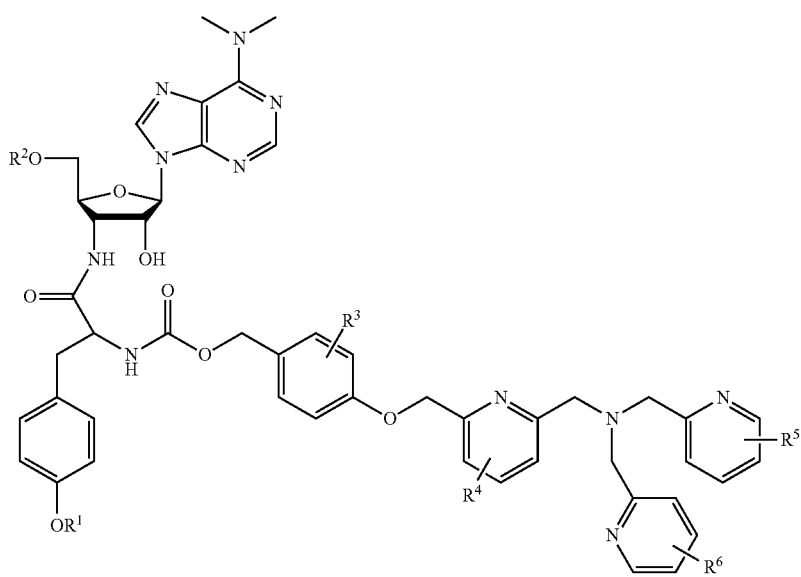

(IX)

(X)

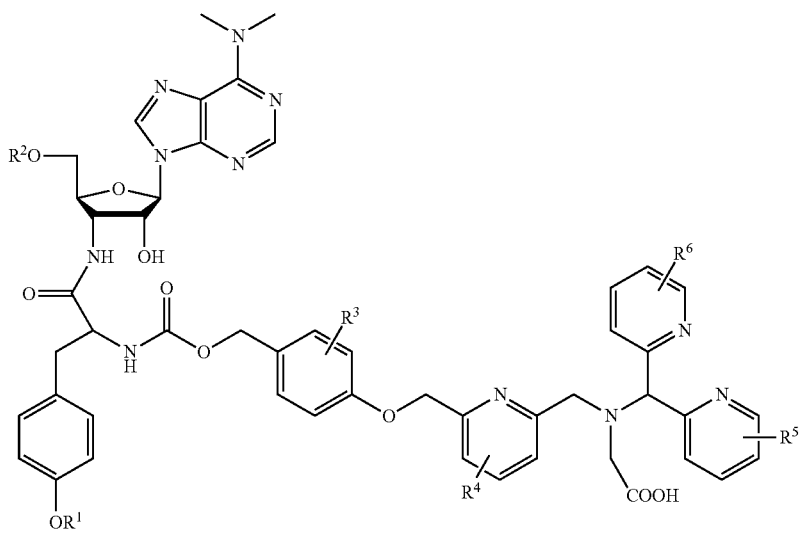

(XI)

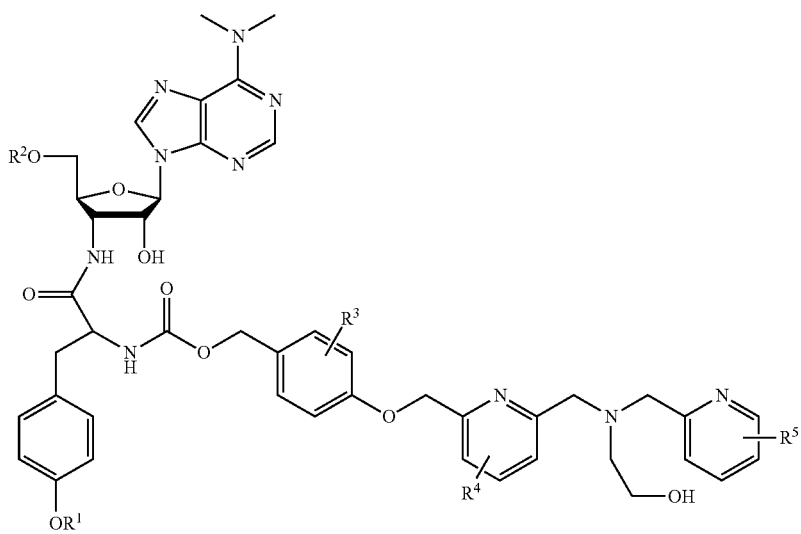

wherein:

R¹, R², R³, R⁴, R⁵ and R⁶ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl.

9. The compound of claim 1, wherein the compound is of the formula:

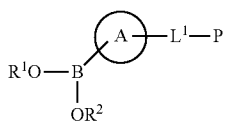

wherein:

P is the puromycin detectable moiety;

$R^1$ and $R^2$ are independently selected from hydrogen, alkyl and substituted alkyl; or $R^1$ and $R^2$ together form a boronic ester ring or substituted boronic ester ring;

A ring is selected from aryl, substituted aryl, heteroaryl, and substituted heteroaryl; and $L^1$ is cleavable linker group that provides for release of P upon reaction of the -$B(OR^1)(OR^2)$ group with a reactive oxygen species (ROS).

10. The compound of claim 9, wherein the compound is of formula (V):

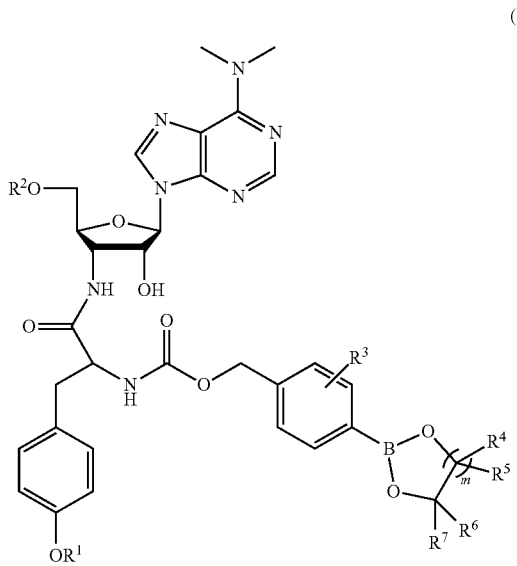

(V)

wherein:

$R^1$, $R^2$ and $R^3$ are independently hydrogen, substituted or unsubstituted alkyl, substituted or unsubstituted cycloalkyl, substituted or unsubstituted heteroalkyl, substituted or unsubstituted heterocycloalkyl, propargyl, phosphate, halogen, hydroxy, alkoxy, amino, amido, carboxyl, ester, carbonyl, formyl, thio, alkythio, sulfonyl, sulfonic acid, azidyl, cyano, nitro, isocyanate-yl, alkenyl, alkynyl, sulfonyl, sulfonic acid, phosphoryl, phosphonyl group, substituted or unsubstituted aryl, substituted or unsubstituted heteroaryl;

$R^4$, $R^5$, $R^6$ and $R^7$ are independently hydrogen, substituted or unsubstituted alkyl, and substituted or unsubstituted heteroalkyl;

m is integer selected from 1, 2 and 3.

11. The compound of claim 10, wherein $R^1$ is $CH_3$ and $R^2$ is H; and in formula (V), $R^3$ is H and $R^4$, $R^5$, $R^6$ and $R^7$ are each independently lower alkyl (e.g., methyl);

in formula (VI), $R^3$ is H;

in formula (VII), X is O, Y is alkanoyl (e.g., acetyl) and n is 1;

in formula (VIII), $R^8$, $R^9$ and $R^{10}$ are each independently lower alkyl (e.g., methyl); and in formulae (IX)-(XI), $R^3$-$R^6$ are each H.

12. The compound of claim 1, wherein the compound comprises one of the following groups masking the alpha-amino group of the puromycin detectable moiety:

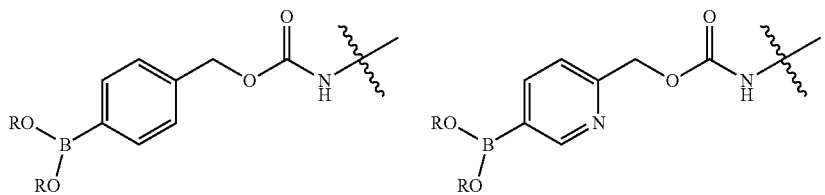

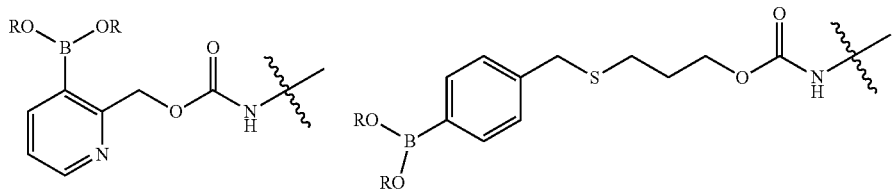

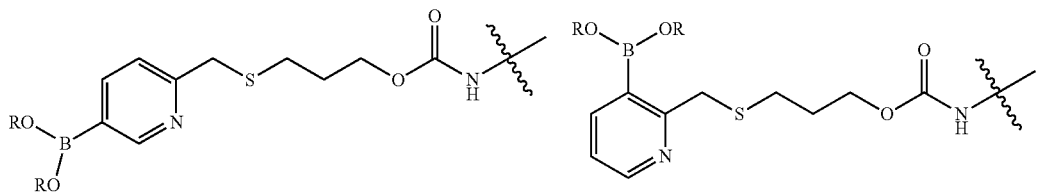

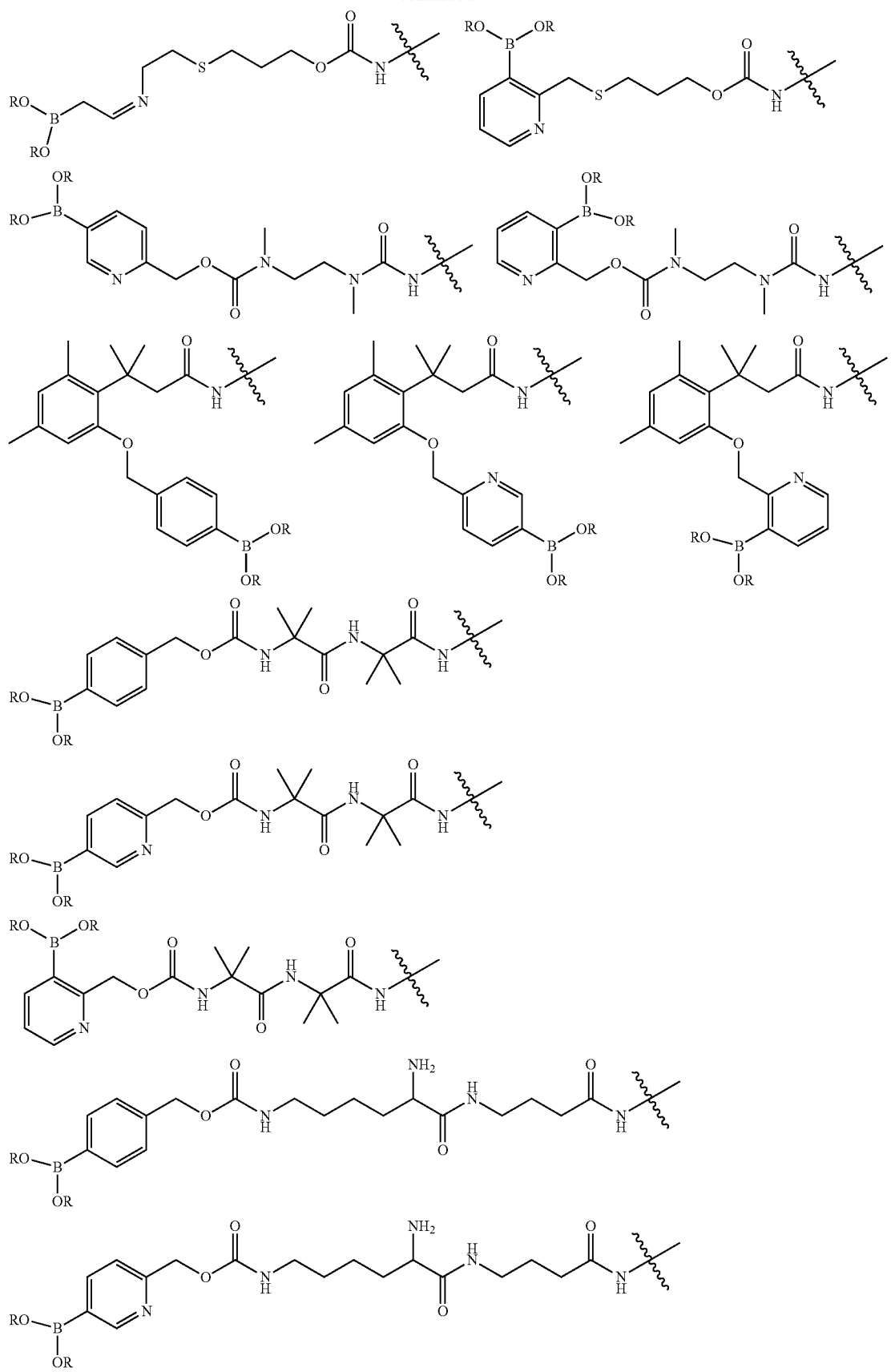

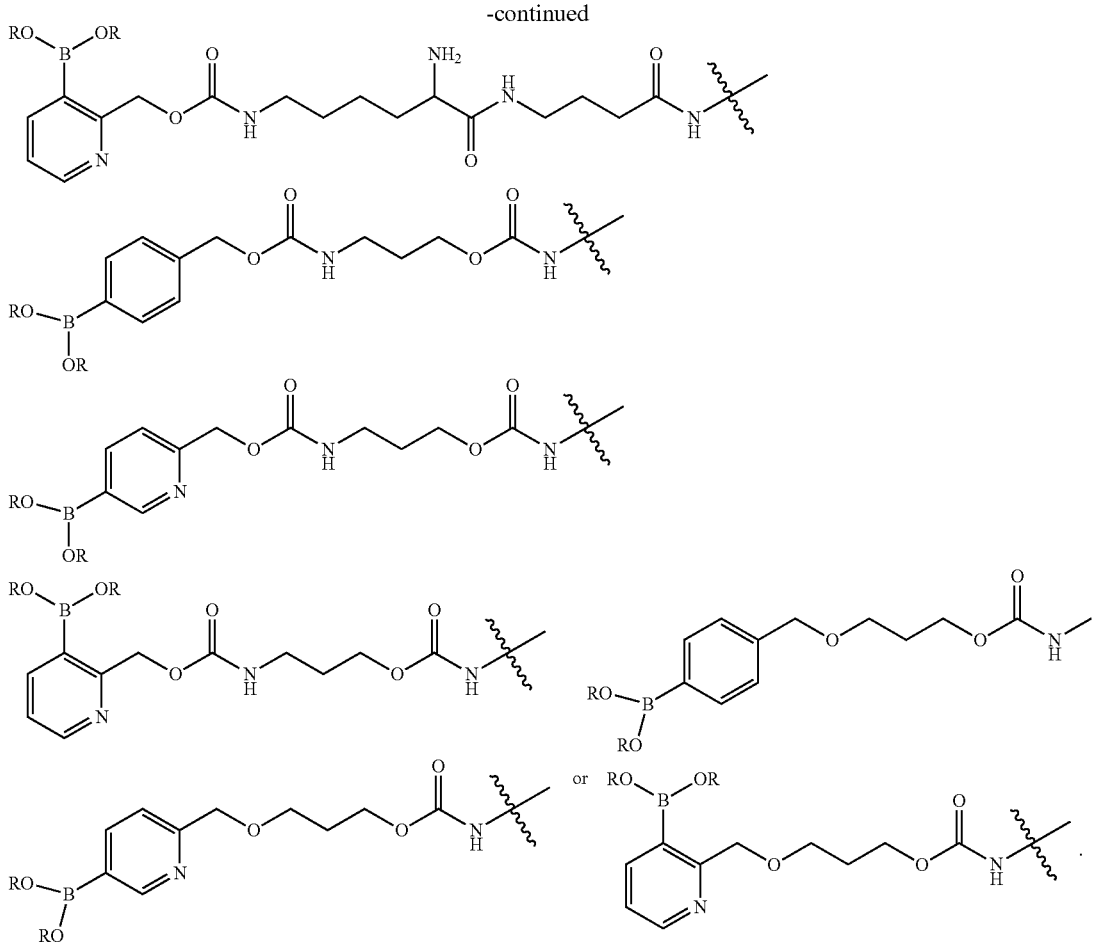

-continued wherein each R is independently selected from hydrogen, alkyl and substituted alkyl; or two R groups together form a boronic ester ring or a substituted boronic ester ring.

13. A composition comprising:
the compound of claim 1; and
a pharmaceutically acceptable excipient.

14. A kit comprising:
the compound claim 1; and
an antibody specific for a puromycylated polypeptide.

15. The kit of claim 14, wherein the antibody comprises a detectable label.

16. The kit of claim 15, wherein the detectable label comprises a fluorophore, a chromophore, or a luminophore.

17. A method of detecting a redox-active analyte in a sample, the method comprising:
contacting the sample with the compound of claim 1, wherein, in the presence of the redox-active analyte, moiety P is released from the compound and reacts with a nascent polypeptide present in the sample, thereby forming a puromycylated polypeptide; and
detecting the puromycylated polypeptide, wherein detection of the puromycylated polypeptide provides for detection of the redox-active analyte in the sample.

18. A method of detecting a redox-active analyte in a cell, tissue, organ, or fluid in a living subject, the method comprising:
administering to the subject the compound of claim 1, wherein, in the presence of the redox-active analyte, moiety P is released from the compound and reacts with a nascent polypeptide in the subject, thereby forming a puromycylated polypeptide; and
detecting the puromycylated polypeptide, wherein detection of the puromycylated polypeptide provides for detection of the redox-active analyte in the subject.

* * * * *